(12) United States Patent
Ando et al.

(10) Patent No.: US 7,705,020 B2
(45) Date of Patent: Apr. 27, 2010

(54) BENZIMIDAZOLONE CARBOXYLIC ACID DERIVATIVES

(75) Inventors: Koji Ando, Chita-gun (JP); Saturu Iguchi, Chita-gun (JP); Noriaki Murase, Chita-gun (JP); Yoshinori Murata, Chita-gun (JP); Toyoharu Numata, Chita-gun (JP); Hiroki Sone, Chita-gun (JP); Chikara Uchida, Chita-gun (JP); Tatsuo Ueki, Chita-gun (JP)

(73) Assignee: Pfizer Inc., New York, NY (US)

( * ) Notice: Subject to any disclaimer, the term of this patent is extended or adjusted under 35 U.S.C. 154(b) by 595 days.

(21) Appl. No.: 11/153,775

(22) Filed: Jun. 14, 2005

(65) Prior Publication Data

US 2005/0277673 A1 Dec. 15, 2005

Related U.S. Application Data

(60) Provisional application No. 60/607,008, filed on Sep. 2, 2004, provisional application No. 60/607,035, filed on Sep. 2, 2004, provisional application No. 60/607,048, filed on Sep. 2, 2004.

(30) Foreign Application Priority Data

Jun. 15, 2004 (JP) ............................. 2004-177488

(51) Int. Cl.
*A61K 31/445* (2006.01)
*C07D 407/14* (2006.01)

(52) U.S. Cl. .................... 514/322; 546/184; 546/192; 546/196; 546/197; 546/199; 514/315; 514/317; 514/320

(58) Field of Classification Search ................ 546/184, 546/192, 196, 197, 199; 548/300.1, 301.7, 548/302.7, 304.4, 304.7, 306.1; 514/315, 514/317, 320, 322, 385, 386, 387
See application file for complete search history.

(56) References Cited

U.S. PATENT DOCUMENTS

| | | | |
|---|---|---|---|
| 5,137,893 A | 8/1992 | Becker et al. | 514/293 |
| 5,196,547 A | 3/1993 | Becker et al. | 548/453 |
| 5,219,850 A | 6/1993 | Becker et al. | 514/214 |
| 5,223,511 A | 6/1993 | Turconi et al. | 514/304 |
| 5,260,303 A | 11/1993 | Becker et al. | |
| 5,280,028 A | 1/1994 | Flynn et al. | 514/294 |
| 5,300,512 A | 4/1994 | Flynn et al. | 514/305 |
| 5,358,954 A | 10/1994 | Turconi et al. | 514/304 |
| 5,399,562 A | 3/1995 | Becker et al. | 514/278 |
| 5,434,161 A | 7/1995 | Becker et al. | 514/300 |
| 5,521,193 A | 5/1996 | Flynn et al. | 514/290 |
| 5,534,521 A | 7/1996 | Flynn et al. | 514/290 |
| 5,552,408 A | 9/1996 | Turconi et al. | 514/304 |
| 5,576,318 A | 11/1996 | Bietti et al. | 514/253 |
| 5,591,749 A | 1/1997 | Becker et al. | 514/300 |
| 5,604,239 A | 2/1997 | Becker et al. | 514/300 |
| 5,705,498 A | 1/1998 | Gaster et al. | 514/214 |
| 5,864,039 A | 1/1999 | Kawakita et al. | 546/229 |
| 5,922,733 A | 7/1999 | Forbes et al. | 514/310 |
| 5,955,470 A | 9/1999 | Gittos | 514/294 |
| 5,968,965 A | 10/1999 | Dinsmore et al. | 514/399 |
| 6,002,009 A | 12/1999 | Cereda et al. | 546/199 |
| 6,069,152 A | 5/2000 | Schaus et al. | 514/322 |
| 6,106,864 A | 8/2000 | Dolan et al. | 424/488 |
| 6,117,882 A | 9/2000 | Schaus et al. | 514/304 |
| 6,207,697 B1 | 3/2001 | Han et al. | 514/409 |
| 6,310,059 B1 | 10/2001 | Snutch | 514/222.2 |
| 6,420,410 B1 | 7/2002 | Sperl et al. | 514/395 |
| 6,492,375 B2 | 12/2002 | Snutch | 514/255 |
| 6,548,548 B2 | 4/2003 | Campbell et al. | 514/617 |
| 6,552,042 B2 | 4/2003 | Han et al. | 514/322 |
| 6,624,162 B2 | 9/2003 | Uchida et al. | 514/233.2 |
| 6,624,184 B1 | 9/2003 | Gu et al. | 514/374 |
| 6,713,650 B2 | 3/2004 | Ibrahim et al. | 564/188 |
| 6,919,339 B2 | 7/2005 | Campbell et al. | 514/245 |
| 2002/0128232 A1 | 9/2002 | Henderson et al. | 514/79 |
| 2003/0207875 A1 | 11/2003 | Gymer et al. | 514/227.8 |

(Continued)

FOREIGN PATENT DOCUMENTS

EP 0105763 4/1984

(Continued)

OTHER PUBLICATIONS

U.S. Appl. No. 11/153,766, filed Jun. 14, 2005 (assigned to Pfizer Inc.).

(Continued)

*Primary Examiner*—Golam M Shameem
(74) *Attorney, Agent, or Firm*—Christian M. Smolizza

(57) ABSTRACT

This invention relates to compounds of the formula (I):

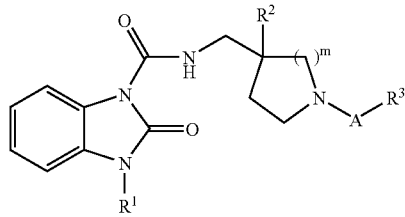

(I)

wherein $R^1$, $R^2$, $R^3$, A and m are each as described herein or a pharmaceutically acceptable salt or solvate thereof, and compositions containing such compounds and the use of such compounds in the treatment of a condition mediated by $5\text{-}HT_4$ receptor activity such as, but not limited to, gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders such as cardiac failure and heart arrhythmia, diabetes and apnea syndrome.

3 Claims, No Drawings

U.S. PATENT DOCUMENTS

| | | | |
|---|---|---|---|
| 2004/0122043 A1 | 6/2004 | Iguchi et al. | 514/303 |
| 2004/0127514 A1 | 7/2004 | Katsu et al. | 514/303 |
| 2005/0148573 A1 | 7/2005 | Katsu et al. | 514/210.16 |
| 2008/0108660 A1 | 5/2008 | Ando et al. | |

FOREIGN PATENT DOCUMENTS

| | | |
|---|---|---|
| EP | 0274867 | 7/1988 |
| EP | 0377967 | 7/1990 |
| EP | 0504679 | 9/1992 |
| EP | 0623621 | 4/1994 |
| EP | 0655439 | 5/1995 |
| EP | 0908459 | 4/1999 |
| EP | 1217000 | 6/2002 |
| FR | 2694292 | 2/1992 |
| JP | 1258674 | 10/1989 |
| JP | 2643274 | 5/1997 |
| JP | 10203987 | 8/1998 |
| JP | 20016877 | 1/2001 |
| WO | WO9100858 | 1/1991 |
| WO | WO9111172 | 8/1991 |
| WO | WO9116045 | 10/1991 |
| WO | WO9205174 | 4/1992 |
| WO | WO9212149 | 7/1992 |
| WO | WO9215593 | 9/1992 |
| WO | WO9307147 | 4/1993 |
| WO | WO9308185 | 4/1993 |
| WO | WO9318027 | 9/1993 |
| WO | WO9400449 | 1/1994 |
| WO | WO9402518 | 2/1994 |
| WO | WO9407859 | 4/1994 |
| WO | WO9408998 | 4/1994 |
| WO | WO9410174 | 5/1994 |
| WO | WO9429298 | 12/1994 |
| WO | WO9605166 | 2/1996 |
| WO | WO9631475 | 10/1996 |
| WO | WO9717345 | 5/1997 |
| WO | WO9727852 | 8/1997 |
| WO | WO9738665 | 10/1997 |
| WO | WO9847898 | 10/1998 |
| WO | WO9855148 | 12/1998 |
| WO | WO9912903 | 3/1999 |
| WO | WO9917772 | 4/1999 |
| WO | WO9950247 | 10/1999 |
| WO | WO9950264 | 10/1999 |
| WO | WO9964055 | 12/1999 |
| WO | WO0026197 | 5/2000 |
| WO | WO0035298 | 6/2000 |
| WO | WO0105763 | 1/2001 |
| WO | WO0114331 | 3/2001 |
| WO | WO0146166 | 6/2001 |
| WO | WO0164631 | 9/2001 |
| WO | WO0230886 | 4/2002 |
| WO | WO0246141 | 6/2002 |
| WO | W02004113300 | 12/2004 |
| WO | WO2005021539 | 3/2005 |

OTHER PUBLICATIONS

U.S. Appl. No. 11/153,757, filed Jun. 14, 2005 (assigned to Pfizer Inc.).

U.S. Appl. No. 10/933,629, filed Sep. 2, 2004, published as US 2005/0148473 cited above (assigned to Pfizer Inc.).

Bockaert, J., et al., The 5-HT$_4$ receptor: a place in the sun, *TipS*, vol. 13, pp. 141-145, 1992.

Ford, A. P. D. W., et al., The 5-HT$_4$ Receptor, *Medicinal Research Reviews*, vol. 13, No. 6, pp. 633-662, (1993).

Gullikson, G. W., et al., Gastrointestinal Motility Responses to the S and R Enantiomers of Zacopride, a 5-HT4 Agonist and 5-HT3 Antagonist, *Drug Development Research*, vol. 26, pp. 405-417, (1992).

Eglen, R. M., et al., Central 5-HT$_4$ receptors, *TiPS*, vol. 16, pp. 391-398, (1995).

Bockaert, J., et al., 5-HT$_4$ Receptors Potential Therapeutic Implications in Neurology and Psychiatry, *CNS Drugs*, vol. 1, No. 1, pp. 6-15, (1994).

Romanelli, M. N., et al., Synthesis and Biological Activity of a Series of Aryl Tropanyl Esters and Amides Chemically Related to 1H-Indole-3-carboxylic Acid endo 8-Methyl-8-azabicyclo[3.2.1]oct-3-yl Ester, *Arzneim,-Forsch./Drug Res.*, vol. 43 (II), No. 8, pp. 913-918, (1993).

Kaumann, A. J., et al. A 5-HT$_4$-like receptor in human right atrium, *Naunyn-Schmiedeberg's Arch Pharmacol.*, vol. 344, pp. 15-0-159, (1991).

Haleblian, J. K., Characterization of Habits and Crystalline Modification of Solids and Their Pharmaceutical Applications, *Journal of Pharmaceutical Sciences*, vol. 64, No. 8, pp. 1269-1288, (1975).

Areschka, A., et al., Recherches dans la serie des benzofurannes. LXI. Benzofurannyl-3 acetamidoximes a potentialities antihypertensives, *Eur. J. Med. Chem.—Chimica Therapuetica*, vol. 12, No. 1, pp. 87-91 (1977) (with English language abstract).

Liang, A. C., et al., Fast-dissolving intraoral drug delivery systems, *Expert Opin. Ther. Patents*, vol. 11, No. 6, pp. 981-986 (2001).

Verma, R. K., et al., Current Status of Drug Delivery Technologies and Future Directions, *Pharmaceutical Technology On-Line*, vol. 25, No. 2, pp. 1-14, (2001).

Finnin, B. C., et al., Transdermal Penetration Enhancers: Applications, Limitations, and Potential, *Journal of Pharmaceutical Sciences*, vol. 88, No. 10, pp. 955-958 (1999).

Yee, S., In vitro Permeability Across Caco-2 Cells (Colonic) Can Predict In Vivo (Small Intestinal) Absorption in Man—Fact or Myth, *Pharmceutical Research*, vol. 14, No. 6, pp. 763-766, (1997).

Tschaen, D. M., et al., Asymmetric Synthesis of MK-0499, *J. Org. Chem.*, vol. 60, pp. 4324-4330, (1995).

Tapia, I., et al., 2,3-Dihydro-2-oxo-1-H-benzimidazole-1-carboxamides with Selective Affinity for the 5-HT$_4$ Receptor: Synthesis and Structure—Affinity and Structure—Activity Relationships of a New Series of Partial Agonist and Antagonist Derivatives, *J. Med. Chem.*, vol. 42, pp. 2870-2880, (1999).

Slougui, N., et al., Reaction of Chloromethylcarbene with Katene Alkyl Silyl Acetals; A New Synthesis of 2-Methyl-2-alkenoic Esters, *Synthesis*, pp. 58-60, (1982).

Gorrichon, L., et al., Structure O-Metallee de Lithiocycloalcanecarboxylates De t-Butyle, *Journal of Organometallic Chemistry*, vol. 252, pp. 267-274, (1983).

Prugh, J. D., et al., A Simple Method of Protecting a Secondary Amine with tert Butyloxycarbonyl (BOC) in the Presence of a Primary Amine, *Synthetic Communications*, vol. 22, No. 16, pp. 2357-2360, (1992).

Nishida, H., et al., Synthesis and Evaluation of 1-Arylsulfonyl-3-piperazinone Derivatives as a Factor Xa Inhibitor II. Subsituent Effect on Biological Activities, *Chem. Pharm. Bull.*, vol. 50, No. 9, pp. 1187-1194 (2002).

Davis, C. R., et al., Tetramethyl 1,1,4,4-Cyclohexanetetracarboxylate: Preparation and Conversion to Key Presursors of Fluorinated, Stereochemically Defined Cyclohexanes, *J. Org. Chem.*, vol. 58, pp. 6843-6850, (1993).

Kuo, Y., et al., Metal Reductions of Malonates and Oxalates. A Convenient Decarboxylation Route for Disubstituted Malonates and Synthesis of Keten Acetals, *Chemical Communications*, pp. 136-137 (1971).

O'Brien, P. M., et al., Inhibitors of Acyl-CoA: Cholesterol O-Acyltransferase. Synthesis and Pharmacological Activity of (±)-2-Dodecyl-α-phenyl-N-(2,4,6-trimethoxphenyl)-2H-tetrazole-5-acetamide and Structurally Related Tetrazole Amide Derivatives, *J. Med. Chem.*, vol. 39, pp. 2354-2366, (1996).

Varie, D. L., et al., Synthesis and Biological Evaluation of Cryptophycin Analogs with Substitution at C-6 (Fragment Region), *Bioorganic & Medicinal Chemistry Letters*, vol. 9, pp. 369-374, (1999).

Okano, K., et al., Novel α-Formylation of α, α-Disubstituted Esters. Trimethylsilyl Trifluoromethanesulphonate-catalysed Reaction of Ketene Silyl Acetals with N-t-Butylformimidoyl Cyanide, *J. Chem. Soc., Chem. Commun.*, pp. 119-120, (1985).

Vacher, B., et al., Novel Derivatives of 2-Pyridinemethylamine as Selective, Potent and Orally Active Agonists at 5-$HT_{1A}$ Receptors, *J. Med. Chem.*, vol. 42, pp. 1648-1660, (1999).

Thornton, T.J., et al., Quinazoline Antifolate Thymidylate Synthase Inhibitors: Difluoro-Substituted Benzene Ring Analogues, *J. Med. Chem.*, vol. 35, pp. 2321-2327, (1992).

Okamura, W. H., et al., Thermal [1,7]-Sigmatropic Shift of Previtamin $D_3$ to Vitamin $D_3$: Synthesis and Study of Pentadeuterio Derivatives, *J. Org. Chem.*, vol. 58, pp. 600-610, (1993).

Mine, Y., et al., Comparison of Effect of Mosapride Citrate and Existing 5-$HT_4$ Receptor Agonists on Gastrointestinal Motility In Vivo and In Vitro, *J. of Pharmacology and Experimental Therapeutics*, vol 283, No. 3, pp. 1000-1008, (1997).

Bose, D. S., et al., Boron Trifluoride Promoted Cleavage of Benzyl Carbamates, *Tetrahedron Letters*, vol. 31, No. 47, pp. 6903-6906, (1990).

Bertram, G., et al., Total Synthesis of (±)-Strobiliurin E, *Tetrahedron Letters*, vol. 37, No. 44, pp. 7955-7958, (1996).

Baxter, G. S., et al., 5-Hydroxytryptamine$_4$ receptors mediate relaxation of the rat oesophageal tunica muscularis mucosae, *Naunyn-Schmiedeberg's Arch. Pharmacol.*, vol. 343, pp. 439-446, (1991).

Berge, S. M., et al., Pharmaceutical Salts, *J. of Pharmaceutical Sciences*, vol. 66, No. 1, pp. 1-19, (1977).

Cavero, I., et al., Drugs that prolong QT interval as an unwanted effect: assessing their likelihood of inducing hazardous cardiac dysrhythmias, *Exp. Opin. Pharmacother.*, vol. 1, No. 5, pp. 947-973, (2000).

Droppleman, D. A., A Simplified Method for Assessing Drug Effects on Gastric Emptying in Rats, *J. of Pharmacol. Methods*, vol. 4, pp. 227-230, (180).

Hazra, B. G., et al., An Improved Procedure for the Dichloroacetylation of Primary and Secondary Amines, *OPPI Briefs*, vol. 21, No. 3, pp. 355-358 (1989).

Reeves, J. J., et al., Investigation into the 5-hydroxytryptamine receptor mediating smooth muscle relaxation in the rat oesophagus, *Br. J. Pharmacol.*, vol. 103, pp. 1067-1072, (1991).

Satyamurthy, N., et al., Synthesis and Stereochemistry of 1-oxa-6-heterospiro[2.5]octanes. Single-crystal Analysis of 6-phenyl-1-oxa-6-phosphaspiro[2.5]octane 6-sulfide, *Phosporus and Sulfur*, vol. 19, pp. 113-129, (1984).

Schlesinger, A. H., et al., N-substituted-amides, *J. Amer. Chem. Soc.*, vol. 78, pp. 6123-6127, (1956).

Ueki, S., et al., Gastroprokinetic Activity of Nizatidine during the Digestive State in the Dog and Rat, *Arzneim.-Forsch./Drug Res.*, vol. 49 (II), pp. 618-625, (1999).

Barlow, M. G., et al., Diels-Alder reactions of tricholor-1,2,4-triazine: intramolecular additions with 1,5 and 1,6 dienes, *J. Chem. Soc., Perkin Trans.*, pp. 519-524, (1995).

Blanco, et al., Halogenation of Enol Silyl Ethers. Synthesis of Various Types of α-Bromocarbonyl Compounds, *Synthesis*, pp. 194-196, (1975).

Dumuis, A., et al., A 5-HT receptor in the central nervous system, positively coupled with adenylate cyclase, is antagonized by ICS 205 930, *European Journal of Pharm.*, pp. 187-188, vol. 146, (1988).

Dumuis, A., et al., The gastrointestinal prokinetic benzamide derivatives are agonists at the non-classical 5-HT receptor (5-$HT_4$) positively coupled to adenylate cyclase in neurons, *Naunyn-Schmiedeberg's Arch. Pharmacol.*, vol. 340, pp. 403-410, (1989).

Feibush, B., et al., Chiral Separation of Heterocyclic Drugs by HPLC: Solute-Stationary Phase Base-Pair Interactions, *J. Am. Chem. Soc.*, vol. 108, pp. 3310-3318, (1986).

Grob, C. A., et al., 226. Polar Substituent Effects in the Solvolysis of Primary and Tertiary Alkyl Halides. Polar Effect IX, *Helvetica Chimica Acta*, vol. 63, Fasc. 8, No. 226, pp. 2152-2158, (1980).

Hirokawa, Y., et al., Synthesis of N-(1-ethyl-4-methylhexahydro-1,4-diazepin-6-yl)nicotinamides and their affinities for 5-$HT_3$ and Dopamine $D_2$ Receptors, *Bioorganic & Med. Chem. Letters*, vol. 8, pp. 1551-1554, (1998).

Itoh, K., et al., Synthesis and pharmacological evaluation of carboxamide derivatives as selective serotoninergic 5-$HT_4$ receptor agonists, *Eur. J. Med. Chem.*, vol. 34, pp. 977-989, (1999).

Keenan, R. M., et al., Conformational Preferences in a Benzodiazepine Series of Potent Nonpeptide Fibrinogen Receptor Antagonists, *J. Med. Chem.*, vol. 42, pp. 545-559, (1999).

De Kimpe, N., et al., A Convenient Synthesis of 1-Chloro-2-alkanones, *Synthesis*, pp. 188-190, (1986).

Klein, S. I., et al., Design of a New Class of Orally Active Fibrinogen Receptor Antagonists, *J. Med. Chem.*, vol. 41, pp. 2492-2502, (1998).

Lantos, E., et al., Novel Cage Compounds from Inter-intra-molecular Diels-Alder Reactions of 1,2,4-Triazines with Cyclo-octa-1,5-diene, *J. Chem. Soc. Chem. Comm.*, pp. 1482-1483, (1988).

Lopez-Rodriguez, M. L., et al., Benzimidazole Derivatives. Part 1: Synthesis and Structure-Activity Relationships of New Benzimidazole -4-carboxamides and Carboxylates as Potent and Selective 5-$HT_4$ Receptor Antagonists, *Bioorganic & Med. Chem.*, vol. 7, pp. 2271-2281, (1999).

Turner, J. A., Regiospecific Electrophilic Susbtitution of Aminopyridines: Ortho Lithiation of 2-, 3-, and 4-(Pivaloylamino)pyridines, *J. Org. Chem.*, vol. 48, pp. 3401-3408, (1983).

Komatsu, T., et al., $O_2$-Binding Properties of Double-Sided Porphinatoiron(II)s with Polar Substituents and Their Human Serum Albumin Hybrids, *Bull. Chem. Soc. Jpn.*, vol 74, pp. 1695-1702 (2001).

Barnes, N. M., et al., A review of central 5-HT receptors and their function, *Neuropharmacology*, vol. 38, pp. 1083-1152, (1999).

Lumma, Jr., W. C., Condensation of Unsymmetrical Aliphatic Ketones with Formaldehyde in Trifluoroacetic Acid, vol. 35, No. 7, pp. 2391-2393, (1970).

Ohta, A., et al., Stereoselective Synthesis of Spicy Components in Peppers, *Hetercycles*, vol. 32, No. 5, pp. 965-973, (1991).

Greene, et al., Protection for the Hydroxyl Group, including 1,2 and 1,3-Diols, *Protective Groups in Organic Synthesis*, $2^{nd}$ ed., pp. 10-142, (1991).

Greene, et al., Protection for the Amino Group, *Protective Groups in Organic Synthesis*, $3^{rd}$ ed., pp. 309-405.

Greene, et al., Protection for the Carboxyl Group, *Protective Groups in Organic Synthesis*, $3^{rd}$ ed., pp. 369-377.

Mutterer, F., et al., 24. Halogenated pyridines v. fluorinated and brominated pyridine compounds, *Helvetica Chimica Acta*, vol. 59, Fasc. 1, No. 23-24, pp. 229-235, (1976), (Translation of German article).

Mattalia, G., et al., Synthesis of New Derivatives of the 4,5-Diphenyloxazole Series, *II. Farmaco—Ed. Sc.*, vol. 31, Fasc. 6, pp. 457-467 (1975).

Katz, J., et al., Acton des is propyl-9 et tertiobutyl-9 bora-9 bicyclo(3.3.1)nonanes sur quelques cetones α-br mees. Synthese de cetones substituees, *Bulletin de la Societe Chimique de France*, No. 7-8, pp. 683-687, (1977).

Chemical Abstracts, 1963, 58, 5570.

Trilateral Project B3b Mutual Understanding in Search and Examination Report on Comparative Study on biotechnology patent practices, (2001).

Greene, T. W., et al., Protection for the Carboxyl Group, *Protective Groups in Organic Synthesis*, $3^{rd}$ ed., pp. 369-453, (1999).

Greene, T. W., et al., Protection for the Amino Group, *Protective Groups in Organic Synthesis*, $3^{rd}$ ed., pp. 494-653, (1999).

Lieberman, H., et al., Pharmaceutical Dosage Forms: Tablets, vol. 1, $2^{nd}$ ed., Marcel Dekker, Inc., New York, (1980).

Zhou, Z., et al., Properties of HERG Channels Stably Expressed in HEK 293 Cells Studied at Physiological Temperature, *Biophysical Journal*, vol. 74, p. 230-241, (1998).

Murcia, C. Marta. "Diseño y síntesis de nuevos antagonistas selectivos del receptor serotoninérgico 5-HT4" (Universidad Complutense de Madrid, 2001).

Roy et al., Circulation, vol. 94, No. 4, pp. 817-823, 1996.

Marta Murcia Cremades, Diseno Y Sintesis De Nuevos Antagonistas Selectivos Del Receptor Serotoninergico 5-$HT_4$, (along with translation).

Roy, Circulation, vol. 94(4), pp. 817-823, Aug. 15, 1996.

Lopez-Rodriguez et al., Current Topics in Medicinal Chemistry, vol. 2, pp. 625-641, 2002.

TW 200305409.

Equivalent to RU 98110976/04.

Equivalent to RU 99123933/04.

Equivalent to RU 94040864/04.

BENZIMIDAZOLONE CARBOXYLIC ACID DERIVATIVES

This application claims the benefit under 35 USC § 119 of Appln. Nos. 60/607,008; 60/607,035; and 60/607,048, all filed 2 Sep. 2004, and the benefit of JP 2004-177488, filed 15 Jun. 2004, these applications being fully incorporated herein by reference.

BACKGROUND OF THE INVENTION

This invention relates to benzimidazolone carboxylic acid derivatives. These compounds have selective 5-HT$_4$ receptor agonistic activity. The present invention also relates to a pharmaceutical composition, method of treatment and use, comprising the above derivatives for the treatment of disease conditions mediated by 5-HT$_4$ receptor activity; in particular 5-HT$_4$ receptor agonistic activity.

In general, 5-HT$_4$ receptor agonists are found to be useful for the treatment of a variety of diseases such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes and apnea syndrome (See TiPs, 1992, 13, 141; Ford A. P. D. W. et al., Med. Res. Rev., 1993, 13, 633; Gullikson G. W. et al., Drug Dev. Res., 1992, 26, 405; Richard M. Eglen et al, TiPS, 1995, 16, 391; Bockaert J. Et al., CNS Drugs, 1, 6; Romanelli M. N. et al., Arzheim Forsch./Drug Res., 1993, 43, 913; Kaumann A. et al., Naunyn-Schmiedeberg's. 1991, 344, 150; and Romanelli M. N. et al., Arzheim Forsch./Drug Res., 1993, 43, 913).

WO94/00449 discloses benzimidazolone compounds as 5-HT$_4$ agonists or antagonists and/or 5-HT$_3$ antagonists. Especially, compounds represented by the following formula is disclosed as Example 10:

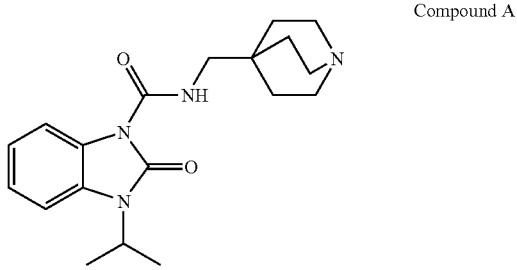

Compound A

There is a need to provide new 5-HT$_4$ agonists that are good drug candidates. In particular, preferred compounds should bind potently to the 5-HT$_4$ receptor whilst showing little affinity for other receptors and show functional activity as agonists. They should be well absorbed from the gastrointestinal tract, be metabolically stable and possess favorable pharmacokinetic properties. When targeted against receptors in the central nervous system they should cross the blood brain barrier freely and when targeted selectively against receptors in the peripheral nervous system they should not cross the blood brain barrier. They should be non-toxic and demonstrate few side-effects. Furthermore, the ideal drug candidate will exist in a physical form that is stable, non-hygroscopic and easily formulated.

SUMMARY OF THE INVENTION

In this invention, it has now been found out that (1) replacing the quinuclidine ring with a piperidine/pyrrolidine ring improves affinity for 5-HT$_4$ receptor, and/or (2) introduction of the carboxy moiety decreases affinity for dofetilide that results the prevention of the QT prolongation.

Therefore, it has now surprisingly been found that compounds of this invention have stronger selective 5-HT$_4$ agonistic activity and/or improved dofetilide affinity, compared with the prior art, and thus are useful for the treatment of disease conditions mediated by 5-HT$_4$ activity such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes and apnea syndrome (especially caused by an opioid administration).

The present invention provides a compound of the following formula (I):

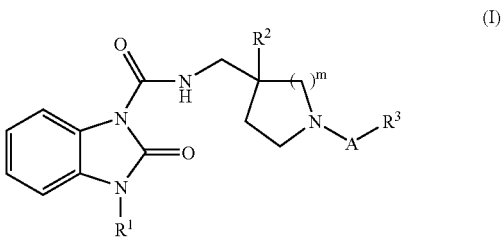

(I)

or a pharmaceutically acceptable salt or solvate thereof, wherein

A is an alkylene group having 1 to 4 carbon atoms, said alkylene group being unsubstituted or substituted with 1 to 4 substituents independently selected from the group consisting of a halogen atom, an alkyl group having 1 to 4 carbon atoms, a hydroxy-alkyl group having 1 to 4 carbon atoms and an alkoxy-alkyl group having 2 to 6 carbon atoms, wherein any 2 non-halogen substituents can be taken together with the carbon atoms to which they are attached to form a 3-, 4-, 5- or 6-membered ring optionally containing at least one heteroatom selected from N, O, and S;

$R^1$ is an isopropyl group or a cyclopentyl group;

$R^2$ is a hydrogen atom, a halogen atom or a hydroxy group;

$R^3$ is a carboxy group, a tetrazolyl group, a 5-oxo-1,2,4-oxadiazole-3-yl group or a 5-oxo-1,2,4-thiadiazole-3-yl group; and m is the integer 1 or 2.

One embodiment of the invention provides a compound of formula (I), as set forth above, or a pharmaceutically acceptable salt or solvate thereof, wherein:

A is an alkylene group having 1 to 4 carbon atoms, said alkylene group being unsubstituted or substituted with 1 to 4 substituents independently selected from the group consisting of a halogen atom, an alkyl group having 1 to 4 carbon atoms, a hydroxy-alkyl group having 1 to 4 carbon atoms and an alkoxy-alkyl group having 2 to 6 carbon atoms, wherein any 2 non-halogen substituents can be taken together with the carbon atoms to which they are attached to form a 6-membered ring optionally containing at least one heteroatom selected from N, O, and S;

$R^1$ is an isopropyl group or a cyclopentyl group;

$R^2$ is a hydrogen atom, a halogen atom or a hydroxy group;

$R^3$ is a carboxy group, a tetrazolyl group, a 5-oxo-1,2,4-oxadiazole-3-yl group or a 5-oxo-1,2,4-thiadiazole-3-yl group; and m is the integer 1 or 2.

One embodiment of the invention provides a compound of formula (I), as set forth above, or a pharmaceutically acceptable salt or solvate thereof, wherein:

A is an alkylene group having 1 to 4 carbon atoms, said alkylene group being substituted with 1 to 4 substituents independently selected from the group consisting of a halogen atom, an alkyl group having 1 to 4 carbon atoms, a hydroxy-alkyl group having 1 to 4 carbon atoms and an alkoxy-alkyl group having 2 to 6 carbon atoms, wherein any 2 non-halogen substituents can be taken together with the carbon atoms to which they are attached to form a 5-membered ring optionally containing at least one heteroatom selected from N, O, and S;

$R^1$ is an isopropyl group or a cyclopentyl group;

$R^2$ is a hydrogen atom, a halogen atom or a hydroxy group;

$R^3$ is a carboxy group, a tetrazolyl group, a 5-oxo-1,2,4-oxadiazole-3-yl group or a 5-oxo-1,2,4-thiadiazole-3-yl group; and m is the integer 1 or 2.

One embodiment of the invention provides a compound of formula (I), as set forth above, or a pharmaceutically acceptable salt or solvate thereof, wherein:

A is an alkylene group having 1 to 4 carbon atoms, said alkylene group being substituted with 1 to 4 substituents independently selected from the group consisting of a halogen atom, an alkyl group having 1 to 4 carbon atoms, a hydroxy-alkyl group having 1 to 4 carbon atoms and an alkoxy-alkyl group having 2 to 6 carbon atoms, wherein any 2 non-halogen substituents can be taken together with the carbon atoms to which they are attached to form a 3 to 4-membered ring optionally containing at least one heteroatom selected from N, O, and S;

$R^1$ is an isopropyl group or a cyclopentyl group;

$R^2$ is a hydrogen atom, a halogen atom or a hydroxy group;

$R^3$ is a carboxy group, a tetrazolyl group, a 5-oxo-1,2,4-oxadiazole-3-yl group or a 5-oxo-1,2,4-thiadiazole-3-yl group; and m is the integer 1 or 2.

Also, the present invention provides the use of a compound of formula (I), or a pharmaceutically acceptable salt or solvate thereof, each as described herein, for the manufacture of a medicament for the treatment of a condition mediated by 5-HT$_4$ receptor activity; in particular, 5-HT$_4$ agonistic activity.

Preferably, the present invention also provides the use of a compound of formula (I) or a pharmaceutically acceptable salt or solvate thereof, each as described herein, for the manufacture of a medicament for the treatment of diseases selected from gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes and apnea syndrome.

Also, the present invention provides a pharmaceutical composition comprising a compound of formula (I) or a pharmaceutically acceptable salt or solvate thereof, each as described herein, together with a pharmaceutically acceptable carrier for said compound.

Further, the present invention provides a method of treatment of a condition mediated by 5-HT$_4$ receptor activity, in a mammalian subject, which comprises administering to a mammal in need of such treatment a therapeutically effective amount of a compound of formula (I) or a pharmaceutically acceptable salt or solvate thereof, each as described herein.

Examples of conditions mediated by 5-HT$_4$ receptor activity include, but are not limited to, gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders, cardiac failure, heart arrhythmia, diabetes and apnea syndrome.

Also, the present invention provides a compound of formula (XI)

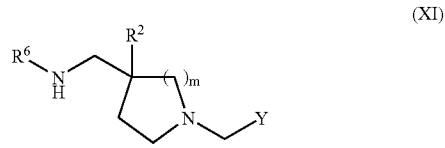

(XI)

or a salt thereof, wherein:

$R^2$ is a hydrogen atom, a hydroxy group or a halogen atom;

$R^6$ is a hydrogen atom or an amino-protecting group;

Y is an alkoxy group having 1 to 4 carbon atoms, a dialkylamino group having 2 to 8 carbon atoms, an imidazolyl group, a phtalimidyl group, succinimidyl group or sulfonyl group; and m is 1 or 2.

Also, the present invention provides a compound of formula (IXa)

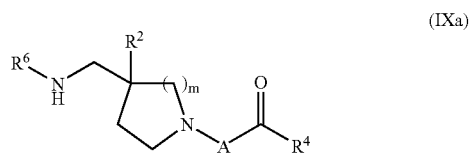

(IXa)

or a salt thereof, wherein:

A is an alkylene group having 1 to 4 carbon atoms, said alkylene group being unsubstituted or substituted with 1 to 4 substituents independently selected from the group consisting of a halogen atom, an alkyl group having 1 to 4 carbon atoms, a hydroxy-alkyl group having 1 to 4 carbon atoms and an alkoxy-alkyl group having 2 to 6 carbon atoms, wherein any 2 non-halogen substituents can be taken together with the carbon atoms to which they are attached to form a 3 to 6-membered ring optionally containing at least one heteroatom selected from N, O, and S;

$R^2$ is a hydrogen atom, a hydroxy group or a halogen atom;

$R^4$ is a hydroxy group or a carboxy-protecting group;

$R^6$ is a hydrogen atom or an amino-protecting group; and m is 1 or 2.

The compounds of the present invention may show less toxicity, good absorption, distribution, good solubility, less protein binding affinity, less drug-drug interaction, and good metabolic stability.

DETAILED DESCRIPTION OF THE INVENTION

In the compounds of the present invention:

Where A is an alkylene group having 1 to 4 carbon atoms, this may be a straight chain group, and examples include, but are not limited to, a methylene, ethylene, trimethylene and tetramethylene. Of these, methylene and ethylene are preferred; and ethylene is most preferred.

Where the substituent of A is an alkyl group having 1 to 4 carbon atoms, this may be a straight or branched chain group, and examples include, but are not limited to, a methyl, ethyl, propyl, isopropyl, butyl, isobutyl, sec-butyl and tert-butyl. Of these, alkyl groups having from 1 to 3 carbon atoms are preferred; methyl, ethyl, propyl and isopropyl are more preferred; and methyl and ethyl are most preferred.

Where the substituent of Y is an alkoxy group having 1 to 4 carbon atoms, this represents the oxygen atom substituted by the said alkyl group, and examples include, but are not limited to, a methoxy, ethoxy, propyloxy, isopropyloxy, butyloxy, isobutyloxy, sec-butyloxy and tert-butyloxy. Of these, alkyl groups having from 1 to 2 carbon atoms are preferred; methoxy are more preferred.

Where the substituent of Y is a dialkylamino group having 2 to 8 carbon atoms, this represents the amino group substituted by two of the said alkyl group, and examples include, but are not limited to, a dimethylamino, N-methyl-N-ethylamino, diethylamino, dipropylamino, diisopropylamino, dibutylamino, diisobutylamino, and N,N-di(1-methylpropyl)amino. Of these, dialkylamino groups having from 2 to 4 carbon atoms are preferred; dimethylamino, N-methyl-N-ethylamino, and diethylamino are more preferred.

Where the substituent of A is a hydroxy-alkyl group having 1 to 4 carbon atoms, this may be a straight or branched chain group, and examples include, but are not limited to, a hydroxymethyl, 2-hydroxyethyl, 1-hydroxyethyl, 3-hydroxypropyl, 2-hydroxypropyl, 2-hydroxy-1-methylethyl, 4-hydroxybutyl, 3-hydroxybutyl, 2-hydroxybutyl, 3-hydroxy-2-methylpropyl and 3-hydroxy-1-methylpropyl. Of these, hydroxy-alkyl groups having from 1 to 3 carbon atoms are preferred; hydroxymethyl, 2-hydroxyethyl, and 2-hydroxypropyl are more preferred; and hydroxymethyl and 2-hydroxyethyl are most preferred.

Where the substituent of A is an alkoxy-alkyl group having 2 to 6 carbon atoms, this may be a straight or branched chain group, and examples include, but are not limited to, a methoxymethyl, ethoxymethyl, 2-methoxyethyl, 2-ethoxyethyl, 1-methoxyethyl, 3-methoxypropyl, 3-ethoxypropyl, 2-methoxypropyl, 2-methoxy-1-methylethyl, 4-methoxybutyl, 4-ethoxybutyl, 3-methoxybutyl, 2-methoxybutyl, 3-methoxy-2-methylpropyl and 3-methoxy-1-methylpropyl. Of these, alkyloxy-alkyl groups having from 2 to 4 carbon atoms are preferred; methoxymethyl, 2-methoxyethyl and 3-methoxypropyl are more preferred; and 2-methoxyethyl and 3-methoxypropyl are most preferred.

Where any 2 non-halogen substituents of A can be taken together with the carbon atoms to which they are attached to form a 3, 4, 5, or 6-membered ring optionally containing at least one heteroatom selected from N, O and S. Such a ring may be a cycloalkyl or heterocyclyl group and examples include a cyclopropyl, cyclopentyl, cyclobutyl, cyclohexyl, methylcyclopropyl, ethylcyclopropyl, methylcyclobutyl, methylcyclopentyl, methylcyclohexyl, ethylcyclohexyl, hydroxycyclopropyl, hydroxycyclobutyl, hydroxycyclopentyl, hydroxycyclohexyl, methoxycyclopropyl, methoxycyclobutyl, methoxycyclopentyl, methoxycyclohexyl, tetrahydrofuryl and tetrahydropyranyl, preferably cyclopropyl, cyclobutyl, cyclopentyl, cyclohexyl, methoxycyclohexyl and tetrahydropyranyl, and most preferably cyclobutyl, cyclopentyl, cyclohexyl and tetrahydropyranyl.

Where the $R^6$ is the amino-protecting group, this represents a protecting group capable of being cleaved by chemical means, such as hydrogenolysis, hydrolysis, electrolysis or photolysis and such amino-protecting groups are described in Protective Groups in Organic Synthesis edited by T. W. Greene et al. (John Wiley & Sons, 1999), and examples include, but are not limited to, benzyl, $C_2H_5O(C=O)$—, $CH_3(C=O)$—, t-butyldimethylsilyl, t-butyldiphenylsilyl, benzyloxycarbonyl and t-buthoxycarbonyl. Of these groups, t-buthoxycarbonyl is preferred.

Where the $R^4$ is the carboxy-protecting group, this represents a protecting group capable of being cleaved by chemical means, such as hydrogenolysis, hydrolysis, electrolysis or photolysis and such carboxy-protecting groups are described in Protective Groups in Organic Synthesis edited by T. W. Greene et al. (John Wiley & Sons, 1999), and examples include, methoxy, ethoxy, t-butyloxy, methoxymethoxy, 2,2,2-trichloroethoxy, benzyloxy, diphenylmethoxy, trimethylsilyloxy, t-butyldimethylsilyloxy and allyloxy. Of these groups, t-butyloxy, methoxy or ethoxy is preferred.

Where $R^1$ and the substituent of A represent a halogen atom, these may be a fluorine, chlorine, bromine or iodine atom. Of these, a fluorine or a chlorine atom is preferred.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

As used herein, the article "a" or "an" refers to both the singular and plural form of the object to which it refers unless indicated otherwise.

Preferred classes of compounds of the present invention are those compounds of formula (I) or a pharmaceutically acceptable salt or solvate thereof, each as described herein, in which:

(A) $R^1$ is an isopropyl group;
(B) $R^2$ is a hydrogen atom, a fluorine atom or a hydroxy group;
(C) $R^2$ is a hydrogen atom;
(D) $R^3$ is a carboxy group or a tetrazolyl group;
(E) $R^3$ is a carboxy group;
(F) A is an alkylene group having 1 to 2 carbon atoms, said alkylene group being unsubstituted or substituted with 1 to 2 substituents independently selected from the group consisting of a halogen atom, an alkyl group having 1 to 4 carbon atoms, a hydroxy-alkyl group having 1 to 4 carbon atoms and an alkoxy-alkyl group having 2 to 6 carbon atoms, wherein any 2 non-halogen substituents can be taken together with the carbon atoms to which they are attached to form a 6-membered ring optionally containing at least one heteroatom selected from N, O and S;
(G) A is an alkylene group having from 1 to 2 carbon atoms, said alkylene group being substituted with 2 geminal substituents independently selected from the group consisting of a halogen atom, an alkyl group having 1 to 4 carbon atoms, a hydroxy-alkyl group having 1 to 4 carbon atoms and an alkoxy-alkyl group having 2 to 6 carbon atoms, wherein non-halogen geminal substituents can be taken together with the carbon atom to which they are attached to form a 6-membered ring optionally containing at least one heteroatom selected from N, O and S;

(H) A is an alkylene group having 1 to 2 carbon atoms, said alkylene group being substituted with 2 substituents independently selected from the group consisting of an alkyl group having 1 to 4 carbon atoms, a hydroxy-alkyl group having 1 to 4 carbon atoms and an alkoxy-alkyl group having 2 to 6 carbon atoms, wherein any 2 said substituents can be taken together with the carbon atoms to which they are attached to form a 5-membered ring optionally containing at least one heteroatom selected from N, O, and S;

(I) A is an alkylene group having 1 to 2 carbon atoms, said alkylene group being substituted with 2 geminal substituents independently selected from the group consisting of an alkyl group having 1 to 4 carbon atoms, a hydroxy-alkyl group having 1 to 4 carbon atoms and an alkoxy-alkyl group having 2 to 6 carbon atoms, wherein said geminal substituents can be taken together with the carbon atom to which they are attached to form a 5-membered ring optionally containing at least one heteroatom selected from N, O, and S;

(J) A is an alkylene group having 1 to 2 carbon atoms, said alkylene group being substituted with 2 substituents independently selected from the group consisting of an alkyl group having 1 to 4 carbon atoms, a hydroxy-alkyl group having 1 to 4 carbon atoms and an alkoxy-alkyl group having 2 to 6 carbon atoms, wherein said substituents can be taken together with the carbon atoms to which they are attached to form a 3 to 4-membered ring optionally containing at least one heteroatom selected from N, O, and S;

(K) A is an alkylene group having 1 to 2 carbon atoms, said alkylene group being substituted with 2 geminal substituents independently selected from the group consisting of an alkyl group having 1 to 4 carbon atoms, a hydroxy-alkyl group having 1 to 4 carbon atoms and an alkoxy-alkyl group having 2 to 6 carbon atoms, wherein said geminal substituents can be taken together with the carbon atom to which they are attached to form a 3 to 4-membered ring optionally containing at least one heteroatom selected from N, O, and S;

(L) A is

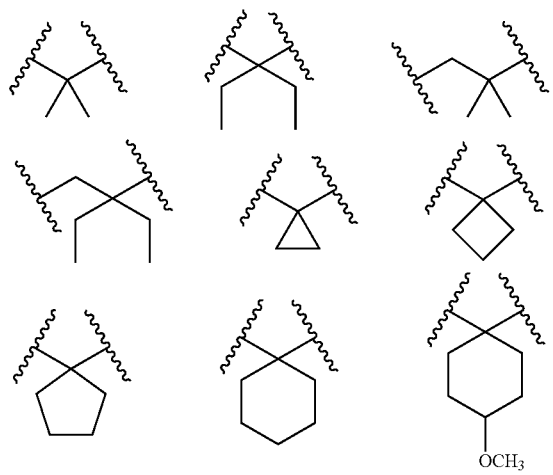

(M) A is

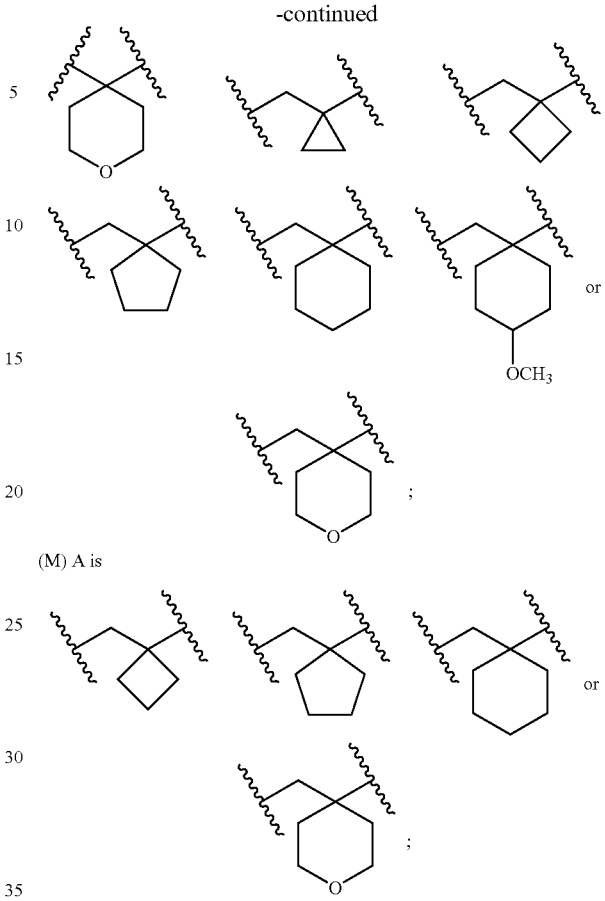

(N) A is

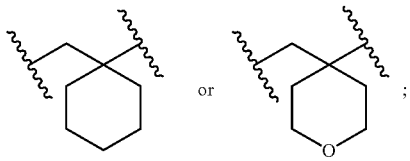

(O) A is

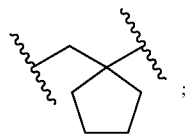

(P) A is

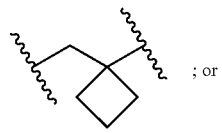

(Q) m is the integer 2.

Particularly preferred compounds of the present invention are those compounds of formula (I) or a pharmaceutically acceptable salt or solvate thereof in which (R) $R^1$ is an isopropyl group; $R^2$ is a hydrogen atom, a fluorine atom or a hydroxy group; $R^3$ is a carboxy group or a tetrazolyl group; A is an alkylene group having 1 to 2 carbon atoms, said alkylene group being unsubstituted or substituted with 1 to 2 substituents independently selected from the group consisting of a halogen atom, an alkyl group having 1 to 4 carbon atoms, a hydroxy-alkyl group having 1 to 4 carbon atoms and an alkoxy-alkyl group having 2 to 6 carbon atoms, wherein any 2 non-halogen substituents can be taken together with the carbon atoms to which they are attached to form a 6-membered ring optionally containing at least one heteroatom selected from N, O, and S; and m is the integer 2;

(S) $R^1$ is an isopropyl group; $R^2$ is a hydrogen atom; $R^3$ is a carboxy group or a tetrazolyl group; A is an alkylene group having 1 to 2 carbon atoms, said alkylene group being substituted with 2 geminal substituents independently selected from the group consisting of a halogen atom, an alkyl group having 1 to 4 carbon atoms, a hydroxy-alkyl group having 1 to 4 carbon atoms and an alkoxy-alkyl group having 2 to 6 carbon atoms, wherein said geminal substituents can be taken together with the carbon atom to which they are attached to form a 6-membered ring optionally containing at least one heteroatom selected from N, O, and S; and m is the integer 2;

(T) $R^1$ is an isopropyl group; $R^2$ is a hydrogen atom; $R^3$ is a carboxy group or a tetrazolyl group; A is

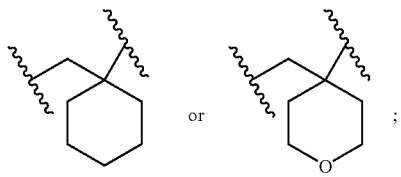

and m is the integer 2;

(U) $R^1$ is an isopropyl group; $R^2$ is a hydrogen atom, a fluorine atom or a hydroxy group; $R^3$ is a carboxy group; A is alkylene group having 1 to 2 carbon atoms, said alkylene group being unsubstituted or substituted with 1 to 2 substituents independently selected from the group consisting of a halogen atom, an alkyl group having 1 to 4 carbon atoms, a hydroxy-alkyl group having 1 to 4 carbon atoms and an alkoxy-alkyl group having 2 to 6 carbon atoms, wherein any 2 non-halogen geminal substituents can be taken together with the carbon atom to which they are attached to form a 6-membered ring optionally containing at least one heteroatom selected from N, O, and S; and m is the integer 2;

(V) $R^1$ is an isopropyl group; $R^2$ is a hydrogen atom, a fluorine atom or a hydroxy group; $R^3$ is a carboxy group; A is

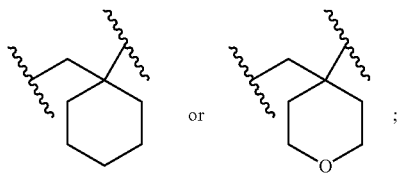

and m is the integer 2;

(W) $R^1$ is an isopropyl group; $R^2$ is a hydrogen atom, a fluorine atom or a hydroxy group; $R^3$ is a carboxy group or a tetrazolyl group; A is an alkylene group having 1 to 2 carbon atoms, said alkylene group being substituted with 2 substituents independently selected from the group consisting of an alkyl group having 1 to 4 carbon atoms, a hydroxy-alkyl group having 1 to 4 carbon atoms and an alkoxy-alkyl group having 2 to 6 carbon atoms, wherein any 2 said substituents can be taken together with the carbon atoms to which they are attached to form a 5-membered ring optionally containing at least one heteroatom selected from N, O, and S; and m is the integer 2;

(X) $R^1$ is an isopropyl group; $R^2$ is a hydrogen atom; $R^3$ is a carboxy group or a tetrazolyl group; A is an alkylene group having 1 to 2 carbon atoms, said alkylene group being substituted with 2 geminal substituents independently selected from the group consisting of an alkyl group having 1 to 4 carbon atoms, a hydroxy-alkyl group having 1 to 4 carbon atoms and an alkoxy-alkyl group having 2 to 6 carbon atoms, wherein said geminal substituents can be taken together with the carbon atom to which they are attached to form a 5-membered ring optionally containing at least one heteroatom selected from N, O, and S; and m is the integer 2;

(Y) $R^1$ is an isopropyl group; $R^2$ is a hydrogen atom; $R^3$ is a carboxy group or a tetrazolyl group; A is

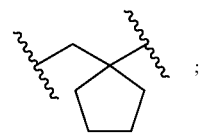

and m is the integer 2;

(Z) $R^1$ is an isopropyl group; $R^2$ is a hydrogen atom, a fluorine atom or a hydroxy group; $R^3$ is a carboxy group; A is alkylene group having 1 to 2 carbon atoms, said alkylene group being substituted with 2 substituents independently selected from the group consisting of an alkyl group having 1 to 4 carbon atoms, a hydroxy-alkyl group having 1 to 4 carbon atoms and an alkoxy-alkyl group having 2 to 6 carbon atoms, wherein any 2 said substituents can be taken together with the carbon atoms to which they are attached to form a 5-membered ring optionally containing at least one heteroatom selected from N, O, and S; and m is the integer 2;

(AA) $R^1$ is an isopropyl group; $R^2$ is a hydrogen atom, a fluorine atom or a hydroxy group; $R^3$ is a carboxy group; A is

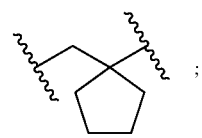

and m is the integer 2;

(AB) $R^1$ is an isopropyl group; $R^2$ is a hydrogen atom, a fluorine atom or a hydroxy group; $R^3$ is a carboxy group or a tetrazolyl group; A is an alkylene group having 1 to 2 carbon atoms, said alkylene group being substituted with 2 substituents independently selected from the group consisting of an alkyl group having 1 to 4 carbon atoms, a hydroxy-alkyl group having 1 to 4 carbon atoms and an alkoxy-alkyl group having 2 to 6 carbon atoms, wherein said substituents can be taken together with the carbon atoms to which they are attached to form a 3 to 4-membered ring optionally containing at least one heteroatom selected from N, O, and S; and m is the integer 2;

(AC) R¹ is an isopropyl group; R² is a hydrogen atom; R³ is a carboxy group or a tetrazolyl group; A is an alkylene group having 1 to 2 carbon atoms, said alkylene group being substituted with 2 geminal substituents independently selected from the group consisting of an alkyl group having 1 to 4 carbon atoms, a hydroxy-alkyl group having 1 to 4 carbon atoms and an alkoxy-alkyl group having 2 to 6 carbon atoms, wherein said geminal substituents can be taken together with the carbon atom to which they are attached to form a 3 to 4-membered ring optionally containing at least one heteroatom selected from N, O, and S; and m is the integer 2;

(AD) R¹ is an isopropyl group; R² is a hydrogen atom; R³ is a carboxy group or a tetrazolyl group; A is

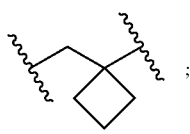
;

and m is the integer 2;

(AE) R¹ is an isopropyl group; R² is a hydrogen atom, a fluorine atom or a hydroxy group; R³ is a carboxy group; A is alkylene group having 1 to 2 carbon atoms, said alkylene group being substituted with 2 substituents independently selected from the group consisting of a halogen atom, an alkyl group having 1 to 4 carbon atoms, a hydroxy-alkyl group having 1 to 4 carbon atoms and an alkoxy-alkyl group having 2 to 6 carbon atoms, wherein any 2 non-halogen substituents can be taken together with the carbon atoms to which they are attached to form a 3 to 4-membered ring optionally containing at least one heteroatom selected from N, O, and S; and m is the integer 2;

(AF) R¹ is an isopropyl group; R² is a hydrogen atom, a fluorine atom or a hydroxy group; R³ is a carboxy group; A is

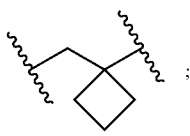
;

and m is the integer 2;

(AG) R¹ is an isopropyl group, R² is a hydrogen atom, a fluorine atom or a hydroxy group, R³ is a carboxy group, A is

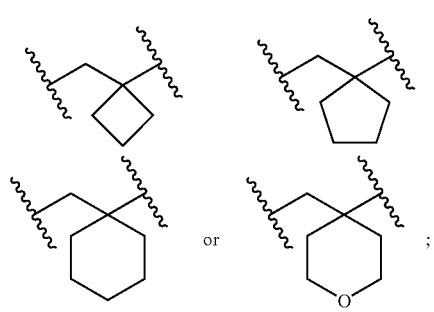

and m is the integer 2; or (AH) R¹ is an isopropyl group; R² is a hydrogen atom; R³ is a carboxy group or a tetrazolyl group; A is

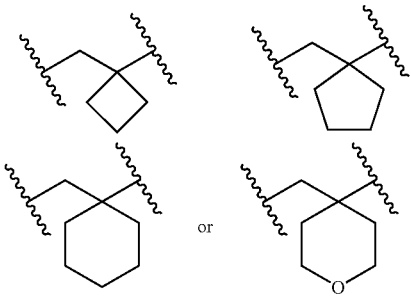
;

and m is the integer 2.

One embodiment of the invention provides a compound selected from the group consisting of:

4-{[4-({[(3-isopropyl-2-oxo-2,3-dihydro-1H-benzimidazol-1-yl)carbonyl]amino}methyl)piperidin-1-yl]methyl}tetrahydro-2H-pyran-4-carboxylic acid;

1-{[4-({[(3-isopropyl-2-oxo-2,3-dihydro-1H-benzimidazol-1-yl)carbonyl]amino}methyl)piperidin-1-yl]methyl}cyclohexanecarboxylic acid;

1-{[4-({[(3-isopropyl-2-oxo-2,3-dihydro-1H-benzimidazol-1-yl)carbonyl]amino}methyl)piperidin-1-yl]methyl}cyclopentanecarboxylic acid;

1-{([4-({[(3-isopropyl-2-oxo-2,3-dihydro-1H-benzimidazol-1-yl)carbonyl]amino}methyl)piperidin-1-yl]methyl}cyclopropanecarboxylic acid;

1-{[4-hydroxy-4-({[(3-isopropyl-2-oxo-2,3-dihydro-1H-benzimidazol-1-yl)carbonyl]amino}methyl)piperidin-1-yl]methyl}cyclohexanecarboxylic acid;

1-{[4-({[(3-isopropyl-2-oxo-2,3-dihydro-1H-benzimidazol-1-yl)carbonyl]amino}methyl)piperidin-1-yl]methyl}cyclobutanecarboxylic acid; and a pharmaceutically acceptable salt or solvate thereof.

One embodiment of the invention provides a compound from the group consisting of:

4-{[4-({[(3-isopropyl-2-oxo-2,3-dihydro-1H-benzimidazol-1-yl)carbonyl]amino}methyl)piperidin-1-yl]methyl}tetrahydro-2H-pyran-4-carboxylic acid;

1-{[4-({[(3-isopropyl-2-oxo-2,3-dihydro-1H-benzimidazol-1-yl)carbonyl]amino}methyl)piperidin-1-yl]methyl}cyclohexanecarboxylic acid;

and a pharmaceutically acceptable salt and solvate thereof.

One embodiment of the invention provides a compound from the group consisting of:

1-{[4-({[(3-isopropyl-2-oxo-2,3-dihydro-1H-benzimidazol-1-yl)carbonyl]amino}methyl)piperidin-1-yl]methyl}cyclopentanecarboxylic acid;

and a pharmaceutically acceptable salt and solvate thereof.

One embodiment of the invention provides a compound from the group consisting of:

1-{[4-({[(3-isopropyl-2-oxo-2,3-dihydro-1H-benzimidazol-1-yl)carbonyl]amino}methyl)piperidin-1-yl]methyl}cyclopropanecarboxylic acid;

1-{[4-({[(3-isopropyl-2-oxo-2,3-dihydro-1H-benzimidazol-1-yl)carbonyl]amino}methyl)piperidin-1-yl]methyl}cyclobutanecarboxylic acid;

and a pharmaceutically acceptable salt and solvate thereof.

Pharmaceutically acceptable salts of a compound of formula (I) include the acid addition and base salts (including disalts) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002). A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising a compound of the invention and one or more pharmaceutically acceptable solvent molecules, for example, ethanol. The term 'hydrate' is employed when said solvent is water.

Pharmaceutically acceptable solvates in accordance with the invention include hydrates and solvates wherein the solvent of crystallization may be isotopically substituted, e.g. $D_2O$, $d_6$-acetone, $d_6$-DMSO Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see *J Pharm Sci*, 64 (8), 1269-1288 by Haleblian (August 1975).

Hereinafter all references to a compound of formula (I) include references to salts, solvates and complexes thereof and to solvates and complexes of salts thereof.

The term "compound of the invention" or "compounds of the invention" refers to, unless indicated otherwise, a compound of formula (I) as hereinbefore defined, polymorphs, prodrugs, and isomers thereof (including optical, geometric and tautomeric isomers) as hereinafter defined and isotopically-labeled compounds of formula (I).

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985). Some examples of prodrugs in accordance with the invention include:

(i) where the compound of formula (I) contains a carboxylic acid functionality (—COOH), an ester thereof, for example, replacement of the hydrogen with $(C_1$-$C_8)$alkyl;
(ii) where the compound of formula (I) contains an alcohol functionality (—OH), an ether thereof, for example, replacement of the hydrogen with $(C_1$-$C_6)$alkanoyloxymethyl; and
(iii) where the compound of formula (I) contains a primary or secondary amino functionality (—$NH_2$ or —NHR where R≠H), an amide thereof, for example, replacement of one or both hydrogens with $(C_1$-$C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. 2H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

All of the compounds of the formula (I) can be prepared by the procedures described in the general methods presented below or by the specific methods described in the Examples section and the Preparations section, or by routine modifications thereof. The present invention also encompasses any one or more of these processes for preparing the compounds of formula (I), in addition to any novel intermediates used therein.

General Synthesis

The compounds of the present invention may be prepared by a variety of processes well known for the preparation of compounds of this type, for example as shown in the following Methods A to G.

The following Methods A and B illustrate the preparation of compounds of formula (I). Methods C through G illustrate the preparation of various intermediates.

Unless otherwise indicated, $R^1$, $R^2$, $R^3$, m and A in the following Methods are as defined above. The term "protecting group", as used hereinafter, means a hydroxy, carboxy or amino-protecting group which is selected from typical hydroxy, carboxy or amino-protecting groups described in *Protective Groups in Organic Synthesis* edited by T. W. Greene et al. (John Wiley & Sons, 1999). All starting materials in the following general syntheses may be commercially available or obtained by conventional methods known to those skilled in the art, such as *European Journal of Medicinal Chemistry*, 12(1), 87-91; 1977 and the disclosures of which are incorporated herein by reference.

Method A

This illustrates the preparation of compounds of formula (I).

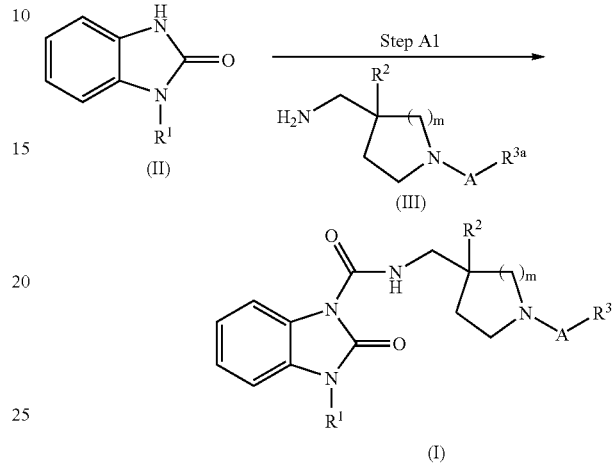

In Reaction Scheme A, $R^{3a}$ is $R^3$ as defined above or a group of formula —C(=O)—$R^4$, wherein $R^4$ is a carboxy-protecting group.

The term "carboxy-protecting group", as used herein, signifies a protecting group capable of being cleaved by chemical means, such as hydrogenolysis, hydrolysis, electrolysis or photolysis, and such carboxy-protecting groups are described in *Protective Groups in Organic Synthesis* edited by T. W. Greene et al. (John Wiley & Sons, 1999). Typical carboxy-protecting groups include, but are not limited to: methoxy, ethoxy, t-butyloxy, methoxymethoxy, 2,2,2-trichloroethoxy, benzyloxy, diphenylmethoxy, trimethylsilyloxy, t-butyldimethylsilyloxy and allyloxy. Of these groups, t-butyloxy, methoxy or ethoxy is preferred.

Step A1

In this step, the desired compound of formula (I) of the present invention is prepared by carbonylation of the compound of formula (II) with the compound of formula (III). The compound of formula (II) is commercially available. The compound of formula (III) can be prepared according to Method C set forth below.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; aromatic hydrocarbons, such as benzene, toluene and nitrobenzene; ethers, such as diethyl ether, diisopropyl ether, tetrahydrofuran and dioxane; and amides, such as N,N-dimethylformamide and N,N-dimethylacetamide. Of these solvents, dichloromethane is preferred.

There is likewise no particular restriction on the nature of the carbonylating agents used, and any carbonylating agent commonly used in reactions of this type may equally be used here. Examples of such carbonylating agents include, but are not limited to: an imidazole derivative such as N,N'-carbonyldiimidazole (CDI); a chloroformate such as trichloromethyl chloroformate and 4-nitrophenyl chloroformate; urea; and triphosgene. Of these, 4-nitrophenyl chloroformate is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

In the case where $R^{3a}$ is a group of formula —C(=O)—$R^4$, the deprotection reaction will follow to yield a carboxy group. This reaction is described in detail by T. W. Greene et al., Protective Groups in Organic Synthesis, 369-453, (1999), the disclosures of which are incorporated herein by reference. The following exemplifies a typical reaction involving the protecting group t-butyl.

The deprotection reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; and aromatic hydrocarbons, such as benzene, toluene and nitrobenzene. Of these solvents, halogenated hydrocarbons are preferred.

The deprotection reaction is carried out in the presence of an acid. There is likewise no particular restriction on the nature of the acids used, and any acid commonly used in reactions of this type may equally be used here. Examples of such acids include, but are not limited to: acids, such as hydrochloric acid, acetic acid p-toluenesulfonic acid or trifluoroacetic acid. Of these, trifluoroacetic acid is preferred.

The deprotection reaction may be carried out in the presence of a radical scavenger. There is likewise no particular restriction on the nature of the radical scavenger used, and any radical scavenger commonly used in reactions of this type may equally be used here. Examples of such radical scavengers include, but are not limited to: HBr, dimethylsulfoxide or $(CH_3CH_2)_3SiH$. Of these, $(CH_3CH_2)_3SiH$ is preferred.

The deprotection reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C., more preferably from about 0° C. to about 50° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, more preferably from about 1 hour to about 24 hours, will usually suffice.

Method B

This illustrates an alternative preparation of the desired compound of formula (I).

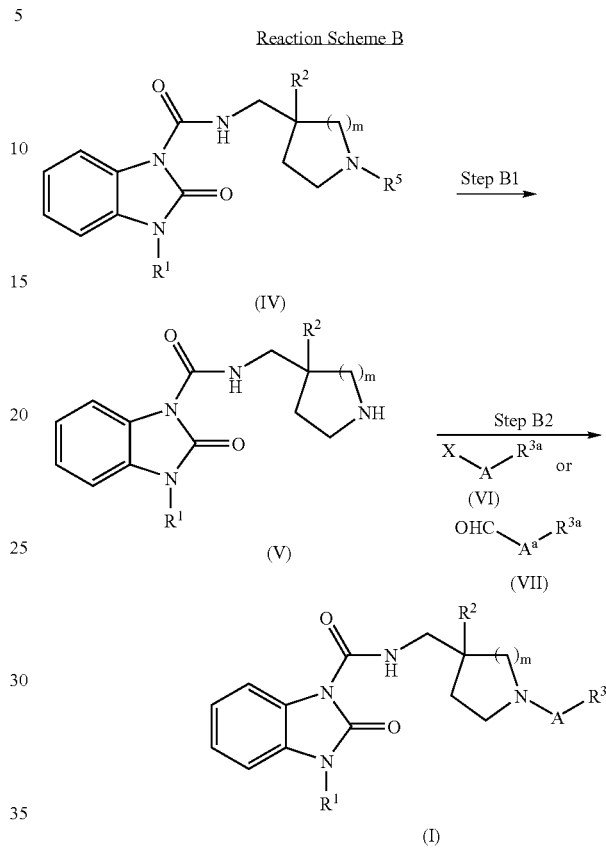

In Reaction Scheme B, $R^{3a}$ is as defined above; $R^5$ is an amino-protecting group; $A^a$ is A as defined above or an alkylene group having from 1 to 3 carbon atoms, said alkylene group being unsubstituted or substituted with 1 to 4 substituents independently selected from the group consisting of a halogen atom, an alkyl group having from 1 to 4 carbon atoms, a hydroxy-alkyl group having 1 to 4 carbon atoms and an alkoxy-alkyl group having 2 to 6 carbon atoms, wherein 2 of said substituents may optionally be taken together with the carbon atom(s) form a 3 to 6 membered ring; and X is a halogen atom such as an iodine atom, a chlorine atom or a bromine atom.

The term "amino-protecting group", as used herein, signifies a protecting group capable of being cleaved by chemical means, such as hydrogenolysis, hydrolysis, electrolysis or photolysis and such amino-protecting groups are described in Protective Groups in Organic Synthesis edited by T. W. Greene et al. (John Wiley & Sons, 1999). Typical amino-protecting groups include, but are not limited to, benzyl, $C_2H_5O(C=O)$—, $CH_3(C=O)$—, t-butyldimethylsilyl, t-butyldiphenylsilyl, benzyloxycarbonyl and t-buthoxycarbonyl. Of these groups, t-buthoxycarbonyl is preferred.

Step B1

In this step, the compound of formula (V) is prepared by the deprotection of the compound of formula (IV), which may be prepared, for example, by a method similar to that described in Method A for the preparation of the compound of formula (I) from a compound of formula (II). This deprotection method is described in detail by T. W. Greene et al. [Protective Groups in Organic Synthesis, 494-653, (1999)], the disclosures of which are incorporated herein by reference. The following exemplifies a typical method involving the protecting group t-buthoxycarbonyl.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; and alcohols, such as methanol, ethanol, propanol, 2-propanol and butanol. Of these solvents, alcohols are preferred.

The reaction is carried out in the presence of excess amount of an acid. There is likewise no particular restriction on the nature of the acids used, and any acid commonly used in reactions of this type may equally be used here. Examples of such acids include, but are not limited to: acids, such as hydrochloric acid, or trifluoroacetic acid. Of these, hydrochloric acid is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Step B2

In this step, the desired compound of formula (I) is prepared by the coupling (B2-a) of the compound of formula (V) prepared as described in Step B1 with the compound of formula (VI) or by the reductive amination (B2-b) of the compound of formula (V) with the compound of formula (VII).

(B2-a) Coupling with the Compound of Formula (V)

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; ethers, such as diethyl ether, diisopropyl ether, tetrahydrofuran and dioxane; amines, such as N-methylmorpholine, triethylamine, tripropylamine, tributylamine, diisopropylethylamine, dicyclohexylamine, N-methylpiperidine, N-methylpyrrolidine, pyridine, 4-pyrrolidinopyridine, N,N-dimethylaniline and N,N-diethylaniline; and amides, such as N,N-dimethylformamide and N,N-dimethylacetamide. Of these, N,N-dimethylformamide or N-methylpyrrolidine is preferred.

The reaction is carried out in the presence of a base. There is likewise no particular restriction on the nature of the base used, and any base commonly used in reactions of this type may equally be used here. Examples of such bases include, but are not limited to: amines, such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU); alkali metal hydrides, such as lithium hydride, sodium hydride and potassium hydride; and alkali metal alkoxides, such as sodium methoxide, sodium ethoxide, potassium t-butoxide. Of these, diisopropylethylamine is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 48 hours will usually suffice.

(B2-b) Reductive Amination

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; ethers, such as diethyl ether, diisopropyl ether, dimethoxyethane, tetrahydrofuran and dioxane; alcohols, such as methanol, ethanol, propanol, 2-propanol and butanol; acetic acid; and water. Of these solvents, halogenated hydrocarbons are preferred.

The reaction is carried out in the presence of a reducing reagent. There is likewise no particular restriction on the nature of the reducing reagents used, and any reducing reagent commonly used in reactions of this type may equally be used here. Examples of such reducing reagent include, but are not limited to: sodium borohydride, sodium cyanoborohydride and sodium triacetoxyborohydride. Of these, sodium triacetoxyborohydride is preferred. The quantity of the reducing reagent required for the reaction may also vary widely, depending on many factors, notably the reaction temperature and the nature of the starting materials and solvent employed. However, that the reaction is effected under preferred conditions, a chemical equivalent ratio of 1 to 3 of the reducing reagent to the starting material will usually suffice.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 60° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

In the case where $R^{3a}$ is a group of formula —C(=O)—$R^4$, the deprotection reaction will follow to yield a carboxy group. The reaction may be carried out under the same conditions as described in Step A1 of Method A.

Method C

This illustrates the preparation of the compound of formula (III).

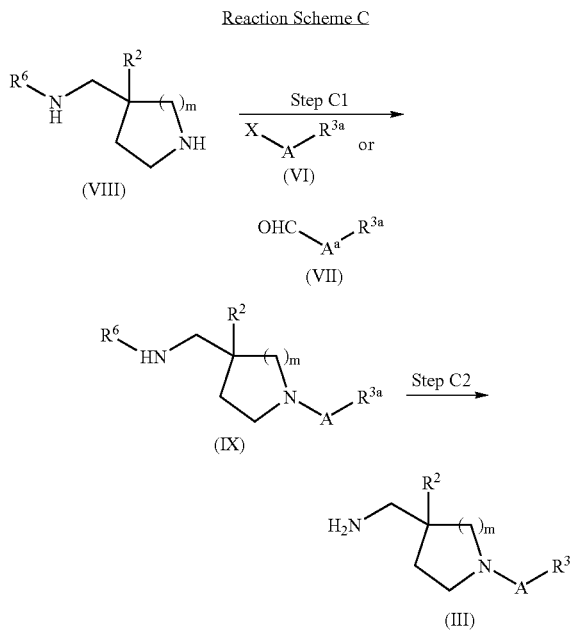

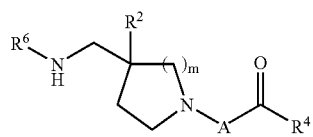

Step C1

In this step, the compound of formula (IX) is prepared by the coupling of the compound of formula (VIII) with a compound of formula (VI) or by the reductive amination of the compound of formula (VIII) with the compound of formula (VII). The compound of formula (VIII) can be prepared according to Methods F and G set forth below or is commercially available.

Step C2

In this step, the compound of formula (III) is prepared by the deprotection of the compound of formula (IX) prepared as described in Step C1. The reaction may be carried out under the same conditions as described in Step B1 of Method B.

Method D

This illustrates the preparation of the compound of formula (IIIa).

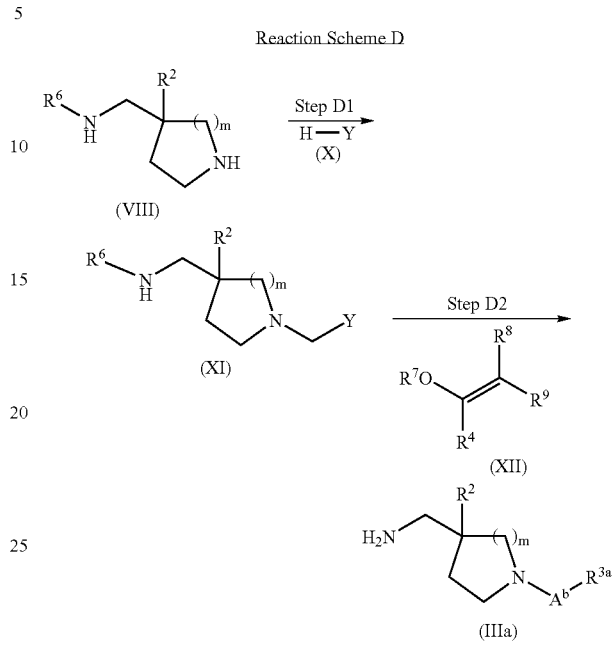

In Reaction Scheme D, $R^{3a}$, $R^4$, $R^6$ and Y are each as defined above and $R^7$ is a silyl group such as t-butyldimethylsilyl, t-butyidiphenylsilyl, triethylsilyl or trimethylsilyl, preferably trimethylsilyl; $R^8$ and $R^9$ independently represent a halogen atom, an alkyl group having 1 to 4 carbon atoms, a hydroxy-alkyl group having 1 to 4 carbon atoms and an alkoxy-alkyl group having 2 to 6 carbon atoms, wherein $R^8$ and $R^9$ may optionally be taken together with the carbon atom to which they are attached to form a 3 to 6 membered ring; $A^b$ is A as defined above with proviso a methylene group and a substituted methylene group are excluded.

Step D1

In this step, the compound of formula (XI) is prepared by condensation of the compound of formula (VIII) with the compound of formula (X) in the presence of paraformaldehyde. A compound of formula (VIII) can be prepared according to Method F and G or is commercially available.

In the case that Y is not an alkoxy group, the reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; and alcohols, such as methanol, ethanol, propanol, 2-propanol and butanol. Of these, dichloromethane or ethanol is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 48 hours, will usually suffice.

Step D2

In this step, the compound of formula (IIIa) is prepared by Mannnich reaction of the compound of formula (XI) with the compound of formula (XII).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; ethers, such as diethyl ether, diisopropyl ether, tetrahydrofuran and dioxane; nitrites, such as acetonitrile and benzonitrile; and amides, such as formamide, N,N-dimethylformamide, N,N-dimethylacetamide and hexamethylphosphoric triamide. Of these solvents, dichloromethane is preferred.

The reaction is carried out in the presence of a Lewis acid. There is likewise no particular restriction on the nature of the Lewis acids used, and any Lewis acid commonly used in reactions of this type may equally be used here. Examples of such Lewis acid include, but are not limited to: $BF_3$, $AlCl_3$, $FeCl_3$, $MgCl_2$, $AgCl$, $Fe(NO_3)_3$, $CF_3SO_3Si(CH_3)_3$, $Yb(CF_3SO_3)_3$ and $SnCl_4$. Of these, $Yb(CF_3SO_3)_3$, $MgCl_2$, or $CF_3SO_3Si(CH_3)_3$ is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Method E

This illustrates the preparation of the compound of formula (III) wherein $R^2$ is a hydrogen atom and A is $A^b$.

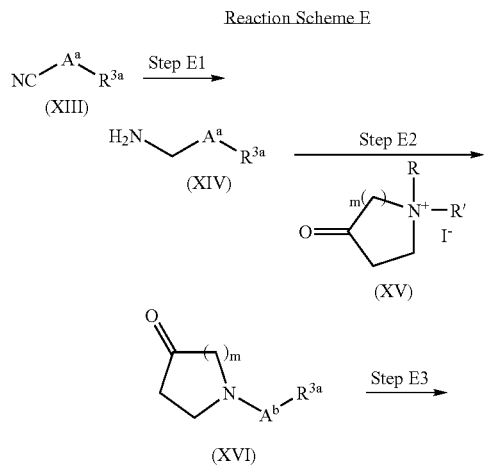

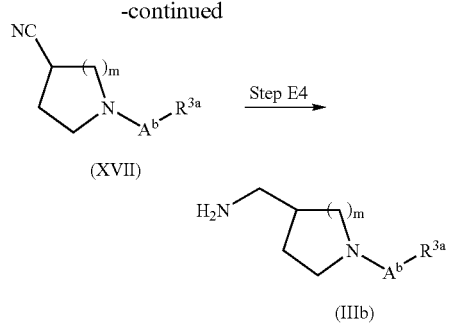

In Reaction Scheme E, $A^a$, $A^b$ and $R^{3a}$ are each as defined above; each of R and R' is an alkyl group having 1 to 4 carbon atoms, preferably a methyl group, or an aralkyl group such as a benzyl or phenethyl group, preferably a benzyl group.

Step E1

In this step, the compound of formula (XIV) is prepared by reduction of the cyano group of the compound of formula (XIII), which is commercially available.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: ethers, such as diethyl ether, diisopropyl ether, tetrahydrofuran and dioxane; aromatic hydrocarbons, such as benzene, toluene and nitrobenzene; and alcohols, such as methanol, ethanol, propanol, 2-propanol and butanol. Of these, methanol is preferred.

The reaction is carried out in the presence of a reducing agent. There is likewise no particular restriction on the nature of the reducing agents used, and any reducing agent commonly used in reactions of this type may equally be used here. Examples of such reducing agents include, but are not limited to: metal borohydrides such as sodium borohydride and sodium cyanoborohydride; combinations of hydrogen gas and a catalyst such as palladium-carbon, platinum and Raney nickel; and hydride compounds such as lithium aluminum hydride, and diisobutyl aluminum hydride. Of these, Raney nickel is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Step E2

In this step, the compound of formula (XVI) is prepared by reacting a compound of formula (XV), which is commercially available, with a compound of formula (XIV).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: water; and alcohols, such as methanol, ethanol, propanol, 2-propanol and butanol. Of these, a mixture of water and ethanol is preferred.

The reaction is carried out in the presence of a base. There is likewise no particular restriction on the nature of the base used, and any base commonly used in reactions of this type may equally be used here. Examples of such bases include, but are not limited to: alkali metal hydroxides, such as lithium hydroxide, sodium hydroxide and potassium hydroxide; alkali metal alkoxides, such as sodium methoxide, sodium ethoxide, potassium t-butoxide; and alkali metal carbonates, such as lithium carbonate, sodium carbonate and potassium carbonate. Of these, potassium carbonate is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Step E3

In this step, the compound of formula (XVII) is prepared by converting the carbonyl group of the compound of formula (XVI) to a cyano group in the presence of p-toluenesulfonylmethyl isocyanide.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: ethers, such as diethyl ether, diisopropyl ether, ethylene glycol dimethyl ether, tetrahydrofuran and dioxane; and alcohols, such as methanol, ethanol, propanol, 2-propanol and butanol. Of these, a mixture of ethylene glycol dimethyl ether and ethanol is preferred.

The reaction is carried out in the presence of a base. There is likewise no particular restriction on the nature of the base used, and any base commonly used in reactions of this type may equally be used here. Examples of such bases include, but are not limited to: alkali metal alkoxides, such as sodium methoxide, sodium ethoxide and potassium t-butoxide. Of these, potassium t-butoxide is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Step E4

In this step, the compound of formula (IIIb) is prepared by reduction of the cyano group of the compound of formula (XVII). The reaction may be carried out under the same conditions as described in Step E1 of Method E.

Method F

This illustrates the preparation of compounds of formula (VIII) wherein $R^2$ is a halogen atom.

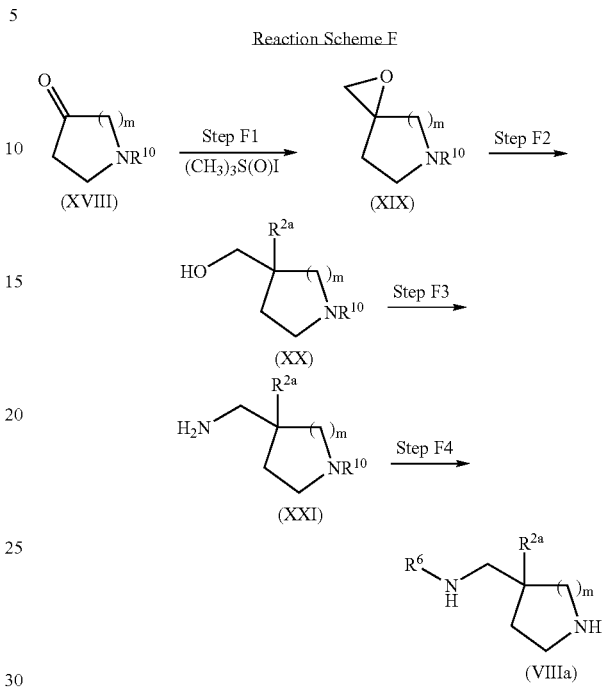

In Reaction Scheme F, $R^{2a}$ is a halogen atom; $R^6$ is as defined above; and $R^{10}$ is an amino-protecting group, preferably a benzoyl group.

Step F1

In this step, the compound of formula (XIX) is prepared by converting the carbonyl group of the compound of formula (XVIII) into the epoxide group.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: amides, such as formamide, N,N-dimethylformamide, N,N-dimethylacetamide and hexamethylphosphoric triamide; sulfoxide such as dimethyl sulfoxide or sulfolane. Of these solvents, dimethyl sulfoxide is preferred.

The reaction is carried out in the presence of a base. There is likewise no particular restriction on the nature of the base used, and any base commonly used in reactions of this type may equally be used here. Examples of such bases include, but are not limited to: alkali metal alkoxides, such as sodium methoxide, sodium ethoxide and potassium t-butoxide; and alkali metal carbonates, such as lithium carbonate, sodium carbonate and potassium carbonate. Of these, potassium t-butoxide is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C., more preferably from about 10° C. to about 50° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, more preferably from about 60 minutes to about 12 hours, will usually suffice.

Step F2

In this step, the compound of formula (XX) is prepared by reacting a hydrogen halide with the compound of formula (XIX).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: ethers, such as diethyl ether, diisopropyl ether, tetrahydrofuran and dioxane; amides, such as formamide, N,N-dimethylformamide, N,N-dimethylacetamide and hexamethylphosphoric triamide. Of these solvents, tetrahydrofuran is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C., more preferably from about 10° C. to about 50° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, more preferably from about 60 minutes to about 12 hours, will usually suffice.

Step F3

In this step, the compound of formula (XXI) is prepared by reaction of the compound of formula (XX) with sodium azide (F3-a) followed by the reduction of the azide group (F3-b).

(F3-a) Reaction with Sodium Azide

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; ethers, such as diethyl ether, diisopropyl ether, tetrahydrofuran and dioxane; amides, such as formamide, N,N-dimethylformamide, N,N-dimethylacetamide and hexamethylphosphoric triamide; and sulfoxide such as dimethyl sulfoxide and sulfolane. Of these solvents, N,N-dimethylformamide is preferred.

Before adding sodium azide, the hydroxy group is converted to a leaving group, such as a methylsulfonyl group, a trifluoromethylsulfonyl group and 4-methyl phenylsulfonyl group by adding reagents, such as trifluoromethanelsulfonylchloride, mesyl chloride and tosyl chloride. Of these reagents, mesyl chloride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

(F3-b) Reduction

The reaction may be carried out under the same conditions as described in Step E1 of Method E.

Step F4

In this step, the compound of formula (VIIIa) is prepared by introducing the amino-protecting group $R^6$ to the primary amino group (F4-a) and selectively deprotecting the amino-protecting group $R^{10}$ of the secondary amino group (F4-b).

(F4-a) Introduction of the Amino-Protecting Group

This reaction is described in detail by T. W. Greene et al. [*Protective Groups in Organic Synthesis*, 494-653, (1999)], the disclosures of which are incorporated herein by reference. The following exemplifies a typical reaction involving the protecting group t-buthoxycarbonyl.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: water; ethers, such as diethyl ether, diisopropyl ether, tetrahydrofuran and dioxane; and sulfoxide such as dimethyl sulfoxide and sulfolane. Of these solvents, tetrahydrofuran is preferred.

The reaction is carried out in the presence of reagent. There is likewise no particular restriction on the nature of the reagents used, and any reagent commonly used in reactions of this type may equally be used here. Examples of such reagents include, but are not limited to: di-t-butyl carbonate and 1-(t-butoxycarbonyl)benztriazole. Of these, di-t-butyl carbonate is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C., more preferably from about 20° C. to about 80° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, more preferably from about 60 minutes to about 12 hours, will usually suffice.

(F4-b) Deprotection

This method is described in detail by T. W. Greene et al., *Protective Groups in Organic Synthesis*, 494-653, (1999), the disclosures of which are incorporated herein by reference. The following exemplifies a typical method involving the benzoyl protecting group in the presence of combinations of hydrogen gas and a catalyst such as palladium-carbon or platinum.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; alcohols, such as methanol, ethanol, propanol, 2-propanol and butanol; and ethers, such as diethyl ether, diisopropyl ether, tetrahydrofuran and dioxane. Of these solvents, methanol is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Method G

This illustrates the preparation of compounds of formula (VIII) wherein $R^2$ is a hydroxy group.

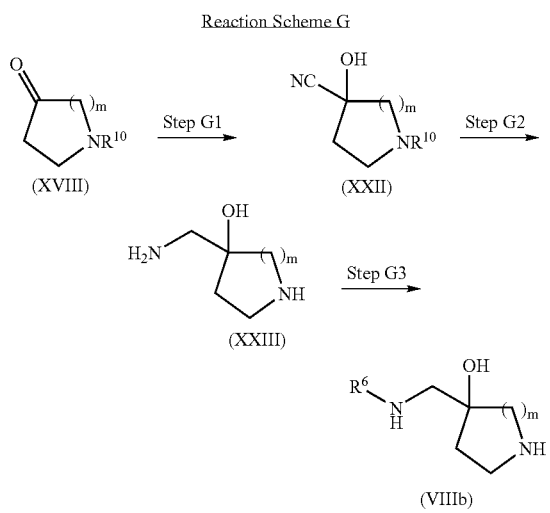

In Reaction Scheme G, $R^6$ and $R^{10}$ are each as defined above.

Step G1

In this step, the compound of formula (XXII) is prepared by reacting the carbonyl group of the compound of formula (XVIII), which is commercially available, with trimethylsilyl cyanide.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: aromatic hydrocarbons, such as benzene, toluene and nitrobenzene; halogenated hydrocarbons, such as dichloromethane, chloroform, carbon tetrachloride and 1,2-dichloroethane; ethers, such as diethyl ether, diisopropyl ether, ethylene glycol dimethyl ether, tetrahydrofuran and dioxane; nitrites, such as acetonitrile and benzonitrile; and alcohols, such as methanol, ethanol, propanol, 2-propanol and butanol. Of these, toluene is preferred.

The reaction is carried out in the presence of a reagent. There is likewise no particular restriction on the nature of the reagents used, and any reagent commonly used in reactions of this type may equally be used here. Examples of such reagent include, but are not limited to: Lewis acids, such as $BF_3$, $AlCl_3$, $FeCl_3$, $AgCl$, $ZnI_2$, $Fe(NO_3)_3$, $CF_3SO_3Si(CH_3)_3$, $Yb(CF_3SO_3)_3$ and $SnCl_4$; bases, such as CaO; ethers, such as 18-crown-6; acids, such as Amberlite XAD-4 resin. Of these, $ZnI_2$ is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours, will usually suffice.

Step G2

In this step, the compound of formula (XXIII) is prepared by converting the cyano group of the compound of formula (XXII) to an amino group followed by deprotection of the amino-protecting group $R^{10}$. The reaction may be carried out under the same conditions as described in Step E1 of Method E and Step F4 of Method F.

Step G3

In this step, the compound of formula (VIIIb) is prepared by protecting and deprotecting the amino groups of the compound of formula (XXIII). The reaction may be carried out under the same conditions as described in Step F4 of Method F.

The compounds of formula (I), and the intermediates above-mentioned preparation methods can be isolated and purified by conventional procedures, such as distillation, recrystallization or chromatographic purification.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a pharmaceutical composition or formulation in association with one or more pharmaceutically acceptable carriers or excipients. The term "carrier" or "excipient" is used herein to describe any ingredient other than the compound(s) of the invention. The choice of carrier or excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as, for example, tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include, for example, suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in *Expert Opinion in Therapeutic Patents*, 11 (6), 981-986 by Liang and Chen (2001).

For tablet dosage forms, depending on dose, the drug may make up from about 1 wt % to about 80 wt % of the dosage form, more typically from about 5 wt % to about 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from about 1 wt % to about 25 wt %, preferably from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from about 0.25 wt % to about 10 wt %, preferably from about 0.5 wt % to about 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *"Pharmaceutical Dosage Forms: Tablets, Vol. 1"*, by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, *Pharmaceutical Technology On-line*, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from about 3 to about 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, *J Pharm Sci,* 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as /-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from about 1 µg to about 20 mg of the compound of the invention per actuation and the actuation volume may vary from about 1 µl to about 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from about 1 to about 100 µg of the compound of formula (I). The overall daily dose will typically be in the range about 50 µg to about 20 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-of-Parts

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range of about 0.05 mg to about 100 mg depending, of course, on the mode of administration, preferred in the range of about 0.1 mg to about 50 mg and more preferred in the range of about 0.5 mg to about 20 mg. For example, oral administration may require a total daily dose of from about 1 mg to about 20 mg, while an intravenous dose may only require from about 0.5 mg to about 10 mg. The total daily dose may be administered in single or divided doses.

These dosages are based on an average human subject having a weight of about 65 kg to about 70 kg. The physician will readily be able to determine doses for subjects whose weight falls outside this range, such as infants and the elderly.

Combination

As discussed above, a compound of the invention exhibits 5-$HT_4$ agonist activity. A 5-$HT_4$ agonist of the present invention may be usefully combined with at least one other pharmacologically active agent or compound, particularly in the treatment of gastroesophageal reflux disease. For example, a 5-$HT_4$ agonist, particularly a compound of the formula (I), or a pharmaceutically acceptable salt or solvate thereof, as defined above, may be administered simultaneously, sequentially or separately in combination with one or more pharmacologically active agents selected from:

(i) histamine $H_2$ receptor antagonists, e.g. ranitidine, lafutidine, nizatidine, cimetidine, famotidine and roxatidine;

(ii) proton pump inhibitors, e.g. omeprazole, esomeprazole, pantoprazole, rabeprazole, tenatoprazole, ilaprazole and lansoprazole;

(iii) Acid pump antagonists, e.g. soraprazan, revaprazan (YH-1885), AZD-0865, CS-526, AU-2064 and YJA-20379-8;

(iv) oral antacid mixtures, e.g. Maalox®, Aludrox® and Gaviscon®;

(v) mucosal protective agents, e.g. polaprezinc, ecabet sodium, rebamipide, teprenone, cetraxate, sucralfate, chloropylline-copper and plaunotol;

(vi) $GABA_B$ agonists, e.g. baclofen and AZD-3355;

(vii) α2 agonists, e.g. clonidine, medetomidine, lofexidine, moxonidine, tizanidine, guanfacine, guanabenz, talipexole and dexmedetomidine;

(viii) Xanthin derivatives, e.g. Theophylline, aminophylline and doxofylline;

(ix) calcium channel blockers, e.g. aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine, and fasudil;

(x) benzodiazepine agonists, e.g. diazepam, zaleplon, zolpidem, haloxazolam, clonazepam, prazepam, quazepam, flutazolam, triazolam, lormetazepam, midazolam, tofisopam, clobazam, flunitrazepam and flutoprazepam;

(xi) prostaglandin analogues, e.g. Prostaglandin, misoprostol, treprostinil, esoprostenol, latanoprost, iloprost, beraprost, enprostil, ibudilast and ozagrel;

(xii) histamine $H_3$ agonists, e.g. R-alpha-methylhistamine and BP-294;

(xiii) anti-gastric agents, e.g. Anti-gastrin vaccine, itriglumide and Z-360;

(xiv) 5-$HT_3$ antagonists, e.g. dolasetron, palonosetron, alosetron, azasetron, ramosetron, mitrazapine, granisetron, tropisetron, E-3620, ondansetron and indisetron;

(xv) tricyclic antidepressants, e.g. imipramine, amitriptyline, clomipramine, amoxapine and lofepramine;

(xvi) GABA agonists, e.g. gabapentin, topiramate, cinolazepam, clonazepam, progabide, brotizolam, zopiclone, pregabalin and eszopiclone;

(xvii) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine and pentazocine;

(xviii) somatostatin analogues, e.g. octreotide, AN-238 and PTR-3173;

(xix) $C_1$-Channel activator: e.g. lubiprostone;

(xx) selective serotonin reuptake inhibitors, e.g. sertraline, escitalopram, fluoxetine, nefazodone, fluvoxamine, citalopram, milnacipran, paroxetine, venlafaxine, tramadol, sibutramine, duloxetine, desvenlafaxine and dapoxetine;

(xxi) anticholinergics, e.g. dicyclomine and hyoscyamine;

(xxii) laxatives, e.g. Trifyba®, Fybogel®, Konsyl®, Isogel®, Regulan®, Celevac® and Normacol®;

(xxiii) fiber products, e.g. Metamucil®.

(xxiv) antispasmodics, e.g.: mebeverine;

(xxv) dopamine antagonists, e.g. metoclopramide, domperidone and levosulpiride;

(xxvi) cholinergics, e.g. neostigmine (xxvii) AChE inhibitors, e.g. galantamine, metrifonate, rivastigmine, itopride and donepezil;

(xxviii) Tachykinin (NK) antagonists, particularly NK-3, NK-2 and NK-1 antagonists e.g. nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4]diazo cino[2,1-g][1,7]naphthridine-6-13-dione (TAK-637), 5-[[(2R,3S)-2-[(1R)-1-[3,5-bis(trifluoromethyl)phenyl] ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S).

Method for Assessing Biological Activities

The 5-$HT_4$ receptor binding affinities of the compounds of this invention are determined by the following procedures.

Human 5-$HT_4$ Binding (1)

Human 5-$HT_{4(d)}$ transfected HEK293 cells were prepared and grown in-house. The collected cells were suspended in 50 mM HEPES (pH 7.4 at 4° C.) supplemented with protease inhibitor cocktail (Boehringer, 1:1000 dilution) and homogenized using a hand held Polytron PT 1200 disruptor set at full power for 30 sec on ice. The homogenates were centrifuged at 40,000×g at 4° C. for 30 min. The pellets were then resuspended in 50 mM HEPES (pH 7.4 at 4° C.) and centrifuged once more in the same manner. The final pellets were resuspended in an appropriate volume of 50 mM HEPES (pH 7.4 at 25° C.), homogenized, aliquoted and stored at −80° C. until use. An aliquot of membrane fractions was used for protein concentration determination using BCA protein assay kit (PIERCE) and ARVOsx plate reader (Wallac).

For the binding experiments, 25 µl of test compounds were incubated with 25 µl of [$^3$H]-GR113808 (Amersham, final 0.2 nM) and 150 µl of membrane homogenate and WGA-SPA beads (Amersham) suspension solutions (10 µg protein and 1 mg SPA beads/well) for 60 minutes at room temperature. Nonspecific binding was determined by 1 µM GR113808 (Tocris) at the final concentration. Incubation was terminated by centrifugation at 1000 rpm.

Receptor-bound radioactivity was quantified by counting with MicroBeta plate counter (Wallac).

All compounds of Examples showed 5HT$_4$ receptor affinity.

Human 5-HT$_4$ Binding (2)

Human 5-HT$_{4(d)}$ transfected HEK293 cells were prepared and grown in-house. The collected cells were suspended in 50 mM Tris buffer (pH 7.4 at 4° C.) supplemented with protease inhibitor cocktail (Boehringer, 1:1000 dilution) and homogenized using a hand held Polytron PT 1200 disruptor set at full power for 30 sec on ice. The homogenates were centrifuged at 40,000×g at 4° C. for 10 min. The pellets were then resuspended in 50 mM Tris buffer (pH 7.4 at 4° C.) and centrifuged once more in the same manner. The final pellets were resuspended in an appropriate volume of 50 mM Tris buffer (pH 7.4 at 25° C.) containing 10 mM MgCl$_2$, homogenized, aliquoted and stored at −80° C. until use. An aliquot of membrane fractions was used for protein concentration determination using BCA protein assay kit (PIERCE) and ARVOsx plate reader (Wallac).

For the binding experiments, 50 µl of test compounds were incubated with 50 µl of [$^3$H] 5-HT (Amersham, final 8.0 nM) and 400 µl of membrane homogenate (300 µg protein/tube) for 60 minutes at room temperature. Nonspecific binding was determined by 50 µM GR113808 (Tocris) at the final concentration. All incubations were terminated by rapid vacuum filtration over 0.2% PEI soaked glass fiber filter papers using BRANDEL harvester followed by three washes with 50 mM Tris buffer (pH 7.4 at 25° C.). Receptor-bound radioactivity was quantified by liquid scintillation counting using Packard LS counter.

All compounds of Examples showed 5HT$_4$ receptor affinity.

Agonist-Induced cAMP Elevation in Human 5-HT$_{4(d)}$ Transfected HEK293 Cells

Human 5-HT$_{4(d)}$ transfected HEK293 cells were established in-house. The cells were grown at 37° C. and 5% CO$_2$ in DMEM supplemented with 10% FCS, 20 mM HEPES (pH 7.4), 200 µg/ml hygromycin B (Gibco), 100 units/ml penicillin and 100 µg/ml streptomycin.

The cells were grown to 60-80% confluence. On the previous day before treatment with compounds dialyzed FCS (Gibco) was substituted for normal and the cells were incubated overnight. Compounds were prepared in 96-well plates (12.5 µl/well). The cells were harvested with PBS/1 mM EDTA, centrifuged and washed with PBS. At the beginning of the assay, cell pellet was resuspended in DMEM supplemented with 20 mM HEPES, 10 µM pargyline (Sigma) and 1 mM 3-isobutyl-1-methylxanthine (Sigma) at the concentration of 1.6×10$^5$ cells/ml and left for 15 minutes at room temperature. The reaction was initiated by addition of the cells into plates (12.5 µl/well). After incubation for 15 minutes at room temperature, 1% Triton X-100 was added to stop the reaction (25 µl/well) and the plates were left for 30 minutes at room temperature. Homogenous time-resolved fluorescence-based cAMP (Schering) detection was made according to the manufacturer's instruction. ARVOsx multi-label counter (Wallac) was used to measure HTRF (excitation 320 nm, emission 665 nm/620 nm, delay time 50 µs, window time 400 µs). Data was analyzed based on the ratio of fluorescence intensity of each well at 620 nm and 665 nm followed by cAMP quantification using cAMP standard curve. Enhancement of cAMP production elicited by each compound was normalized to the amount of cAMP produced by 1000 nM serotonin (Sigma).

All compounds of Examples showed 5HT$_4$ receptor agonistic activity.

Human Dofetilide Binding

Human HERG transfected HEK293S cells were prepared and grown in-house. The collected cells were suspended in 50 mM Tris-HCl (pH 7.4 at 4° C.) and homogenized using a hand held Polytron PT 1200 disruptor set at full power for 20 sec on ice. The homogenates were centrifuged at 48,000×g at 4° C. for 20 min. The pellets were then resuspended, homogenized, and centrifuged once more in the same manner. The final pellets were resuspended in an appropriate volume of 50 mM Tris-HCl, 10 mM KCl, 1 mM MgCl$_2$ (pH 7.4 at 4° C.), homogenized, aliquoted and stored at −80° C. until use. An aliquot of membrane fractions was used for protein concentration determination using BCA protein assay kit (PIERCE) and ARVOsx plate reader (Wallac).

Binding assays were conducted in a total volume of 200 µl in 96-well plates. Twenty µl of test compounds were incubated with 20 µl of [$^3$H]-dofetilide (Amersham, final 5 nM) and 160 µl of membrane homogenate (25 µg protein) for 60 minutes at room temperature. Nonspecific binding was determined by 10 µM dofetilide at the final concentration. Incubation was terminated by rapid vacuum filtration over 0.5% presoaked GF/B Betaplate filter using Skatron cell harvester with 50 mM Tris-HCl, 10 mM KCl, 1 mM MgCl$_2$, pH 7.4 at 4° C. The filters were dried, put into sample bags and filled with Betaplate Scint. Radioactivity bound to filter was counted with Wallac Betaplate counter.

Caco-2 Permeability

Caco-2 permeability was measured according to the method described in Shiyin Yee, *Pharmaceutical Research*, 763 (1997).

Caco-2 cells were grown on filter supports (Falcon HTS multiwell insert system) for 14 days. Culture medium was removed from both the apical and basolateral compartments and the monolayers were preincubated with pre-warmed 0.3 ml apical buffer and 1.0 ml basolateral buffer for 0.5 hour at 37° C. in a shaker water bath at 50 cycles/min. The apical buffer consisted of Hanks Balanced Salt Solution, 25 mM D-glucose monohydrate, 20 mM MES Biological Buffer, 1.25 mM CaCl$_2$ and 0.5 mM MgCl$_2$ (pH 6.5). The basolateral buffer consisted of Hanks Balanced Salt Solution, 25 mM D-glucose monohydrate, 20 mM HEPES Biological Buffer, 1.25 mM CaCl$_2$ and 0.5 mM MgCl$_2$ (pH 7.4). At the end of the preincubation, the media was removed and test compound solution (10 µM) in buffer was added to the apical compartment. The inserts were moved to wells containing fresh basolateral buffer at 1 hr. Drug concentration in the buffer was measured by LC/MS analysis.

Flux rate (F, mass/time) was calculated from the slope of cumulative appearance of substrate on the receiver side and apparent permeability coefficient ($P_{app}$) was calculated from the following equation.

$$P_{app}(cm/sec) = (F*VD)/(SA*MD)$$

where SA is surface area for transport (0.3 cm$^2$), VD is the donor volume (0.3 ml), MD is the total amount of drug on the donor side at t=0. All data represent the mean of 2 inserts. Monolayer integrity was determined by Lucifer Yellow transport.

Half-Life in Human Liver Microsomes (HLM)

Test compounds (1 μM) were incubated with 3.3 mM $MgCl_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

Half-life=ln 2/k

EXAMPLES

The invention is illustrated in the following non-limiting examples in which, unless stated otherwise: all reagents are commercially available, all operations were carried out at room or ambient temperature, that is, in the range of about 18-25° C.; evaporation of solvent was carried out using a rotary evaporator under reduced pressure with a bath temperature of up to about 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254s}$ precoated HPTLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230-400 mesh ASTM) or Fuji Silysia Chromatorex® DU3050 (Amino Type, 30-50 μm). Low-resolution mass spectral data (EI) were obtained on a Integrity (Waters) mass spectrometer or a Automass 120 (JEOL) mass spectrometer. Low-resolution mass spectral data (ESI) were obtained on a ZMD2 (Waters) mass spectrometer or a Quattro II (Micromass) mass spectrometer. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc. IR spectra were measured by a Shimazu infrared spectrometer (IR-470). Optical rotations were measured using a JASCO DIP-370 Digital Polarimeter (Japan Spectroscopic Co., Ltd.). Chemical symbols have their usual meanings; b.p. (boiling point), m.p. (melting point), l (liter(s)), mL (milliliter(s)), g (gram(s)), mg (milligram(s)), mol (moles), mmol (millimoles), eq. (equivalent(s)). The powder X-ray diffraction (PXRD) pattern was determined using a Rigaku RINT-TTR powder X-ray diffractometer fitted with an automatic sample changer, a 2 theta-theta goniometer, beam divergence slits, a secondary monochromator and a scintillation counter. The sample was prepared for analysis by packing the powder on to an aluminum sample holder. The specimen was rotated by 60.00 rpm and scanned by 4°/min at room temprature with Cu—Kα radiation.

Example 1

4-{[4-({[(3-isopropyl-2-oxo-2,3-dihydro-1H-benzimidazol-1-yl)carbonyl]amino}methyl)piperidin-1-yl]methyl}tetrahydro-2H-pyran-4-carboxylic acid

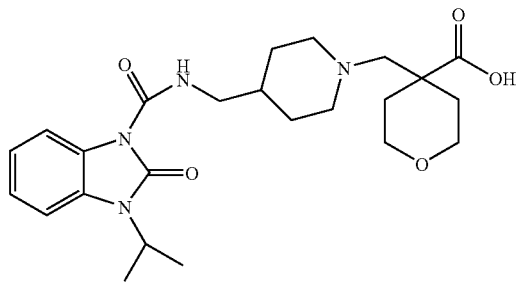

Step 1. tert-butyl 4-cyanotetrahydro-2H-pyran-4-carboxylate

To a stirred suspension of NaH (17.7 g, 0.443 mol) in DMF (200 mL) was added dropwise tert-butyl cyanoacetate (25.0 g, 0.177 mol) in DMF (100 mL) at 0° C. under $N_2$. The mixture was allowed to warm to ambient temperature, and stirred for 1 hour. Then, bis(2-bromoethyl)ether (49.3 g, 0.177 mol) was added to the mixture, and the resulting mixture was stirred at 90° C. for 24 h. After cooling to 0° C., the mixture was quenched with water (100 mL). The volatile components were removed by evaporation and the residue was precipitated with a mixture of EtOAc-Toluene (1:2, 500 mL) and water (500 mL). The organic phase was washed with water (500 mL) for three times, dried over $Na_2SO_4$, filtered and evaporated. The solid was washed with Hexane and dried in vacuo to give 19.0 g (57%) of the title compound as a white crystal.

$^1$H-NMR (CDCl$_3$) δ: 3.96 (2H, dt, J=3.9 Hz, 12.3 Hz), 3.73 (2H, dt, J=2.6 Hz, 12.3 Hz), 2.20-1.94 (4H, m), 1.52 (9 H, s).

Step 2. tert-butyl 4-(aminomethyl)tetrahydro-2H-pyran-4-carboxylate

A mixture of tert-butyl 4-cyanotetrahydro-2H-pyran-4-carboxylate (18.95 g, 0.0897 mol, step 1) and Raney Ni (1.00 g) in methanol (200 mL) was hydrogenated (3 atm) at room temperature for 12 h. Then, the mixture was filtered through a pad of Celite, and the filtrate was concentrated in vacuo to give 16.01 g (83%) of the title compound as a yellow syrup.

$^1$H-NMR (CDCl$_3$) δ: 3.86 (2H, dt, J=4.1 Hz, 11.4 Hz), 3.48 (2H, dt, J=2.5 Hz, 11.5 Hz), 2.75 (2H, s), 2.03 (2H, br d, J=10.7 Hz), 1.55-1.35 (13H, m, including 9H, s, 1.49 ppm).

Step 3. tert-butyl 4-[(4-oxopiperidin-1-yl)methyl] tetrahydro-2H-pyran-4-carboxylate To a refluxing mixture of tert-butyl 4-(aminomethyl)tetrahydro-2H-pyran-4-carboxylate (8.00 g, 0.0372 mol, step 2) and $K_2CO_3$ (0.51 g, 0.0372 mol) in EtOH—$H_2O$ (2:1, 240 mL) was added dropwise 1-ethyl-1-methyl-4-oxopiperidinium iodide (12.0 g, 0.0445 mol, J. Org. Chem. 1995, 60, 4324-4330) in EtOH—$H_2O$ (2:1, 150 mL), and the resulting mixture was stirred at the same temperature (reflux) for 1 h. After cooling to room temperature, the solvent was removed in vacuo. The residue was poured into sat. $NaHCO_3$ aq. (200 mL), and the mixture was extracted with $CH_2Cl_2$ (200 mL×three times). The extracts were dried over $Na_2SO_4$ and concentrated. The residue was chromatographed on a column of silica gel eluting with hexane/ethyl acetate (3:1 to 2:1) to give 10.77 g (98%) of the title compound as a colorless syrup.

MS (ESI) m/z: 298 (M+H)$^+$.

$^1$H NMR (CDCl$_3$) δ 3.84 (2H, br d, J=11.4 Hz), 3.50 (2H, dt, J=2.0 Hz, 11.7 Hz), 2.85 (4H, t, J=5.9 Hz), 2.61 (2H, s), 2.39 (4H, t, J=6.1 Hz), 2.05 (2H, d, J=11.5 Hz), 1.75-1.45 (11H, m, including 9H, s, 1.49 ppm).

Step 4. tert-butyl 4-[(4-cyanopiperidin-1-yl)methyl] tetrahydro-2H-pyran-4-carboxylate To a stirred solution of tert-butyl 4-[(4-oxopiperidin-1-yl) methyl]tetrahydro-2H-pyran-4-carboxylate (8.77 g, 0.0295 mol, step 3) in 1,2-dimethoxyethane (250 mL) was added p-toluenesulfonylmethyl isocyanide (11.51 g, 0.0590 mol), EtOH (3.96 mL, 0.0678 mol) and t-BuOK (11.58 g, 0.1032 mol) at 0° C. The resulting mixture was stirred at 50° C. for 16 h. After cooling, the reaction mixture was poured into sat. $NaHCO_3$ aq. (200 mL), and the mixture was extracted with $CH_2Cl_2$ (200 mL×3 times). The extracts were dried over $Na_2SO_4$ and concentrated. The residue was chromatographed on a column of silica gel eluting with hexane/ethyl acetate (2:1) to give 5.76 g (63%) of the title compound as a yellow syrup.

MS (ESI) m/z: 309 (M+H$^+$).

$^1$H-NMR (CDCl$_3$) δ: 3.81 (2H, dt, J=3.1 Hz, 11.0 Hz), 3.48 (2H, dt, J=2.1 Hz, 11.7 Hz), 2.76-2.64 (2H, m), 2.64-2.52 (1H, m), 2.50-2.35 (4H, m, including 2H, s, 2.46 ppm), 1.98 (2H, br d, J=11.9 Hz), 1.92-1.70 (4 H, m), 1.65-1.40 (11H, m, including 9H, s, 1.47 ppm).

Step 5. tert-butyl 4-{[4-(aminomethyl)piperidin-1-yl] methyl}tetrahydro-2H-pyran-4-carboxylate A mixture of tert-butyl 4-[(4-cyanopiperidin-1-yl)methyl] tetrahydro-2H-pyran-4-carboxylate (5.76 g, 0.0187 mol, step 4) and Raney Ni (3.00 g) in methanol (100 mL) was hydrogenated (3 atm) at room temperature for 12 h. Then, the mixture was filtered through a pad of Celite, and the filtrate was concentrated in vacuo to give 5.72 g (98%) of the title compound as a yellow syrup.

MS (ESI) m/z: 313 (M+H$^+$).

$^1$H-NMR (CDCl$_3$) δ: 3.80 (2H, dt, J=3.1 Hz, 11.5 Hz), 3.49 (2H, dt, J=2.1 Hz, 12.2 Hz), 2.80 (2H, br d, J=11.5 Hz), 2.58-2.40 (4H, m, including 2H, s, 2.43 ppm), 2.15 (2H, br t, J=7.3 Hz), 1.98 (2H, br d, J=13.7 Hz), 1.70-1.40 (16H, m, including 9H, s, 1.47 ppm), 1.30-1.10 (2H, m).

Step 6. tert-butyl 4-{[4-({[(3-isopropyl-2-oxo-2,3-dihydro-1H-benzimidazol-1-yl)carbonyl] amino}methyl)piperidin-1-yl]methyl}tetrahydro-2H-pyran-4-carboxylate A mixture of p-nitrophenylchloroformate (4.14 g, 0.0205 mol), 1-isopropyl-1,3-dihydro-2H-benzimidazol-2-one (3.62 g, 0.0205 mol, J. Med. Chem. 1999, 42, 2870-2880) and Et$_3$N (7.81 mL, 0.0560 mol) in CH$_2$Cl$_2$ (100 mL) was stirred at room temperature for 4 h. Then, tert-butyl 4-{[4-(aminomethyl)piperidin-1-yl]methyl}tetrahydro-2H-pyran-4-carboxylate (5.72 g, 0.0187 mol, step 5) was added, and the resulting mixture was stirred at room temperature for 24 h. The reaction mixture was diluted with sat. NaHCO$_3$ aq. (300 mL), extracted with CH$_2$Cl$_2$ (300 mL) for three times. The combined extract was dried over Na$_2$SO$_4$ and concentrated. The residue was chromatographed on a column of NH-silica gel eluting with hexane/ethyl acetate (1:1) to give 9.83 g (100%) of the title compound as a yellow syrup.

MS (ESI) m/z: 515 (M+H)$^+$.

$^1$H NMR (CDCl$_3$) δ 8.90 (1H, t, J=4.9 Hz), 8.31-8.21 (1H, m), 7.25-7.10 (3H, m), 4.80-4.60 (1H, m), 3.80 (2H, dt, J=3.1 Hz, 11.5 Hz), 3.49 (2H, dt, J=1.7 Hz, 11.4 Hz), 3.28 (2H, t, J=6.4 Hz), 2.81 (2H, br d, J=10.4 Hz), 2.44 (2H, s), 2.16 (2H, t, J=10.4 Hz), 1.98 (2H, d, J=12.4 Hz), 1.81-1.20 (22H, m, including 6 H, d, J=7.1 Hz, 1.56 ppm and 9H, s, 1.47 ppm).

Step 7. 4-{[4-({[(3-isopropyl-2-oxo-2,3-dihydro-1H-benzimidazol-1-yl)carbonyl]amino}methyl)piperidin-1-yl]methyl}tetrahydro-2H-pyran-4-carboxylic acid To a stirred solution of tert-butyl 4-{[4-({[(3-isopropyl-2-oxo-2,3-dihydro-1H-benzimidazol-1-yl)carbonyl] amino}methyl)piperidin-1-yl]methyl}tetrahydro-2H-pyran-4-carboxylate (3.67 g, 7.13 mmol, step 6) in THF (80 mL) was added conc. HCl (40 mL) at 0° C. and the resulting mixture was stirred for 20 h at room temperature. The mixture was concentrated to remove the solvent and the residue was poured into sat. NaHCO$_3$ aq. The mixture was extracted with CH$_2$Cl$_2$ for three times and the organic layer was dried over Na$_2$SO$_4$. Removal of the solvent gave a residue, which was chromatographed on a column of silica gel eluting MeOH/CH$_2$Cl$_2$ (1:10) to give 3.01 g (92%) of the title compound. The product was recrystalized from THF to give the titled compound (0.893 g) as white crystals.

MS (ESI) m/z: 459 (M+H)$^+$.

$^1$H NMR (CDCl$_3$) δ 8.99 (1H, t, J=5.6 Hz), 8.30-8.15 (1H, m), 7.25-7.105 (3H, m), 4.80-4.60 (1H, m), 3.95-3.70 (4H, m), 3.34 (2H, t, J=6.3 Hz), 3.14 (2H, br d, J=12.0 Hz), 2.65-2.45 (4H, m, including 2H, s, 2.59 ppm), 1.92 (4H, t, J=13.8 Hz), 1.85-1.40 (11H, m, including 6H, d, J=6.9 Hz, 1.57 ppm).

m.p.: 176° C.

IR (KBr) v: 3281, 2947, 1720, 1688, 1611, 1595, 1547, 1481, 1447, 1375, 1200, 1159, 1136, 1105, 760 cm$^{-1}$.

Anal. calcd. for C$_{24}$H$_{34}$N$_4$O$_5$: C, 62.86; H, 7.47; N, 12.22. Found: C, 62.77; H, 7.42; N, 12.16.

Alternative route to synthesize 4-{[4-({[(3-Isopropyl-2-oxo-2,3-dihydro-1H-benzimidazol-1-yl)carbonyl] amino}methyl)piperidin-1-yl]methyl}tetrahydro-2H-pyran-4-carboxylic acid is described below.

Step 8. tert-Butyl {[1-(ethoxymethyl)piperidin-4-yl]methyl}carbamate

To a stirred solution of tert-butyl (piperidin-4-ylmethyl)carbamate (7.0 g, 33 mmol) in ethanol (19 mL), paraformaldehyde (1.2 g, 39 mmol) and potassium carbonate (5.4 g, 39 mmol) were added at ambient temperature. The mixture was stirred at ambient temperature for 4 h. The mixture was filtered and the filter cake was washed with ethanol (50 mL). The volatile components were removed by evaporation to give the title compound 8.9 g (quant.) as a white powder.

$^1$H-NMR (CDCl$_3$) δ: 4.60 (1H, brs), 4.07 (2H, s), 3.49 (2H, q, J=7.1 Hz), 3.08-2.83 (4H, m), 2.50-2.36 (2 H, m), 1.75-1.60 (2H, m), 1.44 (9H, s), 1.52-1.35 (1H, m), 1.19 (3H, t, J=7.1 Hz), 1.31-1.12 (2H, m).

Step 9. [Methoxy(tetrahydro-4H-pyran-4-ylidene)methoxy](trimethyl)silane

To a stirred solution of diisopropylamine (1.6 g, 0.016 mol) in tetrahydrofuran (4 mL) was added dropwise n-butyllithium (1.59 M in hexane, 9.2 mL, 0.014 mol) at 0° C. under nitrogen, and stirred for 20 min. Then, the reaction mixture was cooled to −40° C., methyl tetrahydro-2H-pyran-4-carboxylate (1.9 g, 0.013 mol) and trimethylsilyl chloride (2.0 mL, 0.015 mol) in tetrahydrofuran (1 mL) was added, and the resulting mixture was gradually warmed to room temperature over 3 h. The volatile components were removed by evaporation and the residue was filtered through a pad of celite washing with hexane. The filtrate was dried in vacuo to give 2.9 g (quant.) of the title compound as a clear yellow oil.

$^1$H-NMR (CDCl$_3$) δ: 3.64-3.59 (4H, m), 3.52 (3H, s), 2.24 (2H, t, J=5.2 Hz), 2.15 (2H, t, J=5.3 Hz), 0.22 (9H, s).

Step 10. 4-[(4-{[(tert-butoxycarbonyl)amino]methyl}piperidin-1-yl)methyl]tetrahydro-2H-pyran-4-carboxylate To a stirred solution of tert-butyl {[1-(ethoxymethyl)piperidin-4-yl]methyl}carbamate (4 g, 14 mmol, Step 8) and [methoxy(tetrahydro-4H-pyran-4-ylidene)methoxy](trimethyl)silane (2.9 g, 13 mmol, Step 9) in dichloromethane (30 mL) was added dropwise trimethylsilyl trifluoromethanesulfonate (0.24 mL, 1.3 mmol) at 0° C., and the resulting mixture was stirred at room temperature for 12 h. The reaction mixture was quenched with saturated aqueous sodium bicarbonate (150 mL), extracted with dichloromethane (30 mL×2), and the combined organic layer was dried over sodium sulfate. Removal of the solvent gave a residue, which was chromatographed on a column of silica gel eluting with ethyl acetate/hexane (1:1) to give 6.3 g (64%) of the title compound as a clear colorless oil.

MS (ESI) m/z: 371 (M+H)$^+$.

$^1$H-NMR (CDCl$_3$) δ: 4.57 (1H, br s), 3.84-3.78 (2H, m), 3.70 (3H, s), 3.49-3.41 (2H, m), 2.99-2.95 (2H, m), 2.73-2.68 (2H, m), 2.47 (2H, s), 2.19-2.11 (2H, m), 2.06-2.01 (2H, m), 1.61-1.51 (5H, m), 1.44 (9H, s), 1.24-1.11 (2H, m).

Step 11. 4-[(4-{[(tert-butoxycarbonyl)amino]methyl}piperidin-1-yl)methyl]tetrahydro-2H-pyran-4-carboxylic acid To a solution of Methyl 4-[(4-{[(tert-butoxycarbonyl)amino]methyl}piperidin-1-yl)methyl]tetrahydro-2H-pyran-4-carboxylate (6.47 g, 17.5 mmol, Step 10) in MeOH (32 mL), 5 N NaOH aq (10 mL) was added at room temperature (exothermic). The resulting solution was stirred at 60° C. for 7 h, then cooled to 5-10° C. in ice-cold bath. To this solution, 5 N HCl aq (10 mL) was added and the resulting solution (pH value was ca.6) was concentrated. To the residue, 2-propanol (80 mL) was added. This solution was concentrated. To the residue, 2-propanol (80 mL) was added and it was concentrated again. The residue was diluted with EtOH (80 mL) and the mixture was stirred at room temperature for 2 h. It was filtered through a celite pad (5.0 g) to remove NaCl. The Celite pad was washed with EtOH (20 mL) and the combined filtrate was concentrated. To the residue, CH$_3$CN (40 mL) was added and it was concentrated. During this procedure, the formation of white precipitate was noticed. To the residue CH$_3$CN (40 mL) was added and the resulting suspension was stirred at room temperature for 2 h. This mixture was filtered and obtained solid was washed with CH$_3$CN (10 mL), then dried under reduced pressure to give 4.1 g (65%) of the titled compound as white powder.

$^1$H NMR (300 MHz, CDCl$_3$) δ 4.66 (1H, m), 3.93-3.82 (3H, m), 3.15-2.99 (4H, m), 2.58 (2H, s), 2.58-2.45 (2H, m), 1.98-1.76 (4H, m), 1.55-1.35 (6H, m), 1.44 (9H, s) mp 129° C.

Step 12. 4-{[4-(aminomethyl)piperidin-1-yl]methyl}tetrahydro-2H-pyran-4-carboxylic acid 4-methylbenzenesulfonate In a 300 mL, 3-necked round bottom flask under N$_2$, 4-[(4-{[(tert-butoxycarbonyl)amino]methyl}piperidin-1-yl)methyl]tetrahydro-2H-pyran-4-carboxylic acid (10 g, 28 mmol, Step 11) was placed and a solution of p-TsOH H$_2$O (16 g, 84 mmol) in IPA (150 mL) was poured at room temperature. The resulting mixture was stirred at 60° C. for 7 h under N$_2$ and Et$_3$N (8.6 mL, 62 mmol) was added dropwise slowly during the period of 2 hr with seeding. The white precipitate was formed during the addition of Et$_3$N. The resulting white suspension was stirred at 60° C. for 3 h, at 50° C. for 5 h and at room temperature for 10 h. The suspension was filtered and the obtained solid was washed with IPA (100 mL), dried at 50° C. for 5 h to give 10.5 g (87%) of the titled compound as white powder.

$^1$H-NMR (D$_2$O) δ 7.54 (2H, d, J=7.4 Hz), 7.22 (2H, J=7.4 Hz), 3.80-3.65 (2H, m), 3.55-3.40 (4H, m), 3.20-2.75 (6H, m), 2.24 (3H, s), 1.90-1.80 (6H, m), 1.55-1.35 (4H, m) mp 247° C.

Step 13. 4-{[4-({[(3-Isopropyl-2-oxo-2,3-dihydro-1H-benzimidazol-1-yl)carbonyl]amino}methyl)piperidin-1-yl]methyl}tetrahydro-2H-pyran-4-carboxylic acid A mixture of 1-isopropyl-1,3-dihydro-2H-benzimidazol-2-one (1.0 g, 5.7 mmol) and chloroformic acid 4-nitrophenyl ester (1.14 g, 5.7 mmol) in CH$_2$Cl$_2$ (20 mL) was stirred at room temperature for 5 min under N$_2$. To this mixture, Et$_3$N (1.7 mL, 12.5 mmol) was added slowly and this generated mixture was added to a mixture of 4-{[4-(aminomethyl)piperidin-1-yl]methyl}tetrahydro-2H-pyran-4-carboxylic acid 4-methylbenzenesulfonate (2.4 g, 5.7 mmol, Step 12) in CH$_2$Cl$_2$ (15 mL) at rt. The resulting mixture was stirred at room temperature for 2 hrs. This mixture was washed with 0.5 N HCl aq (100 mL) and the organic layer was washed with saturated NaHCO$_3$ aq (75 ml) then the organic layer was concentrated. The residue was diluted with EtOAc (75 mL) and it was concentrated until ca 15 mL. After seeding of the product, this mixture was stirred at room temperature for 30 min. During this procedure, the solid was formed and this mixture was filtered: Obtained solid was washed with EtOAc (10 mL), dried at 50° C. under vacuum to give 1.9 g (73%) of the titled compound as white solid.

Step 14. 4-{[4-({[(3-isopropyl-2-oxo-2,3-dihydro-1H-benzimidazol-1-yl)carbonyl]amino}methyl)piperidin-1-yl]methyl}tetrahydro-2H-pyran-4-carboxylic acid benzenesulfonate To a suspension of 4-{[4-({[(3-Isopropyl-2-oxo-2,3-dihydro'-1H-benzimidazol-1-yl) carbonyl]amino}methyl)piperidin-1-yl]methyl}tetrahydro-2H-pyran-4-carboxylic acid (750 mg, Step 13) in CH$_3$CN (5 mL), a solution of benzenesulfonic acid monohydrate (288 mg) in CH$_3$CN (5 mL) was added at room temperature. The resulting mixture was stirred at room temperature for 2 days and it was concentrated. The residue was dried to afford 909 mg (90%) of the titled compound as a solid.

$^1$H-NMR (CD$_3$OD) δ 9.10 (1H, t, J=5.7 Hz), 8.11 (1H, dt, J=8.0, 0.8 Hz), 7.88-7.76 (2H, m), 7.46-7.36 (3 H, m), 7.32 (1H, dt, J=8.0, 0.8 Hz), 7.22 (1H, td, J=7.8, 1.4 Hz), 7.13 (1H, td, J=7.8, 1.4 Hz), 4.70 (1H, sextet, J=6.9 Hz), 3.85-3.55 (5H, m), 3.50-3.38 (4H, m), 3.23-3.05 (2H, m), 2.15-1.90 (5H, m), 1.78-1.58 (5H, m), 1,55 (6H, d, J=6.9 Hz) mp 223° C.

Anal. calcd. for C$_{30}$H$_{40}$N$_4$O$_8$S: C, 58.42; H, 6.54; N, 9.08: Found: C, 58.50; H, 6.51; N, 9.11.

PXRD (2θ(+/−0.1):5.3, 12.6, 21.4, 21.9)

Example 2

1-{[4-({[(3-isopropyl-2-oxo-2,3-dihydro-1H-benzimidazol-1-yl)carbonyl]amino}methyl)piperidin-1-yl]methyl}cyclohexanecarboxylic acid

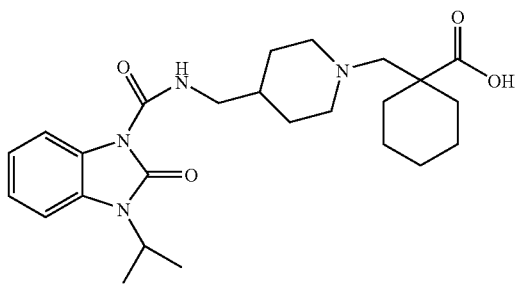

Step 1. tert-butyl 4-cyanocyclohexanecarboxylate

The title compound was prepared by a method similar to that shown in the Step 1 of Example 1 by using 1,5-dibromopentane.

$^1$H-NMR (CDCl$_3$) δ: 2.07 (2H, d, J=13.0 Hz), 1.85-1.57 (7H, m), 1.50 (9H, s), 1.35-1.15 (1H, m).

Step 2. tert-butyl 1-(aminomethyl)cyclohexanecarboxylate

The title compound was prepared by a method similar to that shown in the Step 2 of Example 1.

MS (ESI) m/z: 214 (M+H)$^+$.

$^1$H-NMR (CDCl$_3$) δ: 2.69 (2H, s), 2.02 (2H, d, J=13.2 Hz), 1.65-1.05 (19H, m, including 9H, s, 1.47 ppm).

Step 3. tert-butyl 1-[(4-oxopiperidin-1-yl)methyl] cyclohexanecarboxylate

The title compound was prepared by a method similar to that shown in the Step 3 of Example 1.

MS (ESI) m/z: 296 (M+H)$^+$.

$^1$H-NMR (CDCl$_3$) δ: 2.84 (4H, t, J=6.1 Hz) 2.57 (2H, s), 2.38 (4H, t, J=6.1 Hz), 2.04 (2H, d, J=12.2 Hz), 1.65-1.15 (17H, m, including 9H, s, 1.47 ppm).

Step 4. tert-butyl 1-[(4-cyanopiperidin-1-yl)methyl] cyclohexanecarboxylate

The title compound was prepared by a method similar to that shown in the Step 4 of Example 1.

MS (ESI) m/z: 307 (M+H)$^+$.

$^1$H-NMR (CDCl$_3$) δ: 2.53-2.66 (2H, m), 2.53-2.48 (1H, m), 2.48-2.30 (4H, m, including 2H, s, 2.41 ppm), 1.97 (2H, d, J=12.5 Hz), 1.92-1.70 (4H, m), 1.65-1.10 (19H, m, including 9H, s, 1.45 ppm).

Step 5. tert-butyl 1-{[4-(aminomethyl)piperidin-1-yl] methyl}cyclohexanecarboxylate The title compound was prepared by a method similar to that shown in the Step 5 of Example 1.

MS (ESI) m/z: 311 (M+H$^+$).

$^1$H-NMR (CDCl$_3$) δ: 2.81 (2H, d, J=11.37 Hz), 2.55 (2H, d, J=5.8 Hz), 2.39 (2H, s), 2.11 (2H, t, J=11.0 Hz), 2.03-1.85 (5H, m), 1.65-1.10 (21H, m, including 9H, s, 1.45 ppm).

Step 6. tert-butyl 1-{[4-({[(3-isopropyl-2-oxo-2,3-dihydro-1H-benzimidazol-1-yl)carbonyl] amino}methyl)piperidin-1-yl] methyl}cyclohexanecarboxylate The title compound was prepared by a method similar to that shown in the Step 6 of Example 1.

MS (ESI) m/z: 513 (M+H)$^+$.

$^1$H NMR (CDCl$_3$) δ 8.89 (1H, t, J=5.3 Hz), 8.33-8.20 (1H, m), 7.23-7.10 (3H, m), 4.80-4.60 (1H, m), 3.27 (2H, t, J=6.3 Hz), 2.82 (2H, d, J=11.5 Hz), 2.39 (2H, s), 2.12 (2H, t, J=11.4 Hz), 1.97 (2H, d, J=13.2 Hz), 1.73-1.10 (28H, m, including 6H, d, J=6.9 Hz, 1.56 ppm and 9H, s, 1.45 ppm).

Step 7. 1-{[4-({[(3-isopropyl-2-oxo-2,3-dihydro-1H-benzimidazol-1-yl)carbonyl]amino}methyl)piperidin-1-yl]methyl}cyclohexanecarboxylic acid The title compound was prepared by a method similar to that shown in the Step 7 of Example 1.

MS (ESI) m/z: 457 (M+H)$^+$.

$^1$H NMR (CDCl$_3$) δ 8.98 (1H, t, J=5.8 Hz), 8.28-8.18 (1H, m), 7.25-7.10 (3H, m), 4.80-4.60 (1H, m), 3.34 (2H, t, J=6.3 Hz), 3.11 (2H, d, J=11.9 Hz), 2.61 (2H, s), 2.48 (2H, t, J=12.2 Hz), 2.05-1.20 (21H, m, including 6H, d, J=6.9 Hz, 1.57 ppm).

m.p.: 151° C.

IR (KBr) v: 3291, 2930, 1732, 1690, 1545, 1481, 1373, 1298, 1202, 1134, 762 cm$^{-1}$.

Anal. calcd. for C$_{25}$H$_{36}$N$_4$O$_4$: C, 65.76; H, 7.95; N, 12.27. Found: C, 65.41; H, 8.18; N, 12.18.

Example 3

1-{[4-({[(3-isopropyl-2-oxo-2,3-dihydro-1H-benzimidazol-1-yl)carbonyl]amino}methyl)piperidin-1-yl]methyl}cyclopentanecarboxylic acid

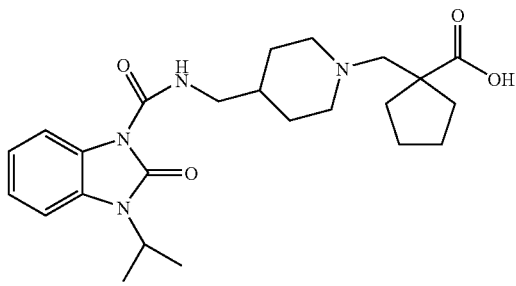

Step 1. Methyl 1-(iodomethyl)cyclopentanecarboxylate

To a stirred solution of HN(iPr)$_2$ (1.31 mL, 9.36 mmol) in THF (5 mL) was added n-BuLi (1.58 M in hexane, 5.43 mL, 8.58 mmol) with keeping −10° C. under N$_2$, and the mixture was stirred at −10° C. for 1 h. Then, to this mixture was added a solution of methyl cyclopentanecarboxylate (1.00 g, 7.80 mmol) in THF (3 mL) dropwise at 0° C., and the mixture was stirred at 0° C. for 2 h. Finally, to this mixture was added CH$_2$I$_2$ (0.628 mL, 7.80 mmol) at 0° C., and the resulting mixture was stirred at room temperature for 16 h. The reaction mixture was quenched with sat. NH$_4$Cl aq. (50 mL), extracted with Et$_2$O (75 mL) for two times, and the combined organic layer was washed with brine (75 mL). The organic layer was dried over Na$_2$SO$_4$, filtered and concentrated. Removal of the solvent gave a residue, which was chromatographed on a column of silica gel eluting with EtOAc/hexane (1:20→1:10) to give 1.085 g (52%) of title compound as a colorless oil.

$^1$H-NMR (CDCl$_3$) δ 3.73 (3H, s), 3.42 (2H, s), 2.30-2.15 (2H, m), 1.80-1.55 (6H, m).

Step 2. Methyl 1-[(4-{[(tert-butoxycarbonyl)amino]methyl}piperidine-1-yl)methyl]cyclopentanecarboxylate A mixture of Methyl 1-(iodomethyl)cyclopentanecarboxylate (5.52 g, 0.0206 mol, Step 1), tert-butyl (piperidin-4-ylmethyl)carbamate (8.83 g, 0.0412 mol) and iPr$_2$NEt (10.76 mL, 0.0618 mol) in N-methylpyrrolidone (70 mL) was stirred at 120° C. for 24 h. After cooling, the reaction mixture was diluted with sat. NaHCO$_3$ aq. (200 mL), extracted with AcOEt (200 mL) for three times, and the combined organic layer was washed with water (200 mL) and brine (200 mL). The organic layer was dried over Na$_2$SO$_4$, filtered and concentrated. Removal of the solvent gave a residue, which was chromatographed on a column of silica gel eluting with EtOAc/hexane (1:1) to give 4.91 g (67%) of title compound as a yellow syrup.

MS (ESI) m/z: 355(M+H)$^+$.

$^1$H-NMR (CDCl$_3$) δ 4.58 (1H, br s), 3.66 (3H, s), 2.97 (2H, t, J=6.3 Hz), 2.77 (2H, br d, J=11.5 Hz), 2.55 (2H, s), 1.70-1.50 (9H, m), 1.44 (9H, s), 1.25-1.08 (2H, m).

Step 3. Methyl 1-{[4-(aminomethyl)piperidin-1-yl]methyl}cyclopentanecarboxylate A solution of methyl 1-[(4-{[(tert-butoxycarbonyl)amino]methyl}piperidine-1-yl)methyl]cyclopentanecarboxylate (1.16 g, 3.27 mmol, Step 2) in CH$_2$Cl$_2$ (25 mL) and trifluoroacetic acid (5 mL) was stirred at room temperature for 1.5 h. The reaction mixture was then concentrated and basified with sat. NaHCO$_3$ aq. (100 mL), extracted with CHCl$_3$ (100 mL) for five times. The combined extract was dried and concentrated to give 0.831 g (100%) of title compound as yellow syrup.

MS (ESI) m/z: 255 (M+H)$^+$.

$^1$H-NMR (CDCl$_3$) δ 3.66 (3H, s), 2.78 (2H, d, J=11.5 Hz), 2.62-2.50 (4H, m), 2.15-1.98 (4H, m), 1.80-1.40 (9H, m), 1.30-1.05 (2H, m).

Step 4. Methyl 1-{[4-({[(3-isopropyl-2-oxo-2,3-dihydro-1H-benzimidazol-1-yl)carbonyl]amino}methyl)piperidin-1-yl]methyl}cyclopentanecarboxylate The title compound was prepared by a method similar to that shown in the Step 6 of Example 1.

MS (ESI) m/z: 457 (M+H)$^+$.

$^1$H NMR (CDCl$_3$) δ 8.94 (1H, t, J=5.7 Hz), 8.28-8.20 (7.25-7.10 (3H, m), 4.80-4.60 (1H, m), 3.66 (3H, s), 3.27 (2H, t, J=6.4 Hz), 2.84 (2H, d, J=11.6 Hz), 2.62 (2H, s), 2.20-2.00 (4H, m), 1.75-1.50 (15H, m, including 6H, d, J=7.0 Hz, 1.56 ppm), 1.40-1.20 (2H, m).

Step 5. 1-{[4-({[(3-isopropyl-2-oxo-2,3-dihydro-1H-benzimidazol-1-yl)carbonyl]amino}methyl)piperidin-1-yl]methyl}cyclopentanecarboxylic acid A mixture of Methyl 1-{[4-({[(3-isopropyl-2-oxo-2,3-dihydro-1H-benzimidazol-1-yl)carbonyl]amino}methyl)piperidin-1-yl]methyl}cyclopentanecarboxylate (1.33 g, 2.90 mmol, Step 4) in 4N—HCl (6 mL) and acetic acid (6 mL) was stirred at reflux for 18 h. After cooling, the reaction mixture was concentrated and basified with sat. NaHCO$_3$ aq. (100 mL), extracted with CH$_2$Cl$_2$ (150 mL) for three times. The combined extracts were dried over Na$_2$SO$_4$, filtered and concentrated. The residue was chromatographed on a column of silica gel eluted with MeOH/CH$_2$Cl$_2$ (1:10) to give 1.12 g (85%) of title compound as white solid. The crude compound was recrystallized from EtOAc×2 and dried in vacuo at 50° C. for 2 days to give 610 mg of title compound as white crystal.

MS (ESI) m/z: 443 (M+H)$^+$.

m.p.: 165° C.

IR (KBr) v: 3271, 2934, 1736, 1684, 1607, 1558, 1483, 1454, 1379, 1358, 1298, 1209, 1167, 1097, 758 cm$^{-1}$.

$^1$H NMR (CDCl$_3$) δ 9.00 (1H, t, J=5.5 Hz), 8.30-8.18 (1H, m), 7.25-7.10 (3H, m), 4.80-4.60 (1H, m), 3.34 (2H, t, J=11.0 Hz), 2.32-2.17 (2H, m), 2.00-1.30 (17H, m, including 6H, d, 7.0 Hz, 1.57 ppm).

Anal. calcd. for C$_{24}$H$_{34}$N$_4$O$_4$.0.2H$_2$O: C, 64.61; H, 7.77; N, 12.56. Found: C, 64.34; H, 7.79; N, 12.48.

Alternative route to synthesize 1-{[4-({[(3-Isopropyl-2-oxo-2,3-dihydro-1H-benzimidazol-1-yl)carbonyl]amino}methyl)piperidin-1-yl]methyl}cyclopentanecarboxylic acid is described below.

Step 6. Methyl 1-[(4-{[(tert-butoxycarbonyl)amino]methyl}piperidine-1-yl)methyl]cyclopentanecarboxylate The title compound was prepared according to the procedure described in the Step 10 of the Example 1 using [cyclopentylidene(methoxy)methoxy](trimethyl)silane (Synthesis, 1982, 1, 58-60) instead of [methoxy(tetrahydro-4H-pyran-4-ylidene)methoxy](trimethyl)silane.

MS (ESI) m/z: 355(M+H)⁺.

¹H-NMR (CDCl₃) δ 4.58 (1H, br s), 3.66 (3H, s), 2.97 (2H, t, J=6.3 Hz), 2.77 (2H, br d, J=11.5 Hz), 2.55 (2 H, s), 2.18-1.95 (4H, m), 1.70-1.50 (9H, m), 1.44 (9H, s), 1.25-1.08 (2H, m).

Step 7. 1-[(4-{[(tert-butoxycarbonyl)amino]methyl}piperidin-1-yl)methyl]cyclopentanecarboxylic acid To a solution of Methyl 1-[(4-{[(tert-butoxycarbonyl)amino]methyl}piperidin-1-yl)methyl]cyclopentanecarboxylate (2.8 g, 8.0 mmol, Step 6) in MeOH (11 mL), 2 N aqueous NaOH solution (6 mL) was added at room temperature (exothermic). The resulting solution was stirred at 70° C. for 4 h, then cooled to 5-10° C. in ice-cold water bath. To the solution, 5 N HCl aq (6 mL) was added dropwise. The resulting solution (pH value was ca.6) was concentrated and to the residue, 2-propanol (40 mL) was added. This solution was concentrated and to the residue, CH₃CN (40 mL) was added. The resulting mixture was stirred at room temperature for 2 h and it was filtered through a Celite pad (5.0 g) to remove NaCl. The filtrate was concentrated to give 2.4 g (quant) of the titled compound as white solid.

¹H NMR (300 MHz, DMSO-d6) δ 6.90-6.75 (1H, m), 2.95-2.80 (2H, m), 2.79 (2H, t, J=6.4 Hz), 2.58 (2H, s), 2.25-2.05 (2H, m), 2.05-1.85 (2H, m), 1.65-1.50 (6H, m), 1.50-1.25 (3H, m), 1.37 (9H, s), 1.20-0.95 (2H, m).

mp 150° C.

Step 8. 1-{[4-(aminomethyl)piperidin-1-yl]methyl}cyclopentanecarboxylic acid 4-methylbenzenesulfonate In a 100 mL, 2-necked round bottom flask, to a mixture of 1-[(4-{[(tert-butoxycarbonyl) amino]methyl}piperidin-1-yl)methyl]cyclopentanecarboxylic acid (5 g, 14.7 mmol, Step 7) in THF (25 mL), a solution of p-TsOH H₂O (8.4 g, 44 mmol) in THF (25 mL) was added at room temperature. The resulting mixture was stirred at 70° C. for 3 h under N₂ and it was cooled down to room temperature. To this solution, Et₃N (6 mL, 44 mmol) was added dropwise slowly. The white precipitate was formed during the addition of Et₃N and the resulting mixture was stirred at room temperature for 14 h. The suspension was filtered and the obtained solid was washed with THF (10 mL), dried at 50° C. for 5 h to give 5.9 g (97%) of the titled compound as a white solid.

¹H-NMR (D₂O) δ 7.51 (2H, J=8.2 Hz), 7.19 (2H, J=8.2 Hz), 3.38 (2H, d, J=11.0 Hz), 3.09 (2H, d, J=2.6 Hz), 2.88 (2H, t, J=12.1 Hz), 2.79 (2H, t, J=6.6 Hz), 2.21 (3H, s), 1.94-1.75 (5H, m), 1.61-1.27 (9H, m)

Step 9. 1-{[4-({[(3-Isopropyl-2-oxo-2,3-dihydro-1H-benzimidazol-1-yl)carbonyl]amino}methyl)piperidin-1-yl]methyl}cyclopentanecarboxylic acid A mixture of 1-isopropyl-1,3-dihydro-2H-benzimidazol-2-one (10 g, 56.8 mmol) and chloroformic acid 4-nitrophenyl ester (11.4 g, 56.8 mmol) in CH₂Cl₂ (150 mL) was stirred at room temperature for 5 min. To this mixture, Et₃N (17.4 mL, 125 mmol) was added slowly and the resulting mixture was added to a mixture of 1-{[4-(aminomethyl)piperidin-1-yl]methyl}cyclopentanecarboxylic acid 4-methylbenzene sulfonate (23.4 g, 56.8 mmol, Step 8) in CH₂Cl₂ (75 mL) at room temperature. After stirring for 10 min, Et₃N (7.9 mL, 56.8 mmol) was added and the resulting mixture was stirred at room temperature for 2 hr. This mixture was washed with 1 N HCl aq (100 mL). Organic layer was concentrated at 50° C. until ca 5 vol and it was replaced by acetone (50 mL×3) at 80° C. until ca 5 vol. To this mixture, H₂O (100 mL) was added at 80° C. and the resulting mixture was concentrated at 100° C. After cooling down to 50° C., 20% N,N-dimethylaminoethanol aqueous solution (100 mL) was added to this mixture and the solid was observed. The resulting mixture was cooled in ice cold bath and it was stirred for 18 hrs at that temperature. This mixture was filtered and the obtained solid was washed with H₂O (100 mL), dried at 50° C. under vacuum to afford 17.9 g (71%) of the titled compound as white solid.

mp. 166° C.

PXRD (2θ(+/−0.1): 4.4, 8.8, 13.2, 17.6)

Example 4

1-{[4-({[(3-isopropyl-2-oxo-2,3-dihydro-1H-benzimidazol-1-yl)carbonyl]amino}methyl)piperidin-1-yl]methyl}cyclopropanecarboxylic acid hydrochloride

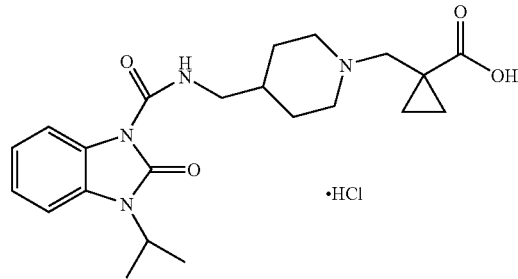

Step 1. tert-butyl 1-[(4-{[(tert-butoxycarbonyl)amino]methyl}piperidine-1-yl)methyl]cyclopropanecarboxylate Tert-butyl 1-(iodomethyl)cyclopropanecarboxylate (including starting material, 3:2 mixture) was prepared according to the procedure described of Step 1 in the Example 3 using tert-butyl cyclopropanecarboxylate (*J. Organomet. Chem.*, 1983, 252, 267-274) instead of methyl cyclopentanecarboxylate. This was used for the next step without further purification.

The title compound was prepared by a method similar to that shown in the Step 2 of Example 3.

MS (ESI) m/z: 369 (M+H)⁺.

¹H NMR (CDCl₃) δ 4.59 (1H, br s), 2.99 (2H, d, J=5.9 Hz), 2.89 (2H, br d, J=11.5 Hz), 2.57 (2H, s), 2.00 (2H, t, J=11.7 Hz), 1.62 (2H, d, J=12.9 Hz), 1.55-1.35 (1H, m), 1.44 (9H, s), 1.42 (9H, s), 1.30-1.15 (2H, m), 1.13 (2H, dd, J=3.8 Hz, 6.6 Hz), 0.74 (2H, dd, J=3.5 Hz, 6.3 Hz).

Step 2. tert-butyl 1-{[4-(aminomethyl)piperidin-1-yl]methyl}cyclopropanecarboxylate The title compound was prepared by a method similar to that shown in the Step 3 of Example 3.

MS (ESI) m/z: 269 (M+H)$^+$.

$^1$H NMR (CDCl$_3$) δ 2.96 (2H, br d, J=11.5 Hz), 2.60-2.50 (4H, m), 2.00 (2H, t, J=11.4 Hz), 1.75-1.35 (14H, m, including 2H, br d, J=9.6 Hz, 1.66 ppm and 9H, s, 1.43 ppm), 1.33-1.16 (2H, m), 1.13 (2H, dd, J=4.0 Hz, 6.9 Hz), 0.74 (2H, dd, J=3.8 Hz, 6.6 Hz).

Step 3. tert-butyl 1-{[4-({[(3-isopropyl-2-oxo-2,3-dihydro-1H-benzimidazol-1-yl)carbonyl]amino}methyl)piperidin-1-yl]methyl}cyclopropanecarboxylate The title compound was prepared by a method similar to that shown in the Step 4 of Example 3.

MS (ESI) m/z: 471 (M+H)$^+$.

$^1$H NMR (CDCl$_3$) δ 8.91 (1H, br t, J=5.5 Hz), 8.32-8.20 (1H, m), 7.25-7.10 (3H, m), 4.80-4.60 (1H, m), 3.30 (2H, t, J=6.4 Hz), 2.91 (2H, br d, J=11.6 Hz), 2.57 (2H, s), 2.01 (2H, br t, J=9.5 Hz), 1.73 (2H, br d, J=12.1 Hz), 1.67-1.50 (10H, m, including 6H, d, J=7.0 Hz, 1.56 ppm), 1.43 (9H, s), 1.34-1.20 (2H, m), 1.12 (2H, dd, J=4.0 Hz, 7.0 Hz), 0.73 (2H, dd, J=3.9 Hz, 6.8 Hz).

Step 4. 1-{[4-({[(3-isopropyl-2-oxo-2,3-dihydro-1H-benzimidazol-1-yl)carbonyl]amino}methyl)piperidin-1-yl]methyl}cyclopropanecarboxylic acid hydrochloride The title compound was prepared by a method similar to that shown in the Step 7 of Example 1.

MS (ESI) m/z: 415 (M+H)$^+$.

m.p.: 206° C.

IR (KBr) v: 2936, 2700, 1732, 1688, 1556, 1485, 1383, 1359, 1182, 1164, 758 cm$^{-1}$.

$^1$H NMR (DMSO-d$_6$) δ 8.86 (1H, t, J=6.3 Hz), 8.07 (1H, dd, J=1.0 Hz, 7.8 Hz), 7.45 (1H, d, J=7.1 Hz), 7.22 (1H, dt, J=1.3 Hz, 7.6 Hz), 7.15 (1H, dt, J=1.2 Hz, 7.7 Hz), 4.95-4.60 (1H, m), 3.70-3.10 (6H, m), 3.10-2.90 (2H, m), 1.86 (3H, m, including 2H, d, J=11.2 Hz, 1.86 ppm), 1.70-1.53 (2H, m), 1.49 (6H, d, J=6.9 Hz), 1.35-1.15 (4H, m).

Anal. calcd. for C$_{22}$H$_{30}$N$_4$O$_4$.HCl..0.2H$_2$O: C, 58.13; H, 6.96; N, 12.33. Found: C, 57.93; H, 6.97; N, 12.18.

Example 5

3-[4-({[(3-isopropyl-2-oxo-2,3-dihydro-1H-benzimidazol-1-yl)carbonyl]amino}methyl)piperidin-1-yl]propanoic acid hydrochloride

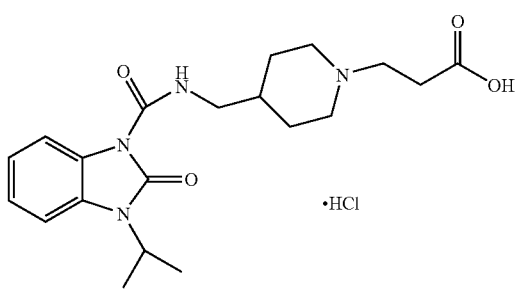

Step 1. tert-Butyl 4-({[(3-isopropyl-2-oxo-2,3-dihydro-1H-benzimidazol-1-yl)carbonyl]amino}methyl)piperidine-1-carboxylate To a stirred solution of 1-isopropyl-1,3-dihydro-2H-benzimidazol-2one (J. Med. Chem. 1999, 42, 2870-2880) (3.00 g, 17.02 mmol) and triethylamine (7.12 ml, 51.06 mmol) in 70 ml tetrahydrofuran was added triphosgene (5.15 g, 17.02 mmol) in 14 ml tetrahydrofuran at room temperature. The reaction mixture was refluxed for 19 hours. The mixture was then cooled to room temperature, tert-butyl 4-(aminomethyl)piperidine-1-carboxylate (J. Prugh, L. A. Birchenough and M. S. Egbertson, Synth. Commun., 1992, 22, 2357-60) (3.28 g, 15.32 mmol) in 10 ml tetrahydrofuran was added. The reaction mixture was refluxed for another 24 hours. Then cooled and basified with aqueous saturated NaHCO$_3$ 50 ml, and extracted with ethyl acetate 100 ml for three times. The combined extract was washed with brine, dried over MgSO$_4$ and concentrated. Flash chromatography of the residue (elutent: hexane/ethyl acetate=5/1 to 1/2) afforded a colorless oil 3.99 g (62%) as the titled compound.

$^1$H-NMR (CDCl$_3$) δ: 9.04-8.88 (1H, m), 8.83-8.20 (1H, m), 7.26-7.10 (3H, m), 4.80-4.60 (1H, m), 4.28-4.02 (2H, m), 3.32 (2H, t, J=6.1 Hz), 2.82-2.60 (2H, m), 1.94-1.10 (5H, m), 1.57 (6H, d, J=7.1 Hz), 1.45 (9H, s).

Step 2. 3-Isopropyl-2-oxo-N-(piperidin-4-ylmethyl)-2,3-dihydro-1H-benzimidazole-1-carboxamide A solution of tert-butyl 4-({[(3-isopropyl-2-oxo-2,3-dihydro-1H-benzimidazol-1-yl)carbonyl]amino}methyl)piperidine-1-carboxylate (3.992 g, 9.58 mmol) in 50 ml 10% hydrochloric acid in methanol and 10 ml concentrated hydrochloric acid was stirred at room temperature for 18 hours. The mixture was then concentrated and basified with aqueous Na$_2$CO$_3$, extracted with CHCl$_3$ (100 ml) for 3 times. The combined extract was dried and concentrated. Flash chromatography of the residue (NH-silica gel, elutent: CH$_2$Cl$_2$/methanol=100/1) afforded a colorless oil 2.272 g (75%) as the title compound.

MS (ESI) m/z: 317 (M+H)$^+$.

$^1$H-NMR (CDCl$_3$) δ: 8.93 ($^1$H, br), 8.32-8.22 (1H, m), 7.24-7.02 (3H, m), 4.80-4.61 (1H, m), 3.31 (2H, t, J=6.0 Hz), 3.20-3.05 (2H, m), 2.79-2.54 (2H, m), 1.84-1.52 (3H, m), 1.57 (6H, d, J=6.9 Hz), 1.36-1.13 (2H, m).

Step 3. tert-butyl 3-[4-({[(3-isopropyl-2-oxo-2,3-dihydro-1H-benzimidazol-1-yl)carbonyl]amino}methyl)piperidin-1-yl]propanoate A mixture of 3-isopropyl-2-oxo-N-(piperidin-4-ylmethyl)-2,3-dihydro-1H-benzimidazole-1-carboxamide (0.50 g, 1.58 mmol, Step 2), tert-butyl acrylate (0.340 mL, 2.37 mmol) and iPrNEt (0.275 mL, 2.37 mmol) in THF (20 mL) was refluxed for 18 h. After cooling, the reaction mixture was diluted with sat. NaHCO$_3$ aq. (100 mL), extracted with CH$_2$Cl$_2$ (100 mL) for three times. The combined extracts were dried over Na$_2$SO$_4$, filtered and concentrated. The residue was chromatographed on a column of silica gel eluted with MeOH/CH$_2$Cl$_2$ (1:20→1:10) and then NH-silica gel eluted with EtOAc/hexane (1:5→1:2) to give 0.111 g (16%) of title compound as colorless syrup.

MS (ESI) m/z: 445 (M+H)$^+$.

$^1$H NMR (CDCl$_3$) δ 8.94 (1H, br s), 8.30-8.20 (1H, m), 7.25-7.11 (3H, m), 7.11-7.00 (1H, m), 4.80-4.62 (1 H, m), 3.31 (2H, t, J=6.2 Hz), 2.95 (2H, br t, J=11.6 Hz), 2.68 (2H, t, J=7.2 Hz), 2.43 (2H, t, J=7.7 Hz), 2.03 (2H, br t, J=11.4 Hz), 1.98-1.82 (1H, m), 1.79 (2H, d, J=12.1 Hz), 1.56 (6H, d, J=7.2 Hz), 1.50-1.30 (11H, m, including 9H, s, 1.44 ppm).

Step 4. 3-[4-({[(3-isopropyl-2-oxo-2,3-dihydro-1H-benzimidazol-1-yl)carbonyl]amino}methyl)piperidin-1-yl]propanoic acid hydrochloride The title compound was prepared by a method similar to that shown in the Step 7 of Example 1.

MS (ESI) m/z: 389 (M+H)+.

IR (KBr) v: 2939, 2637, 1724, 1682, 1542, 1466, 1373, 1217, 1194, 953, 762 cm−1.

1H NMR (DMSO-d6) δ 8.86 (1H, t, J=5.9 Hz), 8.07 (1H, dd, J=0.8 Hz, 7.7 Hz), 7.49 (1H, d, J=7.6 Hz), 7.22 (1H, dt, J=1.3 Hz, 7.6 Hz), 7.15 (1H, dt, J=1.0 Hz, 7.6 Hz), 4.75-4.60 (1H, m), 3.70-3.10 (6H, m), 2.93 (2H, br t, J=11.2 Hz), 2.85-2.70 (2H, m), 1.95-1.75 (3H, m, including 2H, d, J=11.5 Hz, 1.87 ppm), 1.65-1.40 (8H, m, including 6H, d, J=7.1 Hz, 1.49 ppm).

Anal. calcd. for C20H28N4O4.HCl.0.8H2O: C, 54.68; H, 7.02; N, 12.75. Found: C, 54.67; H, 6.88; N, 12.70.

Example 6

1-{[4-hydroxy-4-({[(3-isopropyl-2-oxo-2,3-dihydro-1H-benzimidazol-1-yl)carbonyl]amino}methyl)piperidin-1-yl]methyl}cyclohexanecarboxylic acid

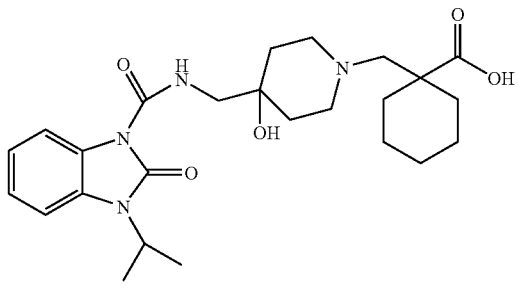

Step 1. methyl 1-(iodomethyl)cyclohexanecarboxylate

The title compound was prepared by a method similar to that shown in the Step 1 of Example 3 by using Methyl cyclohexanecarboxylate.

1H NMR (CDCl3) δ 3.73 (3H, s), 3.32 (2H, s), 2.20-2.05 (2H, m), 1.70-1.20 (8H, m).

Step 2. Methyl 1-[(4-{[(tert-butoxycarbonyl)amino]methyl}-4-hydroxypiperidine-1-yl)methyl]cyclohexanecarboxylate The title compound was prepared by a method similar to that shown in the Step 2 of Example 3 by using tert-butyl [(4-hydroxypiperidin-4-yl)methyl]carbamate (*Chem. Pharm. Bull.*, 2002, 50 (9) 1187-1194) and methyl 1-(iodomethyl)cyclohexanecarboxylate (Step 1 of Example 6).

MS (ESI) m/z: 385 (M+H)+.

1H NMR (CDCl3) δ 4.86 (1H, br s), 3.66 (3H, s), 3.11 (2H, d, J=6.3 Hz), 2.55-2.45 (6H, m), 2.03 (2H, br d, J=10.4 Hz), 1.70-1.15 (18H, m, including 9H, s, 1.44 ppm).

Step 3. Methyl 1-{[4-(aminomethyl)-4-hydroxypiperidin-1-yl]methyl}cyclohexanecarboxylate The title compound was prepared by a method similar to that shown in the Step 3 of Example 3.

MS (ESI) m/z: 285 (M+H)+.

1H NMR (CDCl3) δ 3.66 (3H, s), 2.61 (1H, br s), 2.57-2.45 (5H, m), 2.35-2.11 (3H, m), 2.04 (2H, br d, J=11.5 Hz), 1.65-1.45 (6H, m), 1.45-1.20 (4H, m).

Step 4. Methyl 1-{[4-hydroxy-4-({[(3-isopropyl-2-oxo-2,3-dihydro-1H-benzimidazol-1-yl)carbonyl]amino}methyl)piperidin-1-yl]methyl}cyclohexanecarboxylate The title compound was prepared by a method similar to that shown in the Step 4 of Example 3.

MS (ESI) m/z: 487 (M+H)+.

1H NMR (CDCl3) δ 9.12 (1H, t, J=5.6 Hz), 8.30-8.20 (1H, m), 7.25-7.10 (3H, m), 4.80-4.65 (1H, m), 3.66 (3H, s), 3.54 (2H, d, J=5.9 Hz), 2.60-2.45 (6H, m), 2.03 (2H, br d, J=9.1 Hz), 1.75-1.47 (12H, m), 1.47-1.15 (6H, m).

Step 5. 1-{[4-hydroxy-4-({[(3-isopropyl-2-oxo-2,3-dihydro-1H-benzimidazol-1-yl)carbonyl]amino}methyl) piperidin-1-yl]methyl}cyclohexanecarboxylic acid The title compound was prepared by a method similar to that shown in the Step 5 of Example 3.

MS (ESI) m/z: 473 (M+H)+.

m.p.: 184° C.

IR (KBr) v: 3437, 3273, 2943, 1732, 1688, 1601, 1533, 1479, 1452, 1371, 1134, 978, 762 cm−1.

1H NMR (DMSO-d6) δ 8.94 (1H, t, J=5.6 Hz), 8.09 (1H, d, J=7.7 Hz), 7.43 (1H, d, J=7.7 Hz), 7.22 (1H, t, J=7.8 Hz), 7.14 (1H, t, J=7.4 Hz), 4.75-4.58 (1H, m), 4.59 (1H, s), 2.47 (2H, s), 4.00-3.00 (6H, m), 1.86 (2H, d, J=11.4 Hz), 1.60-1.10 (18H, m, including 6H, d, J=6.9 Hz, 1.49 ppm).

Anal. calcd. for C25H36N4O5.0.5H2O: C, 62.35; H, 7.74; N, 11.63. Found: C, 62.52; H, 7.70; N, 11.66.

Example 7

1-{[4-({[(3-isopropyl-2-oxo-2,3-dihydro-1H-benzimidazol-1-yl)carbonyl]amino}methyl)piperidin-1-yl]methyl}cyclobutanecarboxylic acid

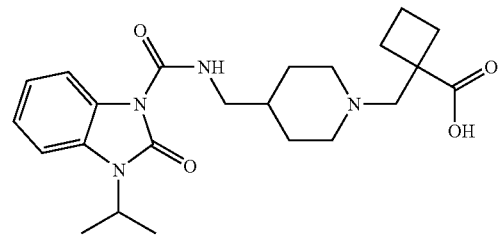

Step 1. methyl 1-[(4-{[(tert-butoxycarbonyl)amino]methyl}piperidin-1-yl)methyl]cyclobutanecarboxylate To a stirred mixture of tert-butyl (piperidin-4-ylmethyl)carbamate (12.8 g, 60 mmol) and methyl 1-formylcyclobutanecarboxylate (2.13 g, 15 mmol, Davis, Charles R.; Swenson, Dale C.; Burton, Donald J., *J. Org. Chem.*, 1993, 58, 6843) in tetrahydrofuran was added acetic acid (8.6 mL, 150 mmol) at ambient temperature. After 30 min, sodium triacetoxyborohydride (12.7 g, 60 mmol) was added to the mixture. Then, the mixture was heated to 60° C. for 2 h.

After cooling, the reaction mixture was poured into sat. $NaHCO_3$ aq. The aqueous layer was extracted with dichloromethane for 3 times. The combined organic phase was washed with brine, dried over $MgSO_4$ and concentrated. The residue was chromatographed on a column of silica gel eluting with hexane/ethyl acetate (1:1) to give 4.25 g (83%) of the title compound as a white solid.

MS (ESI) m/z: 341 (M+H)$^+$.

$^1$H-NMR (CDCl$_3$) δ: 3.69 (3H, s), 2.96 (2H, t, J=6.2 Hz), 2.75 (2H, d, J=11.4 Hz), 2.67 (2H, s), 2.37-2.46 (2H, m), 1.78-2.05 (6H, m), 1.45-1.65 (2H, m), 1.43 (9H, s), 1.09-1.21 (2H, m),

Step 2. methyl 1-{[4-(aminomethyl)piperidin-1-yl]methyl}cyclobutanecarboxylate The title compound was prepared according to the procedure described in Step 3 of Example 3 from methyl 1-[(4-{[(tert-butoxycarbonyl)amino]methyl}piperidin-1-yl)methyl]cyclobutanecarboxylate (step 1 of Example 7).

MS (ESI) m/z: 241 (M+H)$^+$.

$^1$H-NMR (CDCl$_3$) δ: 3.67 (3H, s), 2.72-2.78 (2H, m), 2.66 (2H, s), 2.54 (2H, d, J=6.2 Hz), 2.34-2.47 (2H, m), 1.79-2.04 (8H, m), 1.54-1.64 (2H, m), 1.05-1.35 (3H, m).

Step 3. Methyl 1-{[4-({[(3-isopropyl-2-oxo-2,3-dihydro-1H-benzimidazol-1-yl)carbonyl]amino}methyl)piperidin-1-yl]methylcyclobutanecarboxylate The title compound was prepared according to the procedure described in Step 6 of Example 1 from 1-isopropyl-1,3-dihydro-2H-benzimidazol-2-one and methyl 1-[(4-{[(tert-butoxycarbonyl)amino}methyl}piperidin-1-yl)methyl]cyclobutanecarboxylate (step 2 of Example 7).

$^1$H-NMR (CDCl$_3$) δ: 8.92-8.86 (1H, m), 8.28-8.24 (1H, m), 7.20-7.12 (3H, m), 4.75-4.62 (1H, m), 3.70 (3 H, s), 3.27 (2H, t, J=6.4 Hz), 2.85-2.72 (2H, m), 2.68 (2H, s), 2.47-2.35 (2H, m), 2.05-1.92 (4H, m), 1.92-1.76 (2H, m), 1.71-1.61 (2H, m), 1.56 (6H, d, J=7.0 Hz), 1.32-1.17 (2H, m),

MS (ESI) m/z: 443 (M+H)$^+$.

Step 4. 1-{[4-({[(3-isopropyl-2-oxo-2,3-dihydro-1H-benzimidazol-1-yl)carbonyl]amino}methyl)piperidin-1-yl]methyl}cyclobutanecarboxylic acid The title compound was prepared according to the procedure described in Step 5 of Example 3 from Methyl 1-{[4-({[(3-isopropyl-2-oxo-2,3-dihydro-1H-benzimidazol-1-yl)carbonyl]amino}methyl)piperidin-1-yl]methyl}cyclobutanecarboxylate (step 3 of Example 7).

IR (KBr) v: 3293, 2979, 2937, 2875, 1732, 1687, 1610, 1548, 1479, 1375, 1298, 1203, 1099, 761, 704 cm$^{-1}$ $^1$H-NMR (CDCl$_3$) δ: 9.02-8.95 (1H, m), 8.26-8.22 (1H, m), 7.22-7.12 (3H, m), 4.76-4.62 (1H, m), 3.33 (2 H, t, J=6.2 Hz), 3.10-3.00 (2H, m), 2.77 (2H, s), 2.58-2.48 (2H, m), 2.44-2.24 (2H, m), 1.92-1.79 (2H, s), 1.99-1.80 (5H, m), 1.56 (6H, d, J=7.0 Hz), 1.50-1.33 (3H, m).

MS (ESI) m/z: 429 (M+H)$^+$.

Anal. Calcd. for $C_{23}H_{32}N_4O_4$: C, 64.46; H, 7.53; N, 13.07. Found: C, 64.47; H, 7.43; N, 12.93.

Alternative route to synthesize 1-{[4-({[(3-Isopropyl-2-oxo-2,3-dihydro-1H-benzimidazol-1-yl)carbonyl]amino}methyl)piperidin-1-yl]methyl}cyclobutanecarboxylic acid is described below.

Step 5. Ethyl 1-[(4-{[(tert-butoxycarbonyl)amino]methyl}piperidin-1-yl)methyl]cyclobutanecarboxylate The title compound was prepared according to the procedure described in the Step 10 of the Example 1 using [cyclobutylidene(ethoxy)methoxy](trimethyl)silane (*Chem. Commun.*, 1971, 136-137) instead of [methoxy(tetrahydro-4H-pyran-4-ylidene)methoxy](trimethyl)silane.

MS (ESI) m/z: 355 (M+H)$^+$.

$^1$H-NMR (CDCl$_3$) 67 :4.55 (1H, br), 4.17 (2H, q, J=7.1 Hz), 2.96 (2H, t, J=6.3 Hz), 2.76 (2H, d, J=11.4 Hz), 2.48-2.33 (2H, m), 2.05-1.80 (6H, m), 1.43 (9H, s), 1.25 (3H, q, J=7.1 Hz), 1.40-1.05 (7H, m).

Step 6. 1-[(4-{[(tert-butoxycarbonyl)amino}methyl]piperidin-1-yl)methyl]cyclobutanecarboxylic acid A mixture of Ethyl 1-[(4-{[(tert-butoxycarbonyl)amino]methyl}piperidin-1-yl) methyl]cyclobutanecarboxylate (4.2 g, 11.9 mmol, Step 5), 2N NaOH (18 mL) and EtOH (12 mL) was heated at 50° C. for 4 hrs. The resulting solution was cooled in ice bath and 2N HCl (ca 19 mL) was added until pH of the mixture was ca 5-6. The whole was extracted with $CH_2Cl_2$/$^i$PrOH (3:1, 30 mL×3). Combined organic layer was dried ($Na_2SO_4$) and filtered. The filtrate was concentrated to give 3.8 g (98%) of the titled compound as yellow solid.

$^1$H NMR (300 MHz, CDCl$_3$) δ 4.08 (1H, m), 3.20-3.10 (2H, m), 3.08-2.99 (2H, m), 2.91 (2H, s), 2.60-2.38 (4H, m), 2.35-2.16 (2H, m), 2.05-1.76 (6H, m), 1.65 (1H, m), 1.44 (9H, s). mp 160° C.

Step 7. 1-{[4-(aminomethyl)piperidin-1-yl]methyl}cyclobutanecarboxylic acid 4-methylbenzenesulfonate In a 500 mL, 3-necked round bottom flask under $N_2$, a mixture of 1-[(4-{[(tert-butoxycarbonyl)amino]methyl}piperidin-1-yl)methyl]cyclobutane carboxylic acid (30 g, 92 mmol, Step 6) in THF (150 mL) was stirred at room temperature for 10 min. To this suspension, a solution of p-TsOH·H$_2$O (52.4 g, 276 mmol) in THF (150 mL) was added at room temperature. After stirring at that temp for 10 min, the resulting solution was heated under reflux condition for 3 hrs. After cooling down to room temperature, Et$_3$N (28.1 mL, 202 mmol) was added very slowly during the period of 1 h with seeding. The white precipitate was formed during the addition of Et$_3$N. The resulting white suspension was stirred at room temperature for 6 h and it was filtered and the obtained solid was washed with THF (100 mL×2), dried at 50° C. for 5 h to give 35 g (96%) of the titled compound as white powder $^1$H-NMR (D$_2$O) δ 7.40 (2H, d, J=7.2 Hz), 7.07 (2H, d, J=7.2 Hz), 3.28-3.00 (4H, m), 2.80-2.57 (4H, m), 2.09 (3H, s), 2.18-1.97 (2H, m), 1.85-1.58 (8H, m), 1.36-1.12 (2H, m)

mp: 210° C.

Step 8. 1-{[4-({[(3-Isopropyl-2-oxo-2,3-dihydro-1H-benzimidazol-1-yl)carbonyl]amino}methyl)piperidin-1-yl]methyl}cyclobutanecarboxylic acid A mixture of 1-isopropyl-1,3-dihydro-2H-benzimidazol-2-one (486 mg, 2.8 mmol) and chloroformic acid 4-nitrophenyl ester (556 mg, 2.8 mmol) in CH₂Cl₂ (10 mL) was stirred at room temperature for 5 min. To this mixture, Et₃N (0.84 mL, 6.1 mmol) was added slowly and this mixture became a solution. This solution was added to a mixture of 1-{[4-(aminomethyl)piperidin-1-yl]methyl}cyclobutanecarboxylic acid 4-methylbenzene sulfonate (1.1 g, 2.8 mmol, Step 7) in CH₂Cl₂ (5 mL) at room temperature. After stirring for 10 min, Et₃N (0.38 mL, 2.8 mmol) was added and the resulting mixture was stirred at room temperature for 2 hr. This mixture was washed with 0.5 N HCl aq (10 mL) and saturated NaHCO₃ aq (10 mL) then the organic layer was concentrated. To the residue, saturated NaHCO₃ aq (15 mL) and heptane (15 mL) was added at room temperature and it was stirred for 6 hrs at that temperature. Solid was observed and this mixture was filtered. The obtained solid was washed with H₂O and heptane. After drying, crude material was obtained (1.0 g, 82%) as white solid. This crude material (4.0 g) was purified by recrystallization from toluene (36 mL) to give 2.6 g of the titled compound (66%) as white solid.

mp. 173° C.

PXRD (2θ(+/−0.1): 10.8, 16.9, 18.9, 26.5)

Example 8

N-({1-(2-oxycarbonyl-2-methyl propyl)piperidin-4-yl}methyl)-3-isopropyl-2-oxo-2,3-dihydro-1H-benzimidazole-1-carboxamide

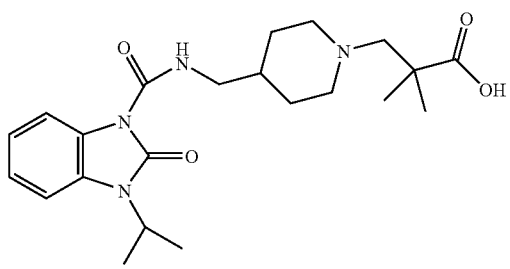

Step 1. tert-Butyl[{1-(2-benzyloxycarbonyl-2-methylpropyl)piperidin-4-yl}methyl]carbamate To a stirred solution of tert-butyl (piperidin-4-ylmethyl) carbamate (38.8 g, 181 mmol) in N,N-dimethylformamide (100 mL) was added benzyl 3-chloropivalate (14.2 g, 124 mmol, prepared from 3-chloropivaloyl chloride (25.6 g, 165 mmol) and benzyl alcohol (19.6 g, 181 mmol), ethyldiisopropylamine (64.0 g, 495 mmol) and sodium iodide (27.1 g, 181 mmol) at ambient temperature. The resulting mixture was stirred at 120° C. for 14 h. The volatile components were removed by evaporation and the resulting residue was chromatographed on a column of silica gel eluting with hexane/ethyl acetate (1:1) to give 640 mg (1%) of the title compound as a pale yellow oil.

MS (ESI) m/z: 405 (M+H⁺).

¹H NMR (CDCl₃) δ 7.43-7.23 (5H, m), 5.10 (2H, s), 4.58 (1H, br t), 2.95 (2H, m), 2.71 (2H, m), 2.46 (2H, brs), 2.06 (2H, m), 1.57-1.36 (3H, m), 1.44 (9H, s), 1.12 (2H, m), 1.17 (6H, s).

Step 2. N-({1-(2-benzyloxycarbonyl-2-methylpropyl)piperidin-4-yl}methyl)-3-isopropyl-2-oxo-2,3-dihydro-1H-benzimidazole-1-carboxamide To a stirred mixture of 1-isopropyl-1,3-dihydro-2H-benzimidazol-2-one (*J. Med. Chem.* 1999, 42, 2870-2880) (411 mg, 2.33 mmol) and triethylamine (1.00 mL, 7.17 mmol) in dichloromethane (20.0 mL) was added 4-nitrophenyl chloroformate (470 mg, 2.33 mmol) at room temperature. The resulting mixture was stirred for 2 h at room temperature. To the mixture was added a suspension of 1-(2-benzyloxycarbonyl-2-methylpropyl)-4-aminomethylpiperidine hydrochloride [prepared from concentration of a mixture of tert-butyl [{1-(2-benzyloxycarbonyl-2-methylpropyl)piperidin-4-yl}methyl]carbamate (step 1 of Example 1) (640 mg, 1.49 mmol) and 10% HCl in MeOH (20.0 mL)] and triethylamine (1.00 mL, 7.17 mmol) in dichloromethane (5.00 mL). The resulting mixture was stirred for 13 h at room temperature and 0.5 M NaOH aq. was added to the mixture. The mixture was extracted with dichloromethane. The extracts were washed with 0.5 M NaOH aq. and brine, dried over MgSO₄ and concentrated in vacuo. The residue was purified by preparative thin layer chromatography (silica gel, eluting with dichloromethane/methanol (10:1)) to give 508 mg (63%) of the title compound as a pale yellow oil.

MS (ESI) m/z: 507 (M+H⁺).

¹H NMR (CDCl₃) δ 8.89 (1H, br t, J=5.7 Hz), 8.26 (1H, m), 7.43-7.05 (8H, m), 5.10 (2H, s), 4.70 (1H, septet, J=7.0 Hz), 3.26 (2H, m), 2.75 (2H, m), 2.48 (2H, br s), 2.11 (2H, m), 1.61 (2H, m), 1.56 (6H, d, J=7.0 Hz), 1.52 (1H, m), 1.26 (2H, m), 1.18 (6H, s).

Step 3. N-([1-(2-oxycarbonyl-2-methylpropyl)piperidin-4-yl]methyl)-3-isopropyl-2-oxo-2,3-dihydro-1H-benzimidazole-1-carboxamide A mixture of N-({1-(2-benzyloxycarbonyl-2-methylpropyl)piperidin-4-yl]methyl)-3-isopropyl-2-oxo-2,3-dihydro-1H-benzimidazole-1-carboxamide (step 2 of Example z) (418 mg, 0.825 mmol) and 20% Pd(OH)₂/C (58.0 mg) in methanol (80 mL) was stirred under an atmosphere of hydrogen gas at room temperature for 12 h. The catalyst was filtered off on a pad of Celite, and the filtrate was evaporated under reduced pressure. Recrystallization of the resulting solid with hexane-CH₂Cl₂ afforded a colorless solid 285 mg (84%) as the titled compound.

MS (ESI) m/z: 417 (M+H)⁺.

¹H NMR (DMSO-d₆) δ 8.80 (1H, br t, J=5.8 Hz), 8.05 (1H, m), 7.42 (1H, m), 7.20 (1H, m), 7.12 (1H, m), 4.65 (1H, septet, J=7.0 Hz), 3.20 (2H, m), 2.85 (2H, m), 2.44 (2H, br s), 2.18 (2H, m), 1.61 (2H, m), 1.50 (1H, m), 1.47 (6H, d, J=7.0 Hz), 1.20 (2H, m), 1.04 (6H, s). The signal which correspond to carboxylic acid was not observed.

Anal. calcd. for C₂₂H₃₂N₄O₄.0.1 H₂O: C, 63.17; H, 7.76; N, 13.39. Found: C, 62.78; H, 7.74; N, 13.11.

Example 9

N-({1-(2-tetrazole-2-methylpropyl)piperidin-4-yl}methyl)-3-isopropyl-2-oxo-2,3-dihydro-1H-benzimidazole-1-carboxamide

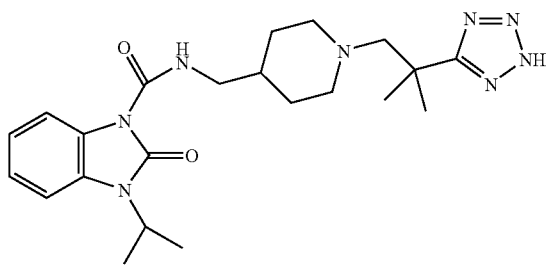

Step 1. 2-benzyl-α,α-dimethyl-2H-tetrazole-5-acetic acid, ethyl ester

To a stirred mixture of α,α-dimethyltetrazole-5-acetic acid, ethyl ester (*J. Med. Chem.* 1996, 39, 2354-2366.) (6.87 g, 37.3 mmol) and K$_2$CO$_3$ (12.3 g, 89.0 mmol) in acetone (200 mL) was added benzyl bromide (4.45 mL, 37.4 mmol) at ambient temperature. The resulting mixture was stirred at 50° C. for 18 h and concentrated under reduced pressure. The resulting residue was chromatographed on a column of silica gel eluting with hexane/ethyl acetate (10:1) to give 6.14 g (60%) of the title compound as a colorless oil.

MS (ESI) m/z: 275 (M+H$^+$).

$^1$H NMR (CDCl$_3$) δ 7.45-7.23 (5H, m), 5.73 (2H, s), 4.11 (2H, q, J=7.2 Hz), 1.70 (6H, s), 1.13 (3H, t, J=7.2 Hz).

Step 2. 2-benzyl-α,α-dimethyl-2H-tetrazole-5-acetaldehyde

To a stirred mixture of 2-benzyl-α,α-dimethyl-2H-tetrazole-5-acetic acid, ethyl ester acetaldehyde (step 1 of Example 9) (6.14 g, 22.4 mmol) in dichloromethane (100 mL) at –78° C. was added DIBAL (1.0 M in toluene, 50.0 mL, 50.0 mmol). The resulting mixture was stirred at –78° C. for 4 h. To the reaction mixture was added DIBAL (1.0 M in toluene, 25.0 mL, 25.0 mmol) and the resulting mixture was stirred at –78° C. for 8 h. To the mixture were added 2 M aqueous HCl (100 mL) and saturated aqueous NH$_4$Cl (20 mL). The organic layer was separated, dried over magnesium sulfate, and concentrated under reduced pressure. The resulting residue was chromatographed on a column of silica gel eluting with hexane/ethyl acetate (10:1) to give 3.45 g (67%) of the title compound as a colorless oil.

MS (ESI) m/z: 231 (M+H$^+$).

$^1$H NMR (CDCl$_3$) δ 9.68 (1H, s), 7.45-7.23 (5H, m), 5.74 (2H, s), 1.56 (6H, s).

Step 3. tert-Butyl [{1-(2-(2-benzyltetrazole)-2-methylpropyl)piperidin-4-yl}methyl]carbamate To a stirred solution of 2-benzyl-α,α-dimethyl-2H-tetrazole-5-acetaldehyde (step 2 of Example 9) (1.28 g, 5.56 mmol) and tert-butyl (piperidin-4-ylmethyl)carbamate (2.40 g, 11.2 mmol) in tetrahyrdofuran (300 mL) were added NaBH(OAc)$_3$ (5.90 g, 27.8 mmol) and AcOH (1.67 g, 27.8 mmol). The resulting mixture was stirred at 60° C. for 9 h and concentrated under reduced pressure. To the stirred residual oil and solid were added saturated aqueous NaHCO$_3$ and dichloromethane. The organic layer was separated, dried over magnesium sulfate, and concentrated under reduced pressure. The resulting residue was chromatographed on a column of silica gel eluting with hexane/ethyl acetate (1:1) to give 830 mg (35%) of the title compound as a colorless oil.

MS (ESI) m/z: 429 (M+H)$^+$.

$^1$H NMR (CDCl$_3$) δ 7.43-7.23 (5H, m), 5.72 (2H, s), 4.50 (1H, br t), 2.91 (2H, m), 2.58 (2H, br s), 2.49 (2 H, m), 2.05 (2H, m), 1.68-1.14 (3H, m), 1.44 (9H, s), 1.38 (6H, s), 1.00 (2H, m).

Step 4. N-([1-(2-(2-benzyltetrazole)-2-methylpropyl)piperidin-4-yl]methyl)-3-isopropyl-2-oxo-2,3-dihydro-1H-benzimidazole-1-carboxamide The title compound was prepared according to the procedure described in step 2 of Example 8 from 1-isopropyl-1,3-dihydro-2H-benzimidazol-2-one and tert-Butyl [{1-(2-(2-benzyltetrazole)-2-methylpropyl)piperidin-4-yl}methyl]carbamate (step 3 of Example 9).

MS (ESI) m/z: 531 (M+H$^+$).

$^1$H NMR (CDCl$_3$) δ 8.86 (1H, br t, J=5.7 Hz), 8.26 (1H, m), 7.43-7.08 (8H, m), 5.72 (2H, s), 4.70 (1H, septet, J=7.0 Hz), 3.21 (2H, m), 2.59 (2H, br s), 2.51 (2H, m), 2.07 (2H, m), 1.65-1.32 (3H, m), 1.56 (6 H, d, J=7.0 Hz), 1.38 (6H, s), 1.10 (2H, m).

Step 5. N-({1-(2-methyl-2-tetrazolepropyl)piperidin-4-yl}methyl)-3-isopropyl-2-oxo-2,3-dihydro-1H-benzimidazole-1-carboxamide The title compound was prepared according to the procedure described in Step 3 of Example 8 from N-({1-(2-(2-benzyltetrazole)-2-methylpropyl)piperidin-4-ylmethyl)-3-isopropyl-2-oxo-2,3-dihydro-1H-benzimidazole-1-carboxamide (step 4 of Example 9).

MS (ESI) m/z: 441 (M+H)$^+$.

$^1$H NMR (DMSO-d$_6$) δ 8.77 (1H, br t, J=5.9 Hz), 8.04 (1H, m), 7.40 (1H, m), 7.18 (1H, m), 7.11 (1H, m), 4.63 (1H, septet, J=7.0 Hz), 3.15 (2H, m), 2.54 (2H, br s), 2.43 (2H, m), 2.10 (2H, m), 1.60-1.25 (3H, m), 1.45 (6H, d, J=7.0 Hz), 1.32 (6H, s), 1.14 (2H, m). The signal which correspond to tetrazole was not observed.

Anal. calcd. for C$_{22}$H$_{32}$N$_8$O$_4$·0.95 H$_2$O: C, 57.74; H, 7.47; N, 24.48. Found: C, 58.03; H, 7.43; N, 24.10.

Example 10

N-([1-(2-cyclopentyl-2-tetrazoleethyl)piperidin-4-yl]methyl)-3-isopropyl-2-oxo-2,3-dihydro-1H-benzimidazole-1-carboxamide

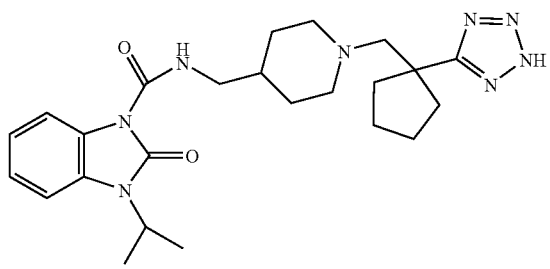

Step 1. α-cyclopentyltetrazole-5-acetic acid, ethyl ester

To a stirred solution of 1-cyano-1-cyclopentanecarboxylic acid, ethyl ester (*Bioorg. Med. Chem. Lett.* 1999, 9, 369-374.) (6.19 g, 37.0 mmol) in 1,4-dioxane (100 mL) was added $^n$Bu$_3$SnN$_3$ (12.3 g, 37.0 mmol) at ambient temperature. The resulting mixture was refluxed for 15 h and concentrated under reduced pressure. To the resulting residue was added 4 M HCl in 1,4-dioxane (50 mL) and concentrated under reduced pressure. The resulting oil was washed twice with hexane to give crude product of the title compound as a yellow oil, which was used for the next step without further purification.

Step 2. 2-benzyl-α-cyclopentyl-2H-tetrazole-5-acetic acid, ethyl ester

The title compound was prepared according to the procedure described in Step 1 of Example 9 from α-cyclopentyltetrazole-5-acetic acid, ethyl ester (step 1 of Example 10).

MS (ESI) m/z: 301 (M+H$^+$).

$^1$H NMR (CDCl$_3$) δ 7.45-7.23 (5H, m), 5.73 (2H, s), 4.11 (2H, q, J=7.1 Hz), 2.55-2.35 (4H, m), 1.88-1.56 (4H, m), 1.12 (3H, t, J=7.1 Hz).

Step 3. 2-benzyl-α-cyclopentyl-2H-tetrazole-5-acetaldehyde

The title compound was prepared according to the procedure described in Step 2 of Example 9 from 2-benzyl-α-cyclopentyl-2H-tetrazole-5-acetic acid, ethyl ester (step 2 of Example 10).

MS (ESI) m/z: 257 (M+H$^+$).

$^1$H NMR (CDCl$_3$) δ 9.71 (1H, s), 7.50-7.30 (5H, m), 5.74 (2H, s), 2.45-2.18 (4H, m), 1.85-1.66 (4H, m).

Step 4. tert-Butyl [{1-(2-(2-benzyltetrazole)-2-cyclopentylethyl)piperidin-4-yl}methyl]carbamate The title compound was prepared according to the procedure described in Step 3 of Example 9 from 2-benzyl-α-cyclopentyl-2H-tetrazole-5-acetaldehyde (step 3 of Example 10).

MS (ESI) m/z: 455 (M+H$^+$).

$^1$H NMR (CDCl$_3$) δ 7.43-7.23 (5H, m), 5.72 (2H, s), 4.67 (1H, br t), 2.88 (2H, m), 2.66 (2H, br s), 2.48 (2 H, m), 2.24 (2H, m), 1.93 (2H, m), 1.83 (2H, m), 1.78-1.48 (4H, m), 1.43 (9H, s), 1.37 (2H, m), 1.23 (1H, m), 0.94 (2H, m).

Step 5. N-({1-(2-(2-benzyltetrazole)-2-cyclopentylethyl)piperidin-4-yl}methyl)-3-isopropyl-2-oxo-2,3-dihydro-1H-benzimidazole-1-carboxamide The title compound was prepared according to the procedure described in step 2 of Example 8 from 1-isopropyl-1,3-dihydro-2H-benzimidazol-2-one and tert-Butyl [{1-(2-(2-benzyltetrazole)-2-cyclopentylethyl)piperidin-4-yl}methyl]carbamate (step 4 of Example 10).

MS (ESI) m/z: 557 (M+H$^+$).

$^1$H NMR (CDCl$_3$) δ 8.85 (1H, br t, J=5.5 Hz), 8.26 (1H, m), 7.43-7.08 (8H, m), 5.73 (2H, s), 4.70 (1H, septet, J=7.0 Hz), 3.19 (2H, m), 2.70 (2H, br s), 2.53 (2H, m), 2.25 (2H, m), 2.15-1.35 (11H, m), 1.56 (6 H, d, J=7.0 Hz), 1.07 (2H, m).

Step 6. N-({1-(2-cyclopentyl-2-tetrazoleethyl)piperidin-4-yl}methyl)-3-isopropyl-2-oxo-2,3-dihydro-1H-benzimidazole-1-carboxamide The title compound was prepared according to the procedure described in Step 3 of Example 8 from N-({1-(2-(2-benzyltetrazole)-2-cyclopentylethyl)piperidin-4-yl}methyl)-3-isopropyl-2-oxo-2,3-dihydro-1H-benzimidazole-1-carboxamide (step 5 of Example 10).

MS (ESI) m/z: 467 (M+H)$^+$.

$^1$H NMR (DMSO-d$_6$) δ 8.76 (1H, br t, J=5.9 Hz), 8.04 (1H, m), 7.40 (1H, m), 7.18 (1H, m), 7.11 (1H, m), 4.64 (1H, septet, J=7.0 Hz), 3.14 (2H, m), 2.63 (2H, br s), 2.54 (2H, m), 2.08 (2H, m), 2.00 (2H, m), 1.76 (2H, m), 1.68-0.96 (9H, m), 1.46 (6H, d, J=7.0 Hz). The signal which correspond to tetrazole was not observed.

Anal. calcd. for C$_{24}$H$_{34}$N$_8$O$_4$·1.0 H$_2$O·0.5 CH$_2$Cl$_2$: C, 55.83; H, 7.08; N, 21.26. Found: C, 55.71; H, 7.48; N, 20.86.

Example 11

N-({1-(2-cyclohexyl-2-tetrazoleethyl)piperidin-4-yl}methyl)-3-isopropyl-2-oxo-2,3-dihydro-1H-benzimidazole-1-carboxamide

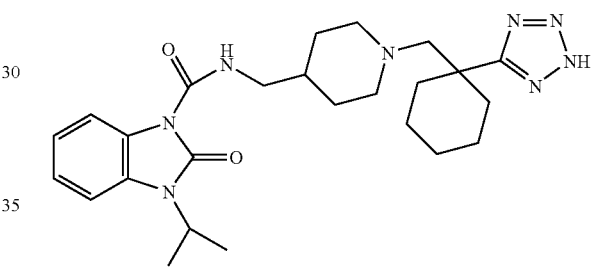

Step 1. α-cyclohexyltetrazole-5-acetic acid, ethyl ester

The title compound was prepared according to the procedure described in Step 1 of Example 10 from 1-cyano-1-cyclohexanecarboxylic acid, ethyl ester (*Bioorg. Med. Chem. Lett.* 1999, 9, 369-374.).

Step 2. 2-benzyl-α-cyclohexyl-2H-tetrazole-5-acetic acid, ethyl ester

The title compound was prepared according to the procedure described in Step 1 of Example 9 from α-cyclohexyltetrazole-5-acetic acid, ethyl ester (step 1 of Example 11).

MS (ESI) m/z: 315 (M+H$^+$).

$^1$H NMR (CDCl$_3$) δ 7.45-7.23 (5H, m), 5.75 (2H, s), 4.11 (2H, q, J=7.1 Hz), 2.36-2.16 (4H, m), 1.70-1.44 (6H, m), 1.12 (3H, t, J=7.1 Hz).

Step 3. 2-benzyl-α-cyclohexyl-2H-tetrazole-5-acetaldehyde

The title compound was prepared according to the procedure described in Step 2 of Example 9 from 2-benzyl-α-cyclohexyl-2H-tetrazole-5-acetic acid, ethyl ester (step 2 of Example 11).

MS (ESI) m/z: 271 (M+H$^+$).

¹H NMR (CDCl₃) δ 9.55 (1H, s), 7.45-7.25 (5H, m), 5.75 (2H, s), 2.34-2.16 (2H, m), 2.14-1.94 (2H, m), 1.70-1.32 (6H, m).

Step 4. tert-Butyl [{1-(2-(2-benzyltetrazole)-2-cyclohexylethyl)piperidin-4-yl}methyl]carbamate The title compound was prepared according to the procedure described in Step 3 of Example 9 from 2-benzyl-α-cyclohexyl-2H-tetrazole-5-acetaldehyde (step 3 of Example 11).

MS (ESI) m/z: 469 (M+H)⁺.

¹H NMR (CDCl₃) δ 7.43-7.23 (5H, m), 5.74 (2H, s), 4.55 (1H, br t), 2.87 (2H, m), 2.62-1.05 (17H, m), 2.49 (2H, br s), 1.43 (9H, s), 0.93 (2H, m).

Step 5. N-({1-(2-(2-benzyltetrazole)-2-cyclohexylethyl)piperidin-4-yl}methyl)-3-isopropyl-2-oxo-2,3-dihydro-1H-benzimidazole-1-carboxamide The title compound was prepared according to the procedure described in step 2 of Example 8 from 1-isopropyl-1,3-dihydro-2H-benzimidazol-2-one and tert-Butyl [{1-(2-(2-benzyltetrazole)-2-cyclohexylethyl)piperidin-4-yl}methyl]carbamate (step 4 of Example 11).

MS (ESI) m/z: 571 (M+H)⁺.

¹H NMR (CDCl₃) δ 8.86 (1H, br t, J=5.7 Hz), 8.26 (1H, m), 7.43-7.08 (8H, m), 5.73 (2H, s), 4.70 (1H, septet, J=7.0 Hz), 3.18 (2H, m), 2.51 (2H, br s), 2.45-1.15 (17H, m), 1.56 (6H, d, J=7.0 Hz), 1.04 (2H, m).

Step 6. N-({1-(2-cyclohexyl-2-tetrazoleethyl)piperidin-4-yl}methyl)-3-isopropyl-2-oxo-2,3-dihydro-1H-benzimidazole-1-carboxamide The title compound was prepared according to the procedure described in Step 3 of Example 8 from N-({-(2-(2-benzyltetrazole)-2-cyclohexylethyl)piperidin-4-yl}methyl)-3-isopropyl-2-oxo-2,3-dihydro-1H-benzimidazole-1-carboxamide (step 5 of Example 11).

MS (ESI) m/z: 481 (M+H)⁺.

¹H NMR (DMSO-d₆) δ 8.76 (1H, br t, J=5.9 Hz), 8.04 (1H, m), 7.41 (1H, m), 7.18 (1H, m), 7.12 (1H, m), 4.64 (1H, septet, J=7.0 Hz), 3.14 (2H, m), 2.38 (2H, br s), 2.33-2.10 (4H, m), 1.98 (2H, m), 1.65-0.96 (13H, m), 1.46 (6H, d, J=7.0 Hz). The signal which correspond to tetrazole was not observed.

Example 12

1-[4-({[(3-isopropyl-2-oxo-2,3-dihydro-1H-benzimidazol-1-yl)carbonyl]amino}methyl)piperidin-1-yl]cyclohexanecarboxylic acid hydrochloride

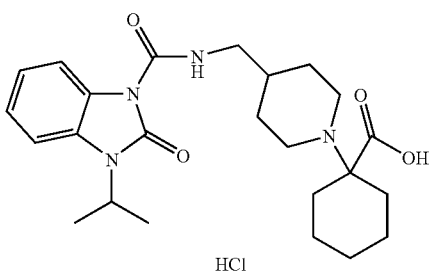

Step 1. tert-butyl 1-(4-oxopiperidin-1-yl)cyclohexanecarboxylate

The title compound was prepared by a method similar to that shown in the Step 3 of Example 1 by using tert-butyl 1-aminocyclohexanecarboxylate (Kenner et al., *J. Chem. Soc.*, 1965, 6239,6243.).

MS (ESI) m/z: 282 (M+H⁺).

¹H-NMR (CDCl₃) δ: 2.92 (4H, t, J=5.9 Hz), 2.41 (4H, t, J=6.0 Hz), 2.01-1.89 (2H, m), 1.76-1.62 (4H, m), 1.45 (9H, s), 1.53-1.33 (4H, m).

Step 2. tert-butyl 1-(4-cyanopiperidin-1-yl)cyclohexanecarboxylate

The title compound was prepared by a method similar to that shown in the Step 4 of Example 1 by using tert-butyl 1-(4-oxopiperidin-1-yl)cyclohexanecarboxylate.

MS (ESI) m/z: 293 (M+H⁺).

¹H-NMR (CDCl₃) δ: 2.94-2.85 (2H, m), 2.67-2.56 (1H, m), 2.55-2.42 (2H, m), 1.96-1.72 (6H, m), 1.70-1.23 (8H, m), 1.48 (9H, s).

Step 3. tert-butyl 1-[4-(aminomethyl)piperidin-1-yl]cyclohexanecarboxylate

The title compound was prepared by a method similar to that shown in the Step 5 of Example 1 by using tert-butyl 1-(4-cyanopiperidin-1-yl)cyclohexanecarboxylate.

¹H-NMR (CDCl₃) δ: 3.07-3.18 (2H, m), 2.55 (2H, d, J=6.4 Hz), 2.15-1.94 (4H, m), 1.47 (9H, s), 1.76-1.19 (13H, m), 1.19-1.03 (2H, m).

MS (ESI) m/z: 297 (M+H⁺).

Step 4. tert-butyl 1-[4-({[(3-isopropyl-2-oxo-2,3-dihydro-1H-benzimidazol-1-yl)carbonyl]amino}methyl)piperidin-1-yl]cyclohexanecarboxylate The title compound was prepared by a method similar to that shown in the Step 6 of Example 1 by using 1-isopropyl-1,3-dihydro-2H-benzimidazol-2-one and tert-butyl 1-(4-cyanopiperidin-1-yl)cyclohexanecarboxylate.

¹H-NMR (CDCl₃) δ: 8.97-8.86 (1H, m), 8.29-8.24 (1H, m), 7.21-7.11 (3H, m), 4.78-4.64 (1H, m), 3.29 (2 H, t, J=6.2 Hz), 3.19-3.09 (2H, m), 2.16-2.05 (2H, m), 2.04-1.93 (2H, m), 1.83-1.73 (2H, m), 1.56 (6H, d, J=7.0 Hz), 1.46 (9H, s), 1.70-1.39 (2H, m), 1.38-1.16 (7H, m).

MS (ESI) m/z: 499 (M+H⁺).

Step 5. 1-[4-({[(3-isopropyl-2-oxo-2,3-dihydro-1H-benzimidazol-1-yl)carbonyl]amino}methyl)piperidin-1-yl]cyclohexanecarboxylic acid hydrochloride To a stirred solution of tert-butyl 1-[4-({[(3-isopropyl-2-oxo-2,3-dihydro-1H-benzimidazol-1-yl)carbonyl]amino}methyl)piperidin-1-yl]cyclohexanecarboxylate (400 mg, 0.802 mmol) in dichloromethane (5 mL) was added trifluoroacetic acid (5 mL, 65.2 mmol) at room temperature. After 12 h, the volatile components were removed under reduced pressure. To the residue was added 4N HCl in dioxane (5.0 mL) was added and stirred for 10 min. Then, the volatile was removed under reduced pressure.

The residue was precipitated in diethylether/ethanol to give 370 mg of the titled compound as a colorless powder.

¹H-NMR (DMSO-d₆) δ: 8.94-8.82 (1H, m), 7.45 (1H, d, J=7.9 Hz), 7.27-7.10 (2H, m), 4.73-4.61 (1H, m), 3.71-3.19

(7H, m), 2.98-2.81 (2H, m), 2.38-2.26 (2H, m), 1.98-1.53 (10H, m), 1.49 (6H, d, J=7.0 Hz), 1.38-1.03 (2H, m),
MS (ESI) m/z: 443 (M+H$^+$).
Anal. Calcd. for C24H35N4O4 .0.2H$_2$O: C, 55.97; H, 7.63; N, 10.88. Found: C, 55.61; H, 7.51; N, 10.48.

Example 13

2-ethyl-2-{[4-({[(3-isopropyl-2-oxo-2,3-dihydro-1H-benzimidazol-1-yl)carbonyl]amino}methyl)piperidin-1-yl]methyl}butanoic acid

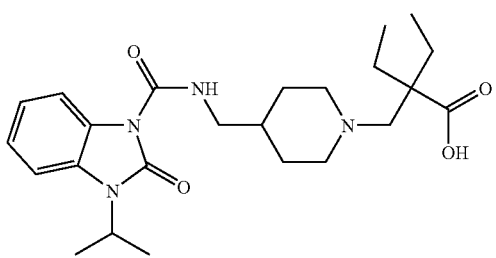

Step 1. Methyl 2-[(4-{[(tert-butoxycarbonyl)amino]methyl}piperidin-1-yl)methyl]-2-ethylbutanoate The title compound was prepared by a method similar to that shown in the Step 1 of Example 7 by using methyl 2-ethyl-2-formylbutanoate (Okano, K.; Morimoto, T.; Sekiya, M. *Journal of the Chemical Society, Chemical Communications,* 1985, 3, 119)
$^1$H-NMR (CDCl$_3$) δ: 4.62-4.48 (1H, br), 3.65 (3H, s), 3.01-2.93 (2H, m), 2.73-2.65 (2H, m), 2.46 (2H, s), 2.13-2.02 (2H, m), 1.73-1.50 (6H, m), 1.44 (9H, s), 1.28-1.10 (3H, m), 0.76 (6H, t, J=7.5 Hz)
MS (ESI) m/z: 357 (M+H$^+$).

Step 2. Methyl 2-ethyl-2-{[4-({[(3-isopropyl-2-oxo-2,3-dihydro-1H-benzimidazol-1-yl)carbonyl]amino}methyl)piperidin-1-yl]methyl}butanoate The title compound was prepared according to the procedure described in Step 2 of Example 8 from 1-isopropyl-1,3-dihydro-2H-benzimidazol-2-one and Methyl 2-[(4-{[(tert-butoxycarbonyl)amino}methyl}piperidin-1-yl)methyl]-2-ethylbutanoate (step 1 of Example 13).
$^1$H-NMR (CDCl$_3$) δ: 8.92-8.86 (1H, m), 8.28-8.23 (1H, m), 7.20-7.12 (3H, m), 4.77-4.61 (1H, m), 3.65 (3 H, s), 3.27 (2H, t, J=6.4 Hz), 2.75-2.66 (2H, m), 2.47 (2H, s), 2.16-2.05 (2H, m), 1.72-1.49 (10H, m), 1.38-1.21 (5H, m), 0.76 (6H, d, J=7.5 Hz)
MS (ESI) m/z: 459 (M+H$^+$).

Step 3. 2-ethyl-2-{[4-({[(3-isopropyl-2-oxo-2,3-dihydro-1H-benzimidazol-1-yl)carbonyl]amino}methyl)piperidin-1-yl]methyl}butanoic acid The title compound was prepared according to the procedure described in Step 5 of Example 3 from Methyl 2-ethyl-2-{[4-({[(3-isopropyl-2-oxo-2,3-dihydro-1H-benzimidazol-1-yl)carbonyl]amino}methyl)piperidin-1-yl]methyl}butanoate (step 3 of Example 13).
$^1$H-NMR (CDCl$_3$) δ: 8.03-8.94 (1H, m), 8.27-8.21 (1H, m), 7.20-7.12 (3H, m), 4.76-4.63 (1H, m), 3.34 (2 H, t, J=6.2 Hz), 3.16-3.05 (2H, m), 2.60 (2H, s), 2.55-2.38 (2H, m), 1.94-1.38 (2H, m), 1.80-1.38 (15H, m), 0.88 (6H, d, J=7.5 Hz)
MS (ESI) m/z: 445 (M+H$^+$).
Anal. Calcd. for C24H37N4O4Cl .0.2H2O: C, 59.48; H, 7.78; N, 11.56. Found: C, 59.38; H, 7.74; N, 11.29.

Example 14

1-[4-({[(3-isopropyl-2-oxo-2,3-dihydro-1H-benzimidazol-1-yl)carbonyl]amino}methyl)piperidin-1-yl]cyclopentanecarboxylic acid hydrochloride

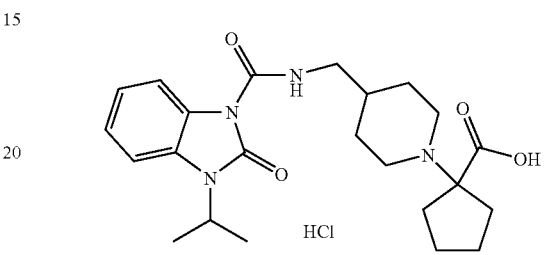

Step 1. tert-butyl 1-(4-oxopiperidin-1-yl)cyclopentanecarboxylate

The title compound was prepared by a method similar to that shown in the Step 3 of Example 1 by using tert-butyl 1-aminocyclopentanecarboxylate (WO 9105796)
MS (ESI) m/z: 268(M+H$^+$).
$^1$H-NMR (CDCl$_3$) δ: 2.93 (4H, t, J=5.9 Hz), 2.41 (4H, t, J=6.0 Hz), 2.39-2.26 (2H, m), 1.85-1.54 (8H, m), 1.46 (9H, s).

Step 2. tert-butyl 1-(4-cyanopiperidin-1-yl)cyclopentanecarboxylate

The title compound was prepared by a method similar to that shown in the Step 4 of Example 1 by using tert-butyl 1-(4-oxopiperidin-1-yl)cyclopentanecarboxylate.
MS (ESI) m/z: 279 (M+H$^+$).
$^1$H-NMR (CDCl$_3$) δ: 2.94-2.82 (2H, m), 2.67-2.49 (3H, m), 2.33-2.21 (2H, m), 1.96-1.72 (5H, m), 1.70-1.40 (6H, m), 1.48 (9H, s).

Step 3. tert-butyl 1-[4-(aminomethyl)piperidin-1-yl]cyclopentanecarboxylate

The title compound was prepared by a method similar to that shown in the Step 5 of Example 1 by using tert-butyl 1-(4-cyanopiperidin-1-yl)cyclopentanecarboxylate.
$^1$H-NMR (CDCl$_3$) δ: 3.07-2.95 (2H, m), 2.60-2.52 (2H, m), 2.41-1.19 (4H, m), 1.76-1.62 (4H, m), 1.61-1.40 (12H, m), 1.19-1.03 (2H, m).
MS (ESI) m/z: 283 (M+H$^+$).

Step 4. tert-butyl 1-[4-({[(3-isopropyl-2-oxo-2,3-dihydro-1H-benzimidazol-1-yl)carbonyl]amino}methyl)piperidin-1-yl]cyclopentanecarboxylate The title compound was prepared by a method similar to that shown in the Step 6 of Example 1 by using 1-isopropyl-1,3-dihydro-2H-benzimidazol-2-one and tert-butyl 1-[4-(aminomethyl)piperidin-1-yl]cyclopentanecarboxylate.

¹H-NMR (CDCl₃) δ: 8.96-8.84 (1H, m), 8.29-8.22 (1H, m), 7.21-7.11 (3H, m), 4.77-4.56 (1H, m), 3.29 (2 H, t, J=6.2 Hz), 3.07-2.94 (2H, m), 2.37-2.17 (4H, m), 1.82-1.63 (6H, m), 1.56 (6H, d, J=7.1 Hz), 1.46 (9 H, s), 1.61-1.49 (2H, m), 1.38-1.16 (3H, m).

MS (ESI) m/z: 485 (M+H⁺).

Step 5. 1-[4-({[(3-isopropyl-2-oxo-2,3-dihydro-1H-benzimidazol-1-yl)carbonyl]amino}methyl)piperidin-1-yl]cyclopentanecarboxylic acid hydrochloride The title compound was prepared by a method similar to that shown in the Step 5 of Example 12 by using tert-butyl 1-[4-({[(3-isopropyl-2-oxo-2,3-dihydro-1H-benzimidazol-1-yl)carbonyl]amino}methyl) piperidin-1-yl]cyclopentanecarboxylate.

¹H-NMR (DMSO-d₆) δ: 8.91-8.82 (1H, m), 8.07 (1H, d, J=7.5 Hz), 7.45 (1H, d, J=7.7 Hz), 7.26-7.09 (2H, m), 4.74-4.56 (1H, m), 3.60-3.00 (6H, m), 2.26-2.10 (4H, m), 1.96-1.57 (9H, m), 1.49 (6H, d, J=7.0 Hz).

MS (ESI) m/z: 429 (M+H⁺).

Anal. Calcd. for C23H33N4O4Cl: C, 59.41; H, 7.15; N, 12.05. Found: C, 59.14; H, 7.22; N, 11.82.

Example 15

N-({1-[(4-Oxycarbonyltetrahydro-2H-pyran-4-yl)methyl]-4-fluoropiperidin-4-yl}methyl)-3-isopropyl-2-oxo-2,3-dihydro-1H-benzimidazole-1-carboxamide

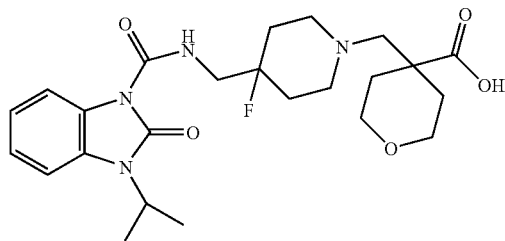

Step 1. Benzyl tetrahydropyran-4-yl-carboxylate

A mixture of tetrahydropyran-4-yl-carboxylic acid (910 mg, 6.99 mmol) and SOCl₂ (5.0 mL) was stirred for 1 h at 60° C. and concentrated in vacuo. To the residue were added benzyl alcohol (1.52 g, 14.1 mmol) and tetrahydrofuran (5.0 mL) at ambient temperature. The resulting mixture was stirred for 13 h at ambient temperature and concentrated in vacuo. The residue was purified by preparative thin layer chromatography (silica gel, eluting with hexane/ethyl acetate (2:1)) to give 1.08 g (70%) of the title compound as a pale yellow oil.

¹H NMR (CDCl₃) δ 7.45-7.25 (5H, m), 5.13 (2H, s), 3.95 (2H, m), 3.42 (2H, m), 2.59 (1H, m), 1.94-1.68 (4H, m).

Step 2. Benzyl 4-iodomethyltetrahydropyran-4-yl-carboxylate

The title compound was prepared according to the procedure described in step 1 of Example 3 from benzyl tetrahydropyran-4-yl-carboxylate (step 1 of Example 15).

¹H NMR (CDCl₃) δ 7.45-7.25 (5H, m), 5.19 (2H, s), 3.80 (2H, m), 3.47 (2H, m), 3.31 (2H, s), 2.18 (2H, m), 1.56 (2H, m).

Step 3. N-benzoyl-4-tert-butoxycarbonylaminomethyl-4-fluoropiperidine

A mixture of N-benzoyl-4-aminomethyl-4-fluoropiperidine (J. Med. Chem. 1999, 42, 1648-1660.) (3.54 g, 15.0 mmol) and di-tert-butyl dicarbonate (4.91 g, 22.5 mmol) in methanol (80 mL) was stirred at room temperature for 15 h and concentrated in vacuo. The resulting residue was chromatographed on a column of silica gel eluting with hexane/ethyl acetate (1:1) to give 4.52 g (89%) of the title compound as a colorless oil.

MS (ESI) m/z: 337 (M+H)⁺.

¹H NMR (CDCl₃) δ 7.55-7.25 (5H, m), 5.16 (1H, br t, J=6.3 Hz), 4.51 (1H, m), 3.62 (1H, m), 3.55-3.00 (4 H, m), 2.10-1.25 (4H, m), 1.43 (9H, s).

Step 4. 4-tert-Butoxycarbonylaminomethyl-4-fluoropiperidine

A mixture of N-benzoyl-4-tert-butoxycarbonylaminomethyl-4-fluoropiperidine (step 3 of Example 15) (4.42 g, 13.1 mmol), NaOH (2.62 g, 65.5 mmol), H₂O (9.00 mL) and ethanol (90.0 mL) was refluxed for 15 h and concentrated in vacuo. To the resulting residue were added water and chloroform. The organic layer was separated, dried over magnesium sulfate, and concentrated under reduced pressure. Recrystallization of the resulting solid with hexane-CH₂Cl₂ afforded a colorless solid 1.77 g (58%) as the titled compound.

MS (ESI) m/z: 233 (M+H)⁺.

¹H NMR (CDCl₃) δ 4.93 (1H, m), 3.30 (2H, dd, J=21.5, 6.3 Hz), 2.91 (4H, m), 1.88-1.34 (4H, m), 1.45 (9 H, s), The signal which correspond to amino group was not observed.

Step 5. tert-Butyl ({1-[(4-benzyloxycarbonyltetrahydro-2H-pyran-4-yl)methyl]-4-fluoropiperidin-4-yl}methyl)carbamate The title compound was prepared according to the procedure described in step 2 of Example 3 from 4-tert-butoxycarbonylaminomethyl-4-fluoropiperidine (step 4 of Example 15) and benzyl 4-iodomethyltetrahydropyran-4-yl-carboxylate (step 2 of Example 15).

MS (ESI) m/z: 465 (M+H)⁺.

¹H NMR (CDCl₃) δ 7.45-7.25 (5H, m), 5.16 (2H, s), 4.78 (1H, br t), 3.80 (2H, m), 3.46 (2H, m), 3.23 (2H, dd, J=21.9, 6.3 Hz), 2.64-2.32 (4H, m), 2.52 (2H, s), 2.08 (2H, m), 1.90-1.35 (6H, m), 1.45 (9H, s).

Step 6. N-({1-[(4-Benzyloxycarbonyltetrahydro-2H-pyran-4-yl)methyl]-4-fluoropiperidin-4-yl}methyl)-3-isopropyl-2-oxo-2,3-dihydro-1H-benzimidazole-1-carboxamide The title compound was prepared according to the procedure described in step 6 of Example 1 from 1-isopropyl-1,3-dihydro-2H-benzimidazol-2-one and tert-Butyl ({1-[(4-benzyloxycarbonyltetrahydro-2H-pyran-4-yl)methyl]-4-fluoropiperidin-4-yl}methyl)carbamate (step 5 of Example 15).

MS (ESI) m/z: 567 (M+H⁺).

¹H NMR (CDCl₃) δ 9.08 (1H, br t, J=6.0 Hz), 8.25 (1H, m), 7.46-7.06 (8H, m), 5.16 (2H, s), 4.71 (1H, septet, J=7.0 Hz), 3.80 (2H, m), 3.54 (2H, dd, J=20.9, 6.0 Hz), 3.46 (2H, m), 2.65-2.36 (4H, m), 2.53 (2 H, br s), 2.08 (2H, m), 1.88-1.44 (6H, m), 1.56 (6H, d, J=7.0 Hz).

Step 7. N-({1-(4-Oxycarbonyltetrahydro-2H-pyran-4-yl)methyl]-4-fluoropiperidin-4-yl}methyl)-3-isopropyl-2-oxo-2,3-dihydro-1H-benzimidazole-1-carboxamide The title compound was prepared according to the procedure described in Step 3 of Example 1 from N-({1-[(4-benzyloxycarbonyltetrahydro-2H-pyran-4-yl)methyl]-4-fluoropiperidin-4-yl}methyl)-3-isopropyl-2-oxo-2,3-dihydro-1H-benzimidazole-1-carboxamide (step 6 of Example 15).

MS (ESI) m/z: 477 (M+H)$^+$.

$^1$H NMR (CD$_3$OD) δ 7.93 (1H, m), 7.12 (1H, m), 7.02 (1H, m), 6.93 (1H, m), 4.49 (1H, septet, J=7.0 Hz), 3.65-3.36 (6H, m), 3.15-2.82 (4H, m), 2.80 (2H, br s), 1.98-1.70 (6H, m), 1.35 (6H, d, J=7.0 Hz), 1.34 (2H, m). The signals which correspond to amide and carboxylic acid were not observed.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The claimed invention is:

1. The compound: 4-{[4-({[(3-isopropyl-2-oxo-2,3-dihydro-1H-benzimidazol-1-yl)carbonyl]amino}methyl)piperidin-1-yl]methyl}tetrahydro-2H-pyran-4-carboxylic acid, or a pharmaceutically acceptable salt thereof.

2. A pharmaceutical composition comprising the compound or the pharmaceutically acceptable salt or solvate thereof, as claimed in claim 1, with or without at least one pharmaceutically acceptable carrier.

3. A pharmaceutical composition as claimed in claim 1, further comprising at least one pharmacologically active agent in addition to the compound.

\* \* \* \* \*